(12) United States Patent
Thomas et al.

(10) Patent No.: US 10,500,087 B2
(45) Date of Patent: Dec. 10, 2019

(54) COOLING DEVICES FOR PROVIDING COOLING THERAPY TO THE BODY

(71) Applicant: Relief Technologies, Inc., San Francisco, CA (US)

(72) Inventors: Jonathan Moulton Thomas, San Francisco, CA (US); Brian James Krieger, San Francisco, CA (US); Richard Thomas Caligaris, Los Altos, CA (US); Elizabeth Ann Miracle, San Francisco, CA (US); Grace Hina Lee, San Francisco, CA (US)

(73) Assignee: Relief Technologies, Inc., San Francisco, CA (US)

(*) Notice: Subject to any disclaimer, the term of this patent is extended or adjusted under 35 U.S.C. 154(b) by 0 days.

(21) Appl. No.: 15/947,124

(22) Filed: Apr. 6, 2018

(65) Prior Publication Data

US 2018/0289531 A1 Oct. 11, 2018

Related U.S. Application Data

(60) Provisional application No. 62/483,689, filed on Apr. 10, 2017.

(51) Int. Cl.
*H01L 23/38* (2006.01)
*A61F 7/00* (2006.01)
(Continued)

(52) U.S. Cl.
CPC .............. *A61F 7/007* (2013.01); *A61B 34/25* (2016.02); *A61F 7/02* (2013.01); *A61F 7/10* (2013.01);
(Continued)

(58) Field of Classification Search
CPC ....................................................... H01L 23/38
(Continued)

(56) References Cited

U.S. PATENT DOCUMENTS 3,554,815 A 1/1971 Osborn
5,065,758 A 11/1991 Whitehead et al.
(Continued)

OTHER PUBLICATIONS

Custom Thermoelectric—TEC Specification Sheet—Thermoelectric Cooler Data Sheet for Part No. 03511-5L31-03CFL, Copyright 2008, 1 page.
(Continued)

*Primary Examiner* — Jami Valentine Miller
(74) *Attorney, Agent, or Firm* — RMCK Law Group, PLC

(57) ABSTRACT

A cooling device includes a package substrate, a plurality of cooling units, and device electronics. The plurality of cooling units are configured to cool a user's body. Each cooling unit includes a plurality of semiconductor cooling elements sandwiched between a first cooling unit substrate and a second cooling unit substrate. Each of the cooling units is connected to the package substrate. The device electronics are coupled to the cooling units. The device electronics are configured to store a first cooling device profile that includes data indicating an amount of power to deliver to each of the cooling units over a period of time. The device electronics are configured to deliver power to the cooling units according to the first cooling device profile, wirelessly receive a second cooling device profile from an external computing device, and deliver power to the cooling units according to the second cooling device profile.

20 Claims, 50 Drawing Sheets

(51) Int. Cl.

| | | |
|---|---|---|
| *A61F 7/10* | (2006.01) | |
| *H01L 23/367* | (2006.01) | |
| *A61F 7/02* | (2006.01) | |
| *H01L 23/373* | (2006.01) | |
| *H01L 23/473* | (2006.01) | |
| *H01L 35/32* | (2006.01) | |
| *A61B 34/00* | (2016.01) | |

(52) U.S. Cl.
CPC ...... *H01L 23/3675* (2013.01); *H01L 23/3731* (2013.01); *H01L 23/38* (2013.01); *H01L 23/473* (2013.01); *H01L 35/32* (2013.01); *A61F 2007/0001* (2013.01); *A61F 2007/003* (2013.01); *A61F 2007/005* (2013.01); *A61F 2007/0027* (2013.01); *A61F 2007/0075* (2013.01); *A61F 2007/0078* (2013.01); *A61F 2007/0086* (2013.01); *A61F 2007/0093* (2013.01); *A61F 2007/0095* (2013.01); *A61F 2007/0225* (2013.01); *A61F 2007/0228* (2013.01); *A61F 2007/0292* (2013.01); *A61F 2007/0295* (2013.01); *A61F 2007/108* (2013.01)

(58) Field of Classification Search
USPC .......................................................... 257/712
See application file for complete search history.

(56) References Cited

U.S. PATENT DOCUMENTS

| | | | |
|---|---|---|---|
| 5,605,047 A | 2/1997 | Park et al. | |
| 6,141,969 A | 11/2000 | Launchbury et al. | |
| 6,230,501 B1* | 5/2001 | Bailey, Sr. ........... | A43B 1/0054 |
| | | | 62/51.1 |
| 6,610,084 B1 | 8/2003 | Torres | |
| 6,904,956 B2 | 6/2005 | Noel | |
| 7,999,172 B2* | 8/2011 | Yu ........................... | H01L 35/34 |
| | | | 136/203 |
| 2018/0193185 A1* | 7/2018 | Thomas ................. | A61F 7/007 |

OTHER PUBLICATIONS

Li, X. et al., "Thermoelectric Cooling Device Integrated with PCM Heat Storage for MS Patients," Energy Procedia, vol. 61, Dec. 2014, pp. 2399-2402.
SavENRG™ PCM-OM37P Product Data Sheet, "savENRG™ Phase Change Materials for Thermal Energy Storage," Jun. 2013, 1 page.

* cited by examiner

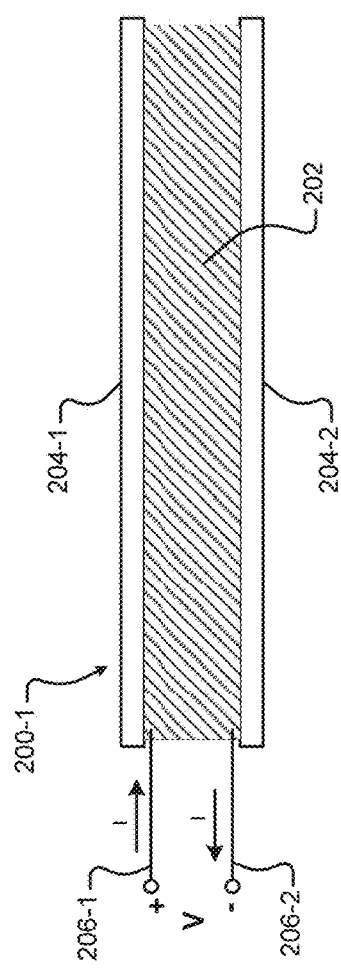
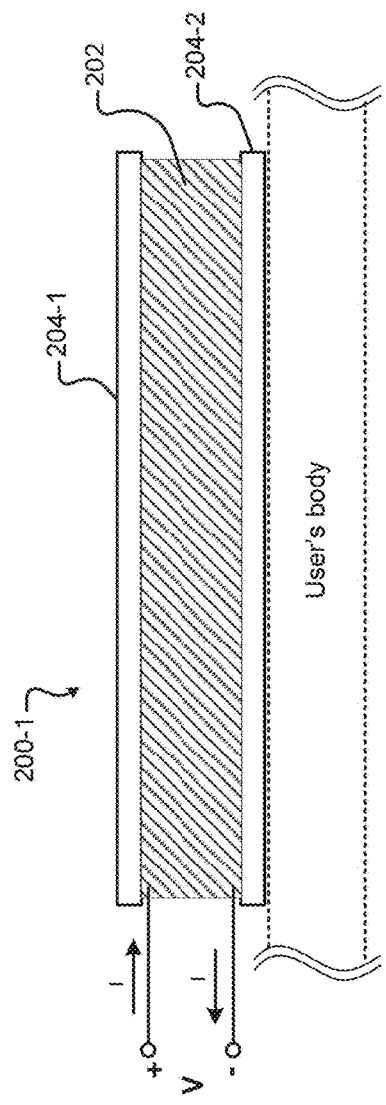
FIG. 2A
FIG. 2B

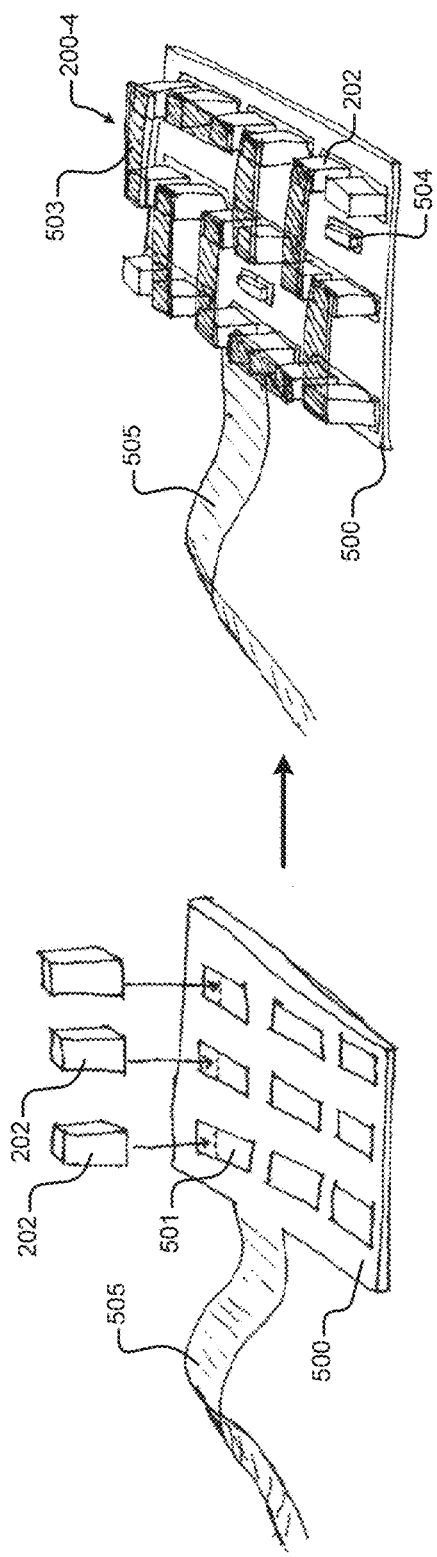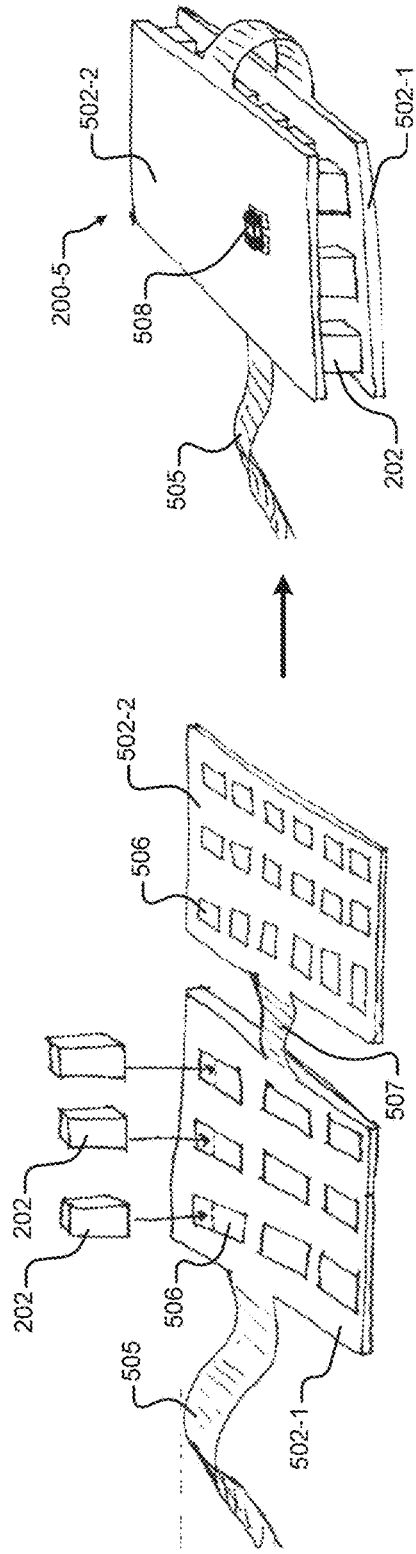

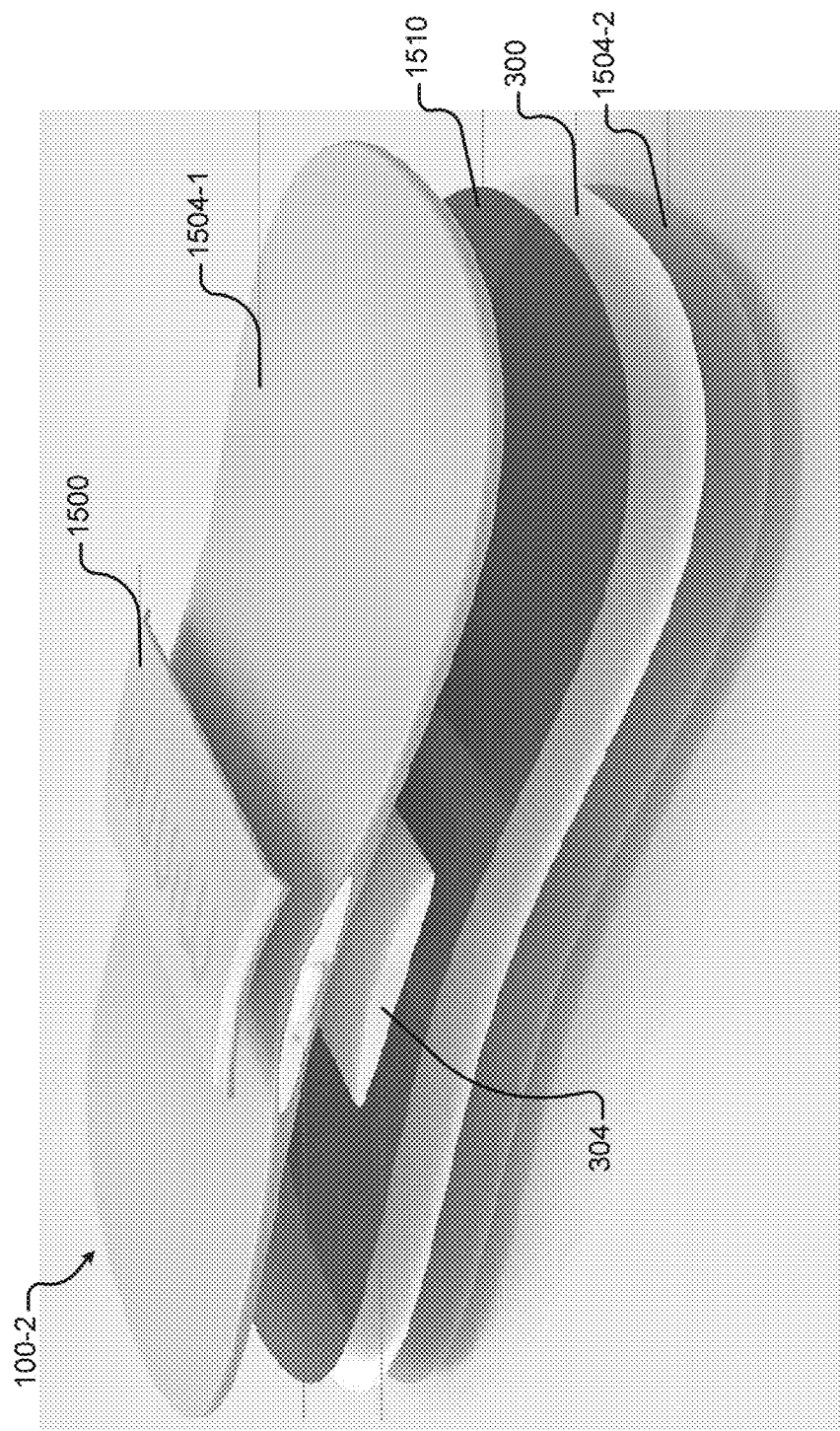

COOLING DEVICES FOR PROVIDING COOLING THERAPY TO THE BODY

CROSS-REFERENCE TO RELATED APPLICATIONS

This application claims the benefit of U.S. Provisional Application No. 62/483,689, filed on Apr. 10, 2017. The disclosure of the above application is incorporated herein by reference in its entirety.

FIELD

The present disclosure relates to cooling devices that provide cooling for a user's body.

BACKGROUND

Cooling therapy (e.g., ice pack therapy) can be used to provide relief/rehabilitation for a variety of ailments, such as injured muscles (e.g., muscle pain and/or soreness), injured joints, and other injured tissues. Cooling therapy can be applied in a variety of manners, such as via direct contact with the skin (e.g., via an ice pack or ice bath). Cooling therapy may absorb heat from the affected area, which may cause vasoconstriction, decreased local metabolism and enzymatic activity, and decreased oxygen demand. The therapeutic effects of cooling may include pain relief and a reduction in swelling of the affected areas.

SUMMARY

In one example, the present disclosure is directed to a cooling device comprising a package substrate, a plurality of cooling units, and device electronics. The plurality of cooling units are configured to cool a user's body. Each cooling unit comprises a plurality of semiconductor cooling elements sandwiched between a first cooling unit substrate and a second cooling unit substrate. Each of the cooling units is connected to the package substrate. The device electronics are coupled to the cooling units. The device electronics are configured to store a first cooling device profile that includes data indicating an amount of power to deliver to each of the cooling units over a period of time. The device electronics are configured to deliver power to the cooling units according to the first cooling device profile, wirelessly receive a second cooling device profile from an external computing device, and deliver power to the cooling units according to the second cooling device profile.

In another example, the present disclosure is directed to a cooling device comprising a plurality of cooling units, device electronics, and a thermal reservoir material. The plurality of cooling units are configured to cool a user's body. Each cooling unit comprises a plurality of semiconductor cooling elements sandwiched between a first cooling unit substrate and a second cooling unit substrate. The device electronics are coupled to the cooling units. The device electronics are configured to deliver power to each of the cooling units to cool the user's body. The delivery of power to the cooling units causes the transfer of heat from the first cooling unit substrates to the second cooling unit substrates. The thermal reservoir material is in contact with the second cooling unit substrates.

BRIEF DESCRIPTION OF THE DRAWINGS

The present disclosure will become more fully understood from the detailed description and the accompanying drawings.

FIGS. 2A-2E illustrate example cooling units.

FIGS. 5A-5D illustrate fabrication of cooling units.

In the drawings, reference numbers may be reused to identify similar and/or identical elements.

DETAILED DESCRIPTION

Figure 1A:
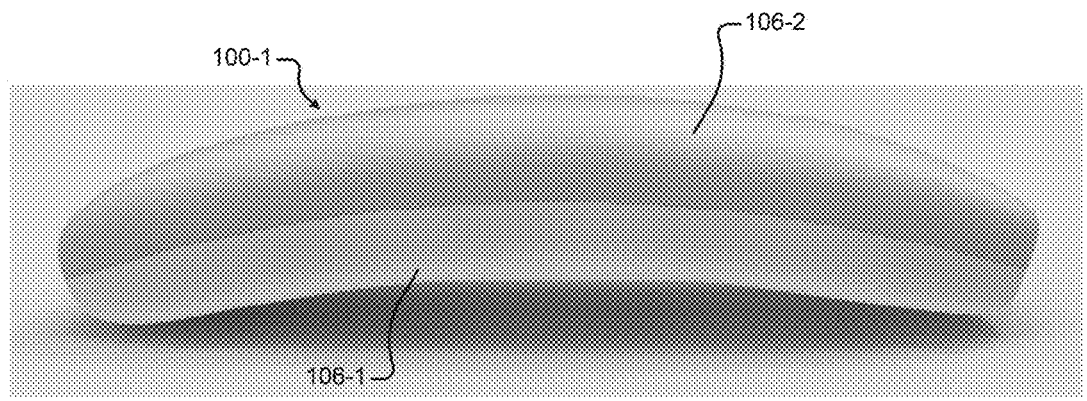
FIGS. 1A-1C illustrate a first example cooling device.

A cooling device 100 of the present disclosure may be used to provide relief for a variety of different conditions including, but not limited to, muscle soreness, headaches, joint pain, burns, and arthritis. The cooling device 100 may also be used to provide relief for pelvic pain conditions and other conditions, such as chronic pelvic pain, dyspareunia, vulvodynia, endometriosis, dysmenorrhea (menstrual pain), and hemorrhoid discomfort.

A cooling device 100 (e.g., a cooling pad) of the present disclosure includes one or more cooling units 200 that can cool one or more areas of a user's body. The cooling device 100 can include a device package that houses the one or more cooling units 200. Example cooling devices 100-1, 100-2, ..., 100-8 are illustrated in FIGS. 1A-1C and FIGS. 15A-21B. Example cooling units 200-1, 200-2, ..., 200-9 are illustrated in FIGS. 2A-3E and FIGS. 5D-6D. In some cases, cooling devices and cooling units may generally be indicated by callout 100 and callout 200, respectively.

A user can control the cooling device 100 manually. For example, the cooling device 100 may include user input devices 102 (e.g., manual controls) and/or be controlled via an external computing device 104, such as a user's phone (e.g., see FIG. 1C). The cooling device 100 may also automatically execute cooling device profiles that include data indicating how the cooling device 100 should operate over time (e.g., see FIGS. 11A-11E).

In some implementations, a cooling unit 200 can include a plurality of cooling elements 202 sandwiched between two cooling unit substrates 204, which may be flexible and/or rigid. A cooling unit 200 can also include electrical contacts (e.g., 206-1, 206-2 of FIG. 2A) for connecting to device electronics included in the cooling device 100. In some implementations, the cooling elements 202 may be connected in series between the electrical contacts such that current can be delivered through the cooling elements 202 via the electrical contacts (e.g., see FIG. 6A). In some implementations, the cooling unit 200 may be a thermoelectric device (e.g., a solid-state heat pump) that includes semiconductor cooling elements mounted between two substrates (e.g., ceramic substrates). Individual cooling units may be arranged on a device package substrate (e.g., package substrate 300) included in the cooling device 100. The device package can provide support to the cooling units 200 so that the cooling units 200 can be positioned near the user's body. The arrangement of the cooling units 200 may define different cooling zones of the cooling device 100.

The cooling device 100 includes device electronics (e.g., at 302 in FIGS. 3A-3B) that control the cooling units 200. For example, the device electronics may control the cooling units 200 by controlling power (e.g., current/voltage) delivered to the cooling units 200 via the electrical contacts on the cooling units 200. The device electronics may increase/decrease the amount of power applied to a cooling unit 200 to increase/decrease the amount of cooling provided by the cooling unit 200. The polarity of the voltage and direction of current applied to a cooling unit 200 may control which side of the cooling unit 200 provides cooling. The side (e.g., cooling unit substrate) that provides cooling may be referred to herein as the "cold side" of the cooling unit. The side (e.g., cooling unit substrate) of the cooling unit to which heat is transferred may be referred to as the "hot side" of the cooling unit.

Due to electrical resistance within the thermo-electric device, the cooling units 200 may generate heat during use. If this resistive heat is not removed from the thermo-electric device, the net temperature of the device (including the temperature of the cold side) can increase during use, thereby decreasing its cooling effect. In some implementations, the cooling device 100 may include one or more thermal reservoirs (e.g., at 700-1 to 700-6 of FIGS. 7A-7K) on the hot side of the cooling units 200. The thermal reservoirs 700 may act as heat sinks that absorb heat from the hot side of the cooling units 200. By absorbing heat from the cooling units 200, the thermal reservoirs 700 may allow the cooling units 200 to remain at a lower temperature, thereby allowing the cold side of the cooling units 200 to remain at a lower temperature for longer periods of operation. In some implementations, the thermal reservoirs 700 may include a phase change material. In some implementations, the thermal reservoirs may comprise a single-phase material that has a desirable heat capacity (e.g., the ability to absorb large amounts of heat while exhibiting minimal temperature change).

In some implementations, the cooling device 100 may include one or more sensors (e.g., temperature, orientation, motion, and/or pressure sensors). In these implementations, the device electronics may control cooling based on data acquired from the one or more sensors. In some implementations, the cooling device may include a battery 304 (e.g., see FIGS. 3A-3B). In these implementations, the device electronics can manage charging/discharging of the battery 304 and control cooling based on a variety of conditions, such as a state of charge of the battery 304, the currently running cooling device profile, and/or a target device run time indicated by the user.

In some implementations, the cooling device 100 may include user interface devices that allow the user to interact with the cooling device 100. For example, the cooling device 100 may include buttons, switches, touch sensitive controls, and/or a display that allow the user to control/monitor the amount of cooling. The device electronics may communicate with the user interface devices in order to control cooling and provide output to the user. In some implementations, the device electronics may include electronics that can communicate with an external wired/wireless computing device, such as a user's cell phone (e.g., see FIG. 1C). In these implementations, the user may control/monitor cooling using the external computing device. The external computing device may be referred to herein as a "user device."

The cooling device 100 can be powered in a variety of different ways. In some implementations, the cooling device 100 can be configured to receive a battery 304 (e.g., rechargeable/non-rechargeable battery) from the user. The battery 304 may be removable by hand and/or fixed within the cooling device 100 (e.g., accessible using tools). Additionally, or alternatively, the cooling device 100 can be plugged into an external power source (e.g., via a power input port) that may power the cooling device 100 and/or charge the battery 304.

The arrangement of the one or more cooling units 200 may create one or more cooling zones. A cooling zone refers to an area of the cooling device 100 in which the cooling device 100 cools the user. A user may control cooling in a cooling zone by controlling power delivered to the cooling unit(s) 200 making up the cooling zone. In some cases, cooling zones can be surrounded by warmer areas of the cooling device 100 (e.g., areas not including cooling units). Put another way, if a cooling device 100 has multiple cooling zones, the cooling zones can be separated from one another. In other cases, the cooling zones may not be separated, but instead, some of the cooling zones may merge together such that the two cooling zones are bridged by a cooled area instead of a warmer area.

The cooling device 100 can be configured to operate in one or more of three modes, which may be referred to herein as a manual mode, an automatic mode, or a mixed mode. The cooling device 100 can operate in a manual mode in which the cooling device 100 is configured to cool in response to a user's manual input. For example, while operating in the manual mode, a user can control cooling using manual controls on the cooling device 100 and/or using the user device 104. In a more specific example, the user can incrementally increase/decrease cooling in different cooling zones using manual controls and/or graphical controls rendered on a graphical user interface (GUI) of the user device 104. In the manual mode, the user may control one or more of the cooling zones. If the cooling device 100 has multiple cooling zones, the user may manually control the cooling zones independently or together.

The cooling device 100 can operate in an automatic mode in which the cooling device 100 cools according to a cooling profile, or sequence of profiles, loaded on the cooling device 100. The cooling profile can include data indicating how the cooling device 100 should cool the one or more cooling zones. For example, if a cooling device 100 includes a single cooling unit 200, the cooling profile may include data that indicates how to control the cooling unit 200. In this example, the cooling profile may include data indicating the amount of power (e.g., voltage/current) to be delivered to the cooling unit 200 over a period of time. FIGS. 11A-11E illustrate example cooling profiles that may be used by the cooling device 100. In cooling devices 100 including multiple cooling units 200, a cooling profile can include data indicating the amount of power (e.g., voltage/current) to be delivered to each of the multiple cooling units 200. A cooling profile may also indicate how the cooling device 100 should operate in response to data acquired from one or more sensors included on the cooling device 100. For example, the cooling profile may indicate whether to increase/decrease the delivery of power based on a detected temperature or motion-sensitive sensor.

The cooling device 100 can store one or more cooling profiles. In some implementations, the cooling profiles may be stored permanently in memory (e.g., in a ROM), and the user can select from the cooling profiles using manual controls and/or a GUI. In some implementations, the user can load different cooling profiles onto the cooling device 100 (e.g., from the user device 104) and then select from the loaded cooling profiles.

The cooling device 100 may operate in a mixed mode during which the user can modify/update a cooling profile while the cooling device 100 is cooling according to the cooling profile. Modification of the cooling profile may refer to a situation where any portion of the cooling profile is changed by the user. The user can modify the cooling profile in a variety of different ways. For example, the user may modify a cooling profile by: 1) adjusting the amount of cooling (e.g., the voltage/current) by one or more cooling units 200, 2) adjusting the frequency of cooling (e.g., frequency of cooling pulses) in one or more cooling units 200, 3) adjusting timing delays between the one or more cooling units 200, and/or 4) loading a new cooling profile for one or more of the cooling units 200. In some mixed mode implementations, the cooling device 100 may memorize a cooling profile generated by the user. For example, the user may modify the amount of cooling provided by the cooling device 100 (e.g., using the user device 104 and/or manual controls) in one or more cooling units 200 and the cooling device 100 may store a cooling profile that corresponds to the user's cooling pattern.

In some implementations, the cooling device 100 can be configured to operate in any of the three modes. For example, the cooling device 100 can be configured to allow the user to select the mode (e.g., using a button or GUI). In some implementations, the cooling device 100 can have more limited functionality. For example, the cooling device 100 may be configured to operate in one or two of the modes, but not the other mode(s). For example, the cooling device 100 may be configured to operate in the manual mode, but not the automatic or mixed modes.

The user can generate new cooling profiles in a variety of different ways. In some implementations, the user can create a new cooling profile using a computing device other than the cooling device 100, such as a cell phone or laptop computer. The user can then load the newly created cooling profile onto the cooling device 100 (e.g., using the user device 104). In some implementations, the user can create a new cooling profile from scratch (e.g., without using another existing cooling profile). In other implementations, the user can create a new cooling profile by modifying an existing cooling profile. For example, the user can modify an existing cooling profile running on the cooling device 100 (e.g., in the mixed mode) and then save the modified cooling profile as a new cooling profile. As another example, the user may load an existing cooling profile on an external computing device, modify the loaded cooling profile, and then save the modified cooling profile on the cooling device as a new cooling profile. The user may also use the cooling device 100 (e.g., a user input device such as a touchscreen) to generate new cooling profiles and/or modify existing cooling profiles.

Figure 10:
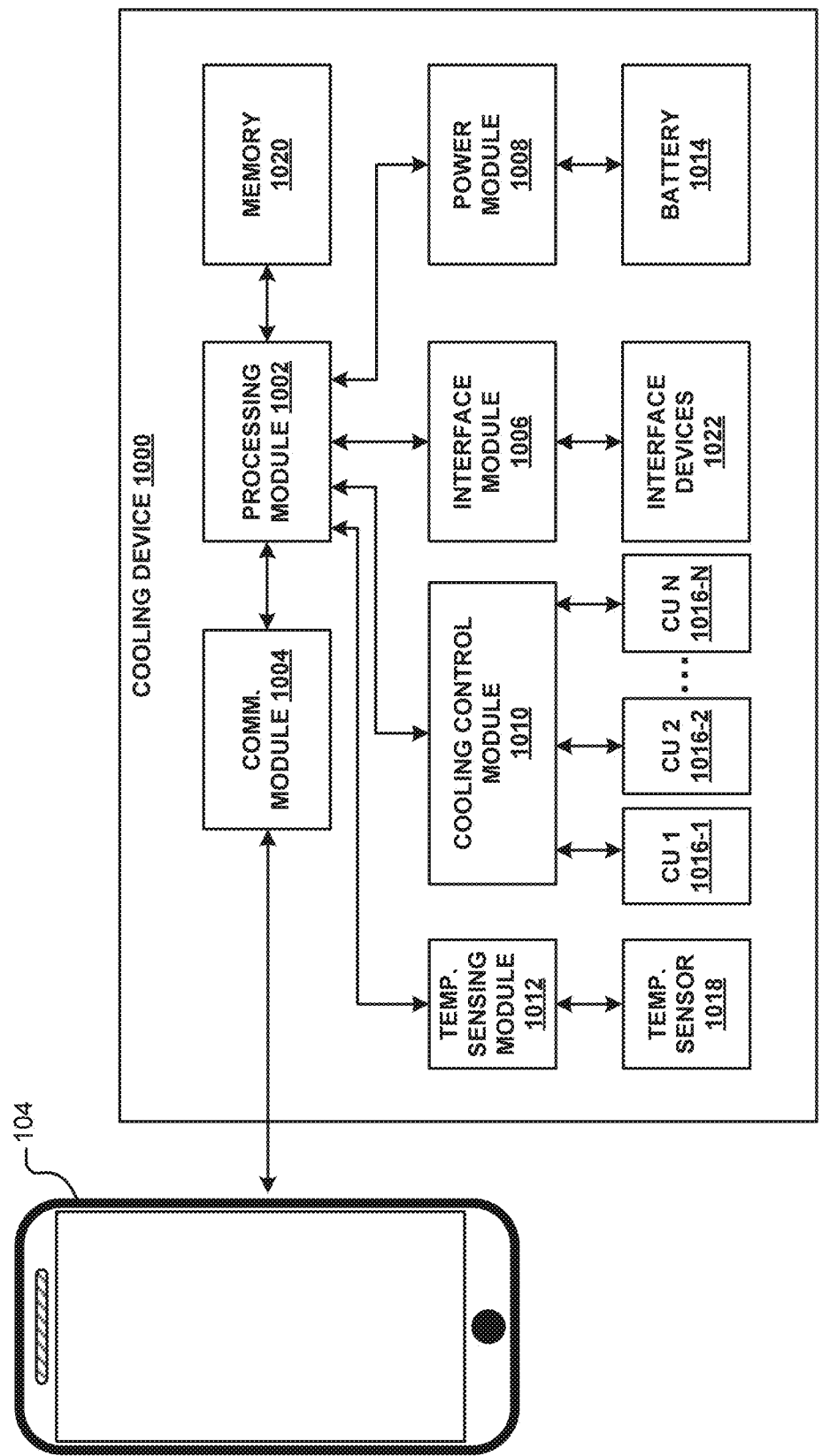
FIG. 10 is a functional block diagram of an example cooling device.

The cooling device 100 can store one or more cooling profiles in memory (e.g., memory 1020 of FIG. 10). The cooling device 100 can update the stored cooling profiles over time. For example, the cooling device 100 can delete stored cooling profiles and add additional cooling profiles to memory. The cooling device 100 can acquire cooling profiles from different sources. For example, if the cooling device 100 includes wired/wireless communication technology (e.g., WiFi, Bluetooth, Universal Serial Bus, etc.), the cooling device 100 can retrieve cooling profiles via the internet (e.g., from the remote server 1302 of FIG. 13) and/or the user device 104.

In some implementations, the cooling device 100 can include one or more sensors. The sensors may include, but are not limited to, a temperature sensor, a motion sensor, an orientation sensor, and a pressure/force sensor. A temperature sensor may indicate the temperature of an area of the cooling device 100 in the location of the temperature sensor. Example temperature sensors may include, but are not limited to, thermocouples, thermistors, resistance temperature detectors, and semiconductor based temperature sensors. In some implementations, the cooling units 200 may be used as temperature sensors. For example, a cooling unit 200 may generate a voltage based on the temperature difference across it. A motion sensor may generate a motion signal that indicates an amount of motion of the cooling device 100 (e.g., rotation/translation). Example motion sensors may include, but are not limited to, linear or angular accelerometers, gyroscopes, magnetometers, or integrated inertial measurement units. An orientation sensor may generate an orientation signal that indicates the orientation of the cooling device 100 (e.g., indicating a user's posture). Example orientation sensors may include, but are not limited to, linear or angular accelerometers, gyroscopes, magnetometers, or integrated inertial measurement units. A pressure/force sensor may indicate an amount of pressure/force in an area of the cooling device.

One or more sensors may be located on or within the device package. The temperature sensors may be positioned near cooling units 200 so that the temperature indicated by the temperature sensors reflect the temperature near one or more cooling units 200. Integrating the temperature sensors onto the substrates (e.g., cooling unit substrates and/or package substrates) may be beneficial in some implementations. For example, integrating a temperature sensor onto one of the substrates (e.g., FIG. 5B, FIG. 5D, and FIG. 8B) may provide for more accurate temperature sensing at the location where the user is being cooled. Additionally, or alternatively, the temperature sensors may be located farther from the cooling units 200, such as along with the device electronics, which may be located off of a package substrate. In some implementations, a temperature sensor can be placed in contact with a user's body. For example, a temperature sensor may be embedded in an external portion of the device package in contact with the user's body. As another example, a temperature sensor may be attached externally to the cooling device 100 via a wire and sandwiched between the user and the cooling device during use.

The orientation/motion sensors may also be included on the substrate (e.g., cooling unit substrates and/or package substrates) and/or along with the device electronics in order to detect the orientation/motion of the cooling device 100 (i.e., the user). In some implementations, an orientation/motion sensor may be included on the user device 104 (e.g., a cell phone) which may be carried by the user (e.g., in their hand or pocket) and, therefore, detect the orientation/motion of the user. In these implementations, the user device 104 may communicate with the cooling device 100 so that the cooling device 100 can modify cooling based on the user's orientation/motion as determined by the user device 104.

The device electronics may control cooling based on data acquired from the sensors. For example, with respect to a temperature sensor, the device electronics may control the cooling device 100 to maintain a target temperature. As another example, the device electronics may control the cooling device 100 to maintain a temperature that is greater than a threshold temperature (e.g., a minimum user comfort temperature and/or a minimum cooling device temperature). As another example, the device electronics may control the cooling device 100 to maintain a temperature below a maximum threshold temperature to prevent the cooling device from overheating (e.g., restrict or turn off power delivery when the max threshold is reached). With respect to the orientation/motion sensors, the device electronics may change cooling profiles/intensity based on a user's orientation and/or amount of motion. In a specific example, if a motion sensor detects changes indicative of user movement, the device electronics may be configured to increase cooling to alleviate discomfort resulting from movement. In a different specific example, the device electronics may be configured to increase cooling when a user is seated (e.g., as detected by the orientation/motion sensors) in order to alleviate discomfort resulting from sitting for long periods of time.

The cooling device 100 can determine a user status based on data acquired from one or more sensors. The cooling device 100 may load different cooling profiles corresponding to the different user statuses. For example, the cooling device 100 may include a seated cooling profile, a standing cooling profile, a walking cooling profile, and a running cooling profile that may be loaded in response to the cooling device 100 detecting a corresponding user status. In a specific example, if the cooling device 100 determines that a user is seated (e.g., upright posture with little motion), the cooling device 100 may load a seated cooling profile. At a later time, if the cooling device 100 detects that a user transitions from a seated position to walking, the cooling device 100 may load the walking cooling profile. The user may configure the different cooling profiles for different statuses. In some cases, the user may configure the cooling device 100 to cease cooling during some user activities and provide cooling during other activities. For example, the cooling device 100 may be configured to remain in a standby state (e.g., where cooling is turned off) when the user is seated, and then provide cooling when the user is standing. A user may configure the cooling device 100 in such a manner when the user feels little or no discomfort when seated, but then feels discomfort when standing. Additional user statuses can include user posture, such as whether the user is upright or leaning to one side. In some implementations, instead of loading a different cooling profile for a different status, the cooling device 100 can be configured to adjust parameters of the cooling profile, such as the amplitude of the cooling, the frequency of cooling pulses, or the phase difference between different cooling zones.

The cooling device 100 can be configured to operate with varying degrees of autonomy with respect to a user device 104. In some implementations, the cooling device 100 can be configured to operate without any communication with the user device 104. For example, the cooling device 100 may not include wired/wireless communication technology for communicating with a user device 104. In other implementations, the cooling device 100 may be configured to communicate with the user device 104, but operate autonomously without further communication with the user device 104. For example, the cooling device 100 may be configured to receive cooling profiles from the user device 104 and then operate according to the cooling profiles without additional communication with the user device 104. In other implementations, the cooling device 100 may be configured to make intermittent communication with the user device 104 and operate according to instructions and/or cooling profiles received from the user device 104. In these examples, the cooling device 100 may intermittently communicate with the user device 104 to receive instructions, such as user-input instructions for increasing/decreasing the amount of cooling. Accordingly, in some cases, the user device 104 can adjust operation of the cooling device 100 over time while the cooling device 100 is operating (e.g., in the automatic and/or mixed mode). During communication with the user device 104, the cooling device 100 may also send status updates back to the user device 104 (e.g., zone temperatures, battery status, active cooling profile, and other data).

The user device 104 and cooling device 100 can communicate using a variety of different communication protocols. In some implementations, communication between the user device 104 and the cooling device 100 may involve pairing followed by periodic polling/updating of data. The connection between the user device 104 and the cooling device 100 may be continuous (e.g., streaming data and/or control). Alternatively, the connection between the user device 104 and the cooling device 100 may be intermittent (e.g. downloading of a profile and/or instructions).

Figure 8A:
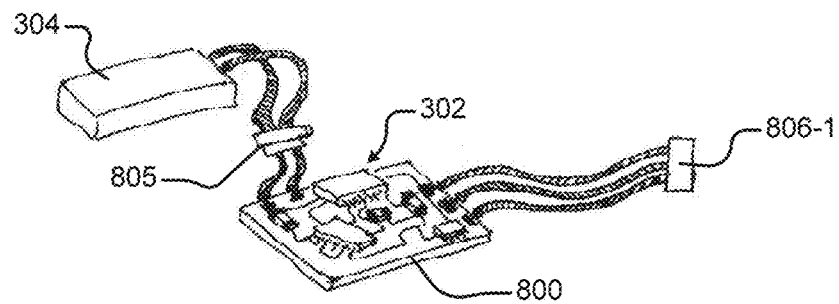
FIGS. 8A-8C illustrate connections between cooling units, devices electronics, and a battery.
Figure 8B:
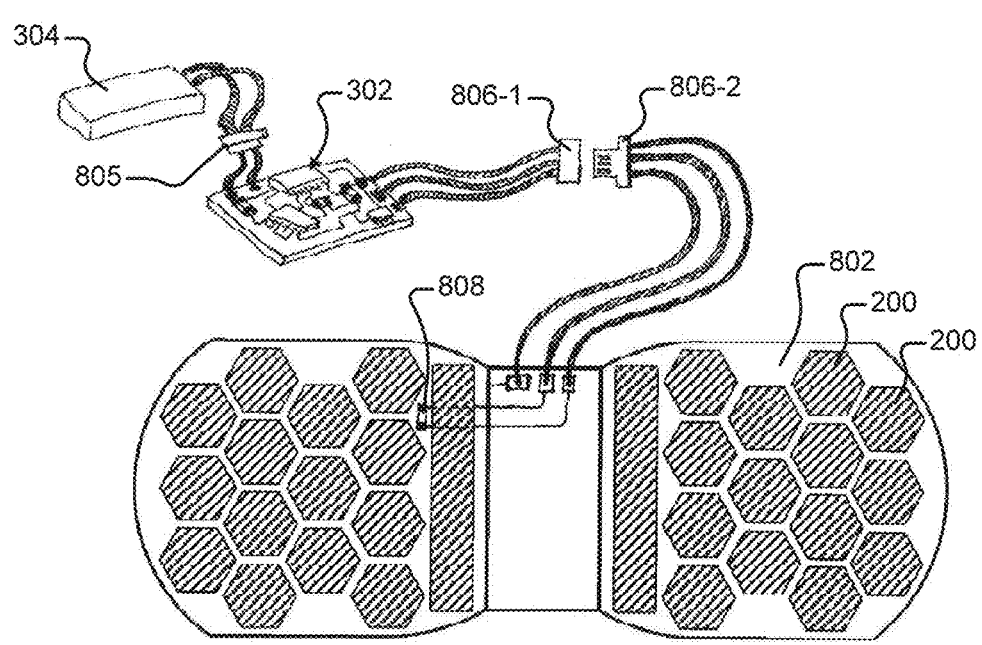
Figure 8C:
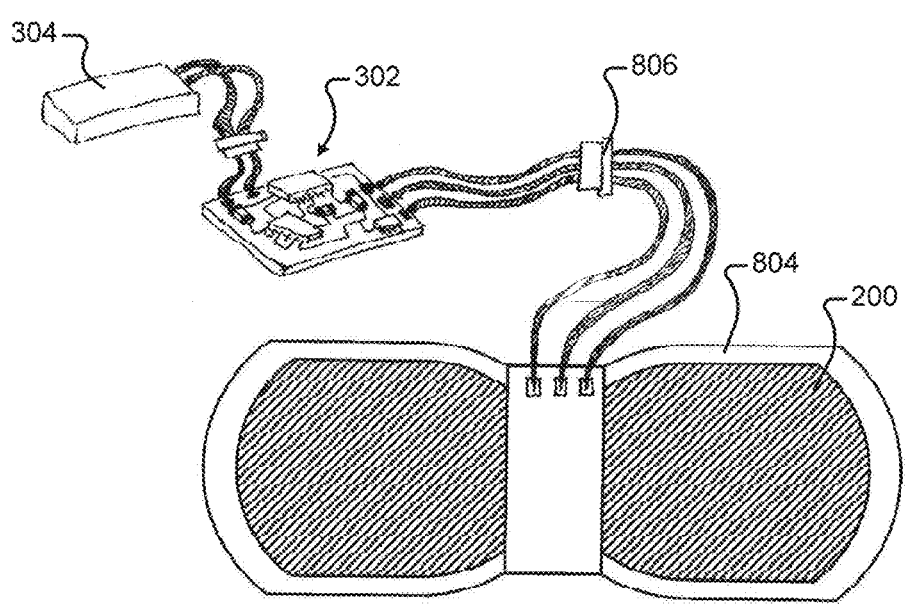
Figure 9:
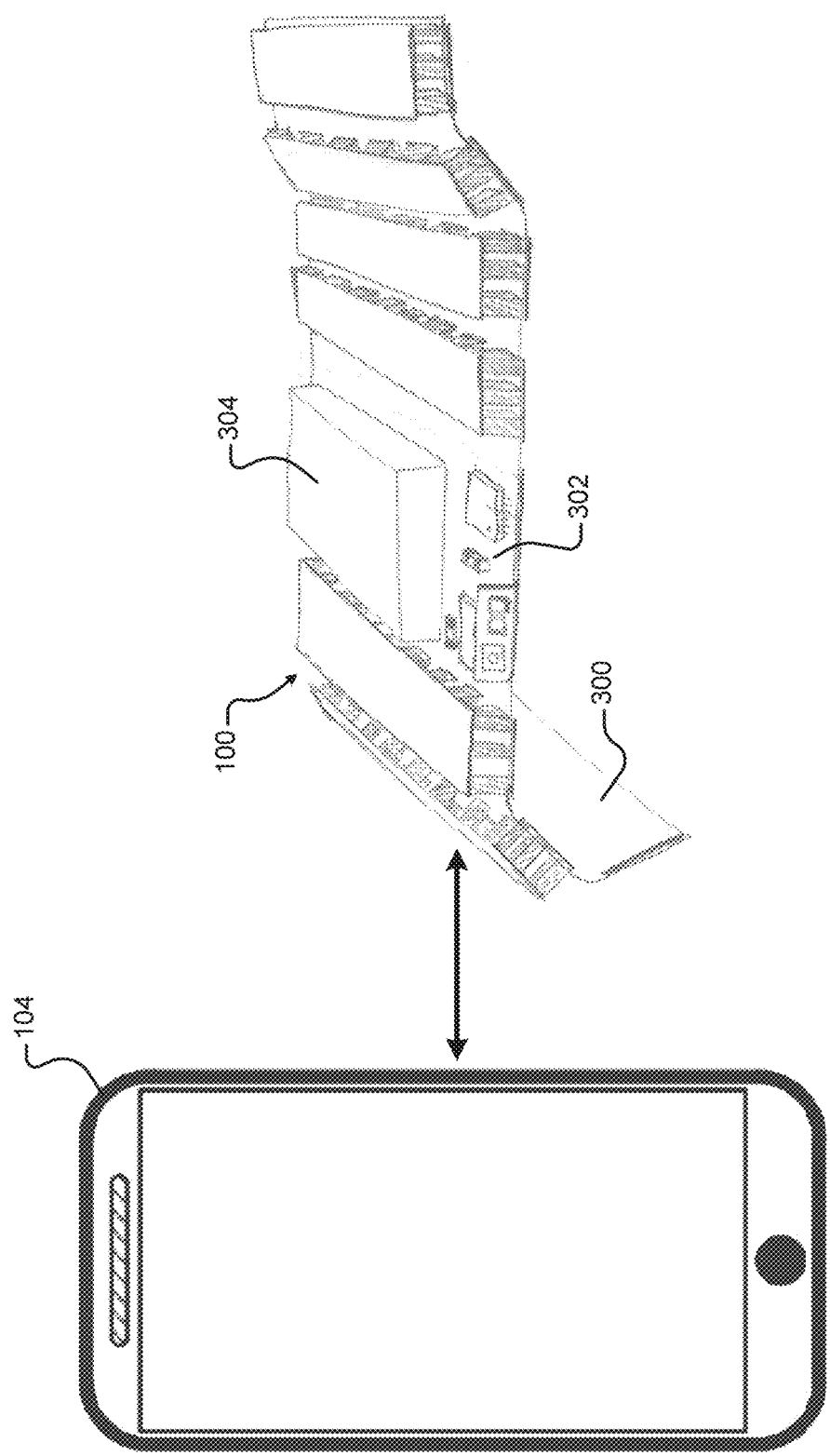
FIG. 9 illustrates communication between a user device and a cooling device.
Figure 12C:
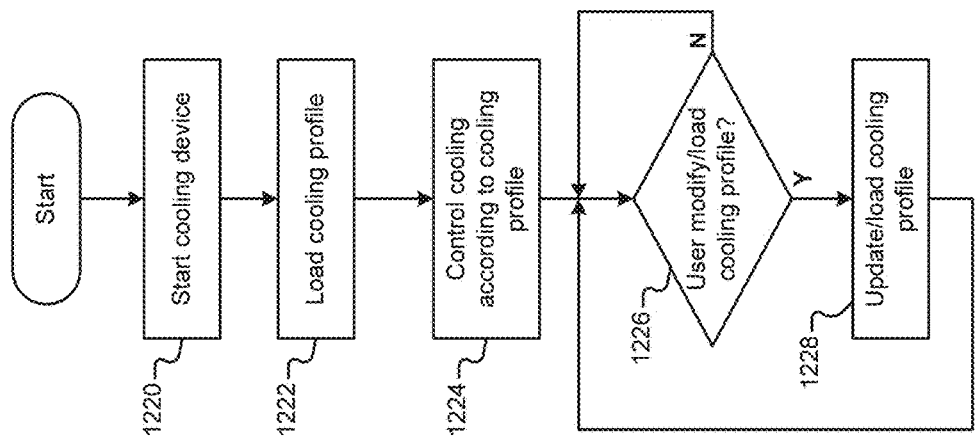
FIGS. 12A-12C are flow diagrams that illustrate different modes of cooling device operation.
Figure 12B:
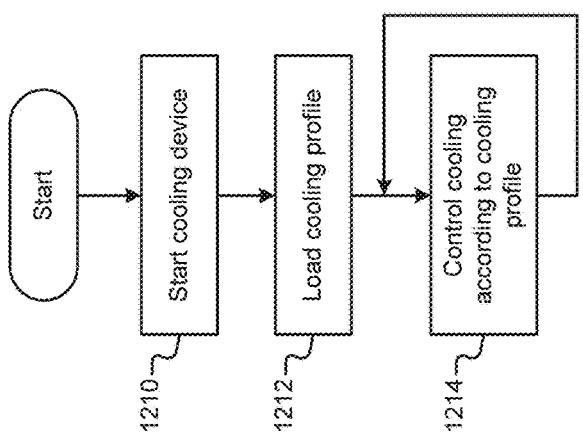
Figure 12A:
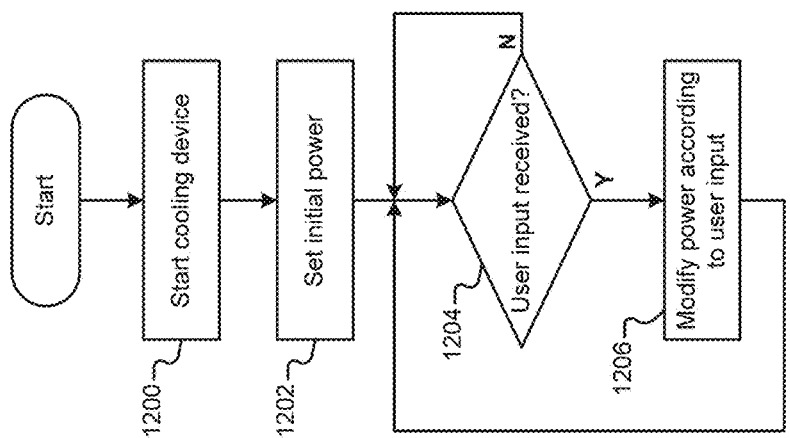
Figure 13:
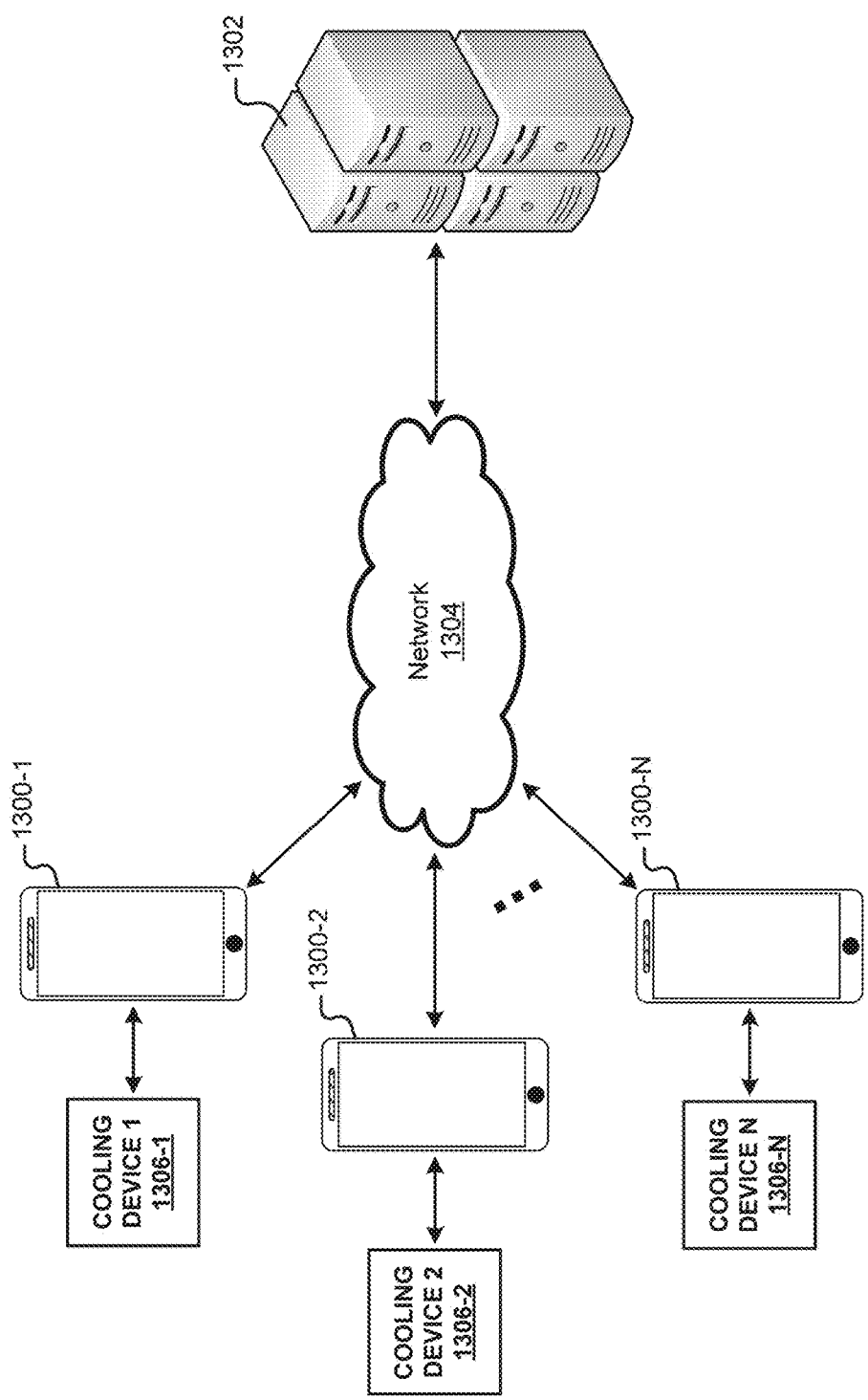
FIG. 13 illustrates communication between a plurality of cooling devices and a remote server.
Figure 14A:
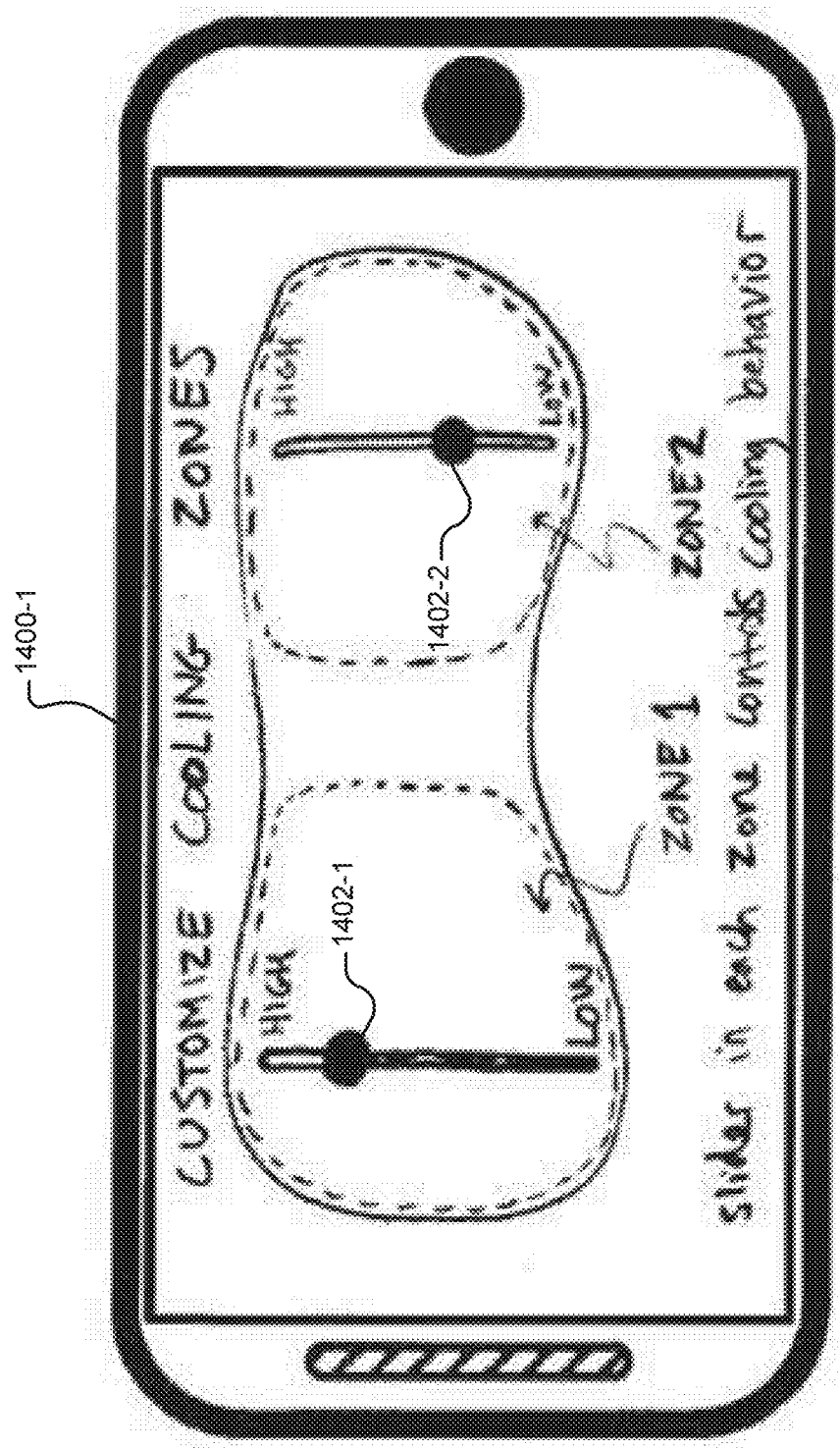
FIGS. 14A-14O illustrate example graphical user interfaces (GUIs) on a user device in communication with a cooling device.

FIGS. 1A-22E illustrate features of example cooling devices 100. FIGS. 1A-1C and 15A-21B illustrate different example cooling device form factors. FIGS. 2A-2E illustrate example cooling units 200. FIGS. 3A-3E illustrate example cooling units 200 connected to other components on a package substrate, such as device electronics and a battery. FIG. 4 illustrates example package substrate shapes that may include cooling units 200 and device electronics. FIGS. 5A-5D illustrate example cooling unit fabrication steps. FIGS. 6A-6D illustrate example flexible cooling units. FIGS. 7A-7K illustrate example layouts for thermal reservoir material and insulation material. FIGS. 8A-8C illustrate example connections between the device electronics, battery, and cooling units. FIG. 9 illustrates communication between a cooling device 100 and a user device 104. FIG. 10 is an example functional block diagram of a cooling device. FIGS. 11A-11E illustrate example cooling profiles that may run on a cooling device 100. FIGS. 12A-12C illustrate example methods describing different cooling device modes of operation. FIG. 13 illustrates a plurality of cooling devices in communication with a remote server via a plurality of user devices. FIGS. 14A-14O illustrate example GUIs on a user device that the user may interact with in order to control/monitor the cooling device 100. FIGS. 22A-22E illustrate example sleeves and garments that may hold the cooling devices 100.

Figure 1B:
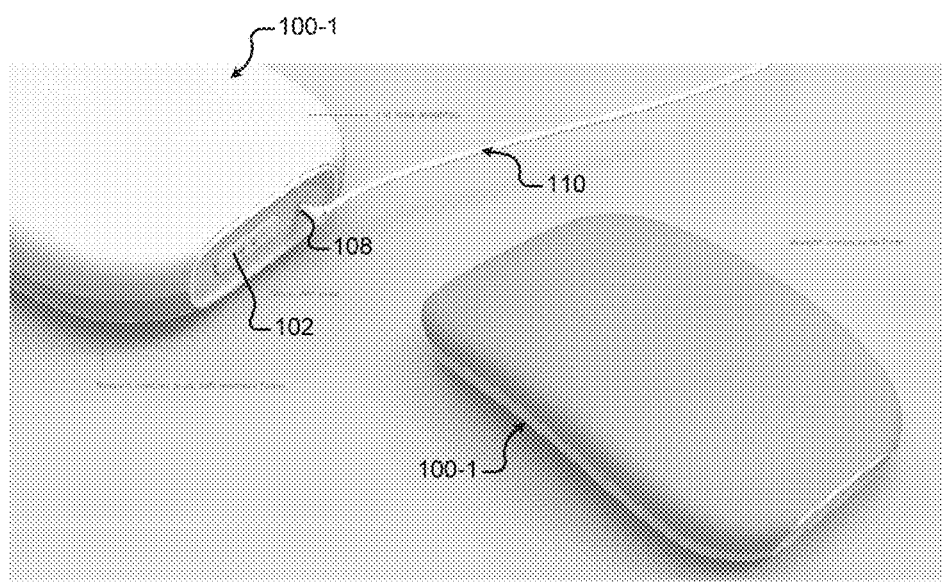
Figure 1C:
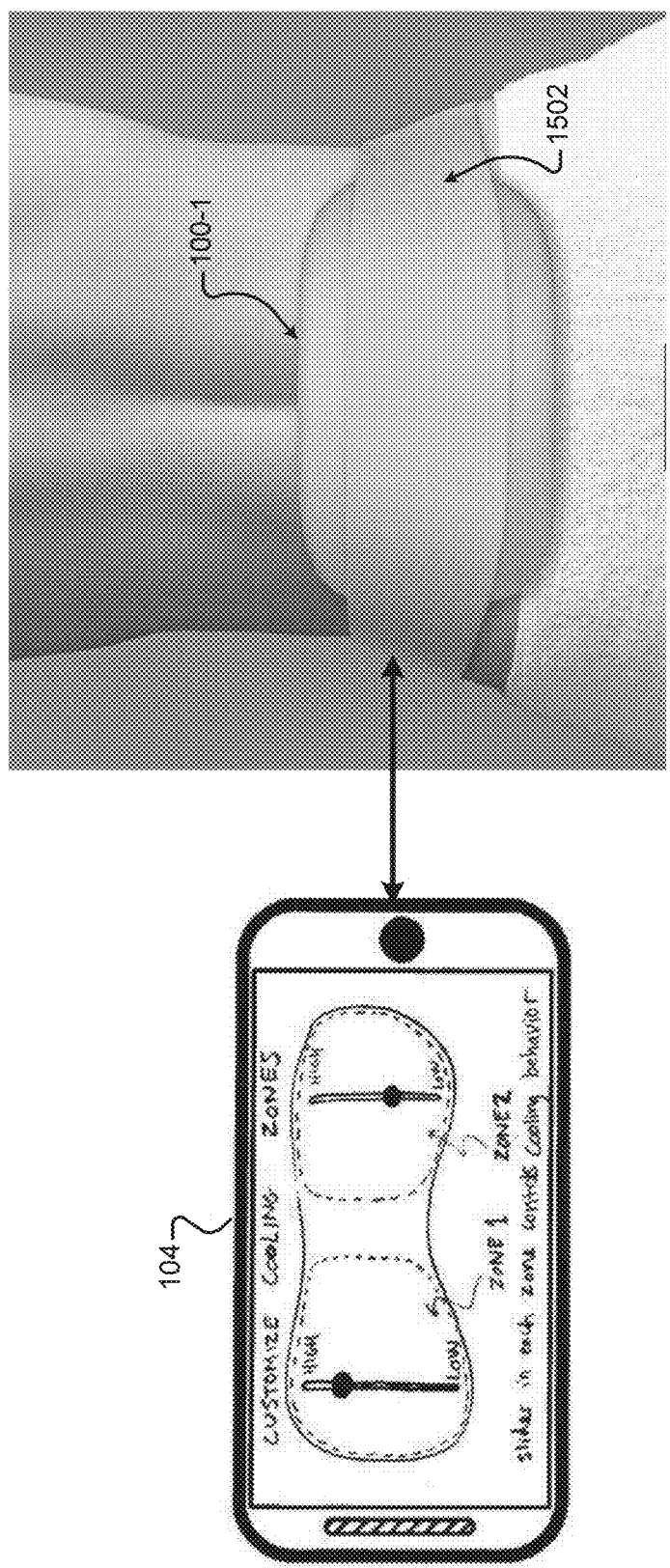

FIGS. 1A-1C illustrate a first example cooling device 100-1 (i.e., the "first cooling device 100-1") that may include one or more cooling units 200. One side of the cooling device 100-1 (the "cold side 106-1") may cool the user during operation. The other side of the cooling device 100-1 (the "hot side 106-2") may expel heat during operation. The one or more cooling units may be arranged in the device package such that the cold side of the cooling units are along the cold side 106-1 of the cooling device 100-1. In some implementations, the cold side of the cooling units may be separated from the user by a package substrate and/or other layers of device packaging (e.g., an encapsulation bottom cover illustrated at 1504-2 in FIG. 15B).

The first cooling device 100-1 includes a user input button 102 and power input port 108. In FIG. 1B, a power cable 110 is plugged into the power input port 108. In FIG. 1C, a user is controlling/monitoring the cooling device 100-1 using a user device 104. For example, the user may control the cooling device 100-1 to cool at different intensities in different cooling zones using the GUI illustrated in FIG. 1C. The example cooling device of FIGS. 1A-1C may have dimensions of approximately 20×10 cm, although cooling devices having different sizes and shapes may be fabricated.

Figure 2C:
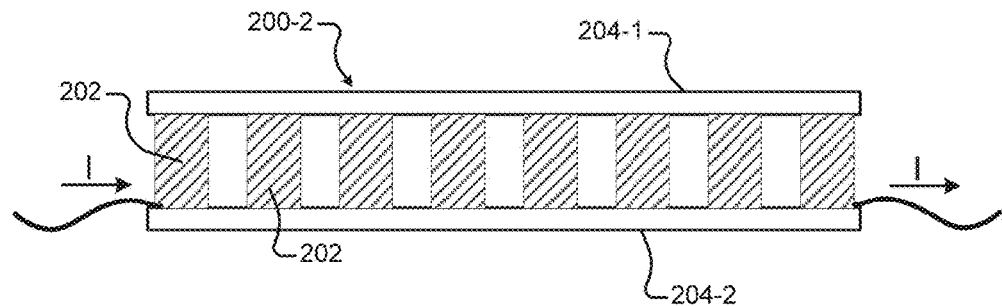

FIGS. 2A-2E illustrate example cooling units 200. FIGS. 2A-2B show a generically illustrated cooling unit 200-1 that may represent any of the variety of cooling unit technologies that may be implemented in a cooling device 100 of the present disclosure. The cooling unit 200-1 of FIGS. 2A-2B includes a variety of cooling unit components that may vary, depending on how the cooling unit 200-1 is constructed. The cooling unit 200-1 includes a first cooling unit substrate 204-1, a second cooling unit substrate 204-2, and cooling unit elements 202 (referred to herein as "cooling elements 202") arranged between the first and second cooling unit substrates 204-1, 204-2 (collectively "cooling unit substrates 204"). In the general cooling unit 200-1 of FIGS. 2A-2B, the hashed region represents the location of the cooling unit elements 202. The first and second cooling unit substrates 204 may be formed from a variety of different materials, such as flexible materials or rigid materials (e.g., ceramics). The cooling unit substrates 204 may provide mechanical support for the cooling unit 200-1. The cooling unit elements 202 may be formed from a semiconductor material such as a Bismuth Telluride alloy. The cooling units 200 may also include electrical interconnects (e.g., metal interconnects) between the cooling elements 202 (e.g., that connect the cooling elements in series). In some implementations, the interconnects can be embedded in the cooling unit substrates 204 or deposited on the cooling unit substrates 204. In other implementations (e.g., FIG. 6B), the electrical interconnects can be included as a separate layer of material (e.g., a connector strip) to which the cooling unit substrates are attached. As described herein, the second cooling unit substrate 204-2 may be referred to as the cold side of the cooling unit, which may be applied to the user's body, as illustrated in FIG. 2B.

Figure 2D:
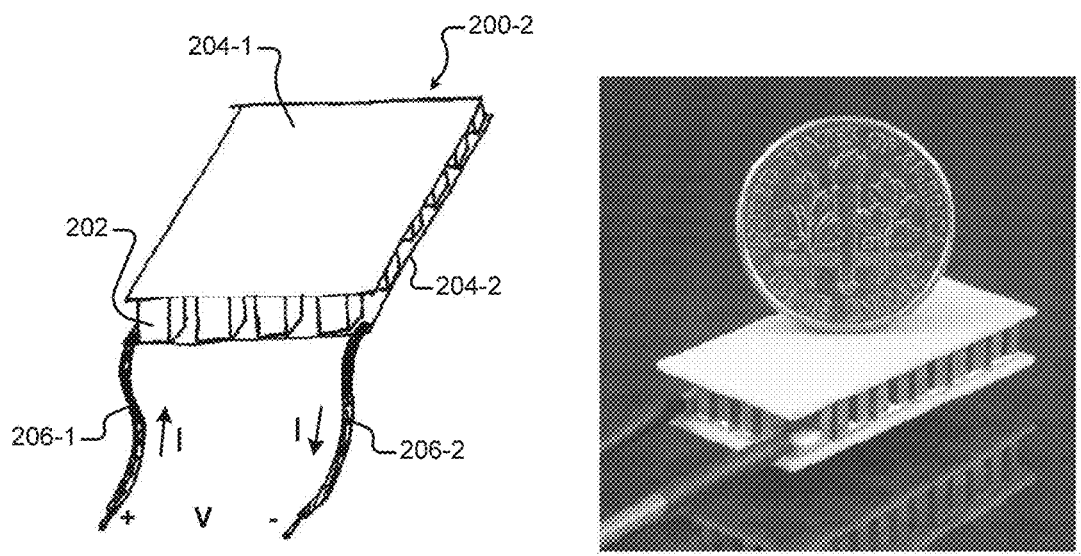
Figure 2E:
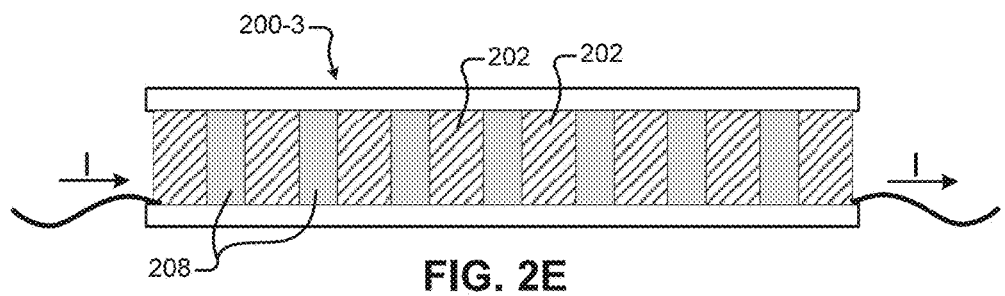
Figure 3A:
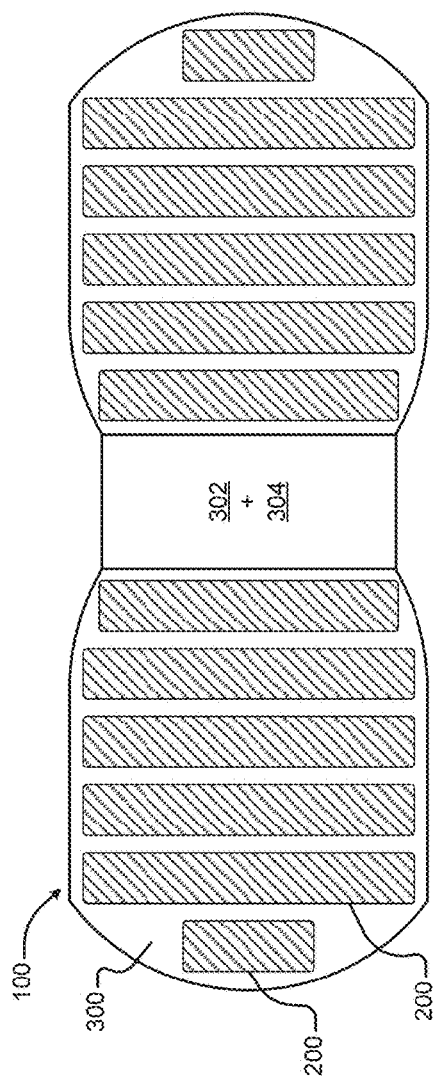
FIGS. 3A-3E illustrate example cooling units, device electronics, and a battery connected to a package substrate.
Figure 3B:
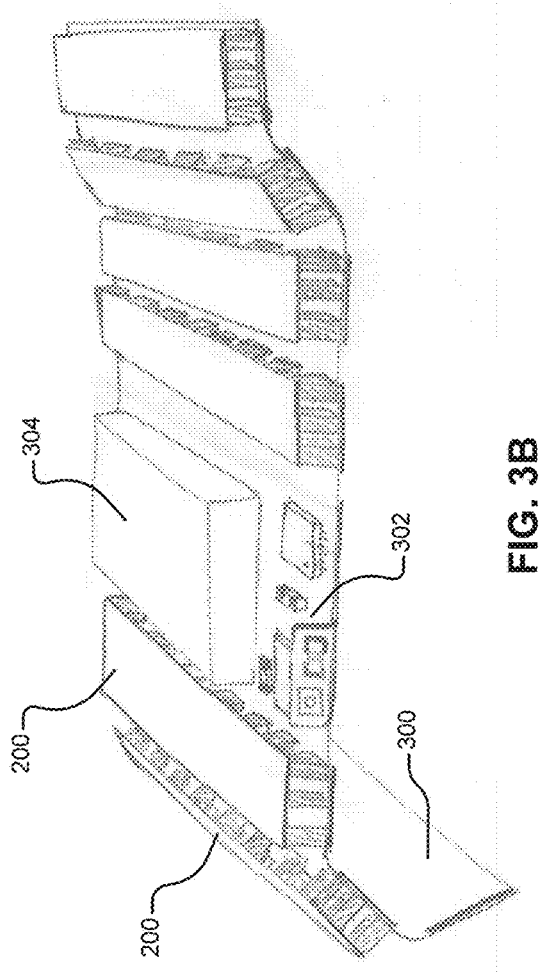

FIGS. 2C-2E illustrate example cooling units 200-2 and 200-3. The example cooling units of FIGS. 2C-2E may represent a thermoelectric/Peltier device. FIG. 2C is a cross sectional view of the thermoelectric/Peltier device. The line drawing of FIG. 2D is a perspective view of the thermoelectric/Peltier device. The photograph of FIG. 2D is a thermoelectric/Peltier device having model number 03511-5L31-03CFL, available from Custom Thermoelectric, Inc. Bishopville, Md., U.S.

The devices of FIGS. 2C-2E include cooling unit elements 202 sandwiched between two cooling unit substrates 204. The thermoelectric/Peltier devices may include semiconductor cooling elements (e.g., Bismuth telluride semiconductor material) and ceramic substrates. As described herein, the cooling unit substrates 204 may be rigid or flexible. In the specific example of the thermoelectric/Peltier device of FIG. 2D, the cooling unit substrates 204 may be rigid ceramics. Although rigid ceramic substrates may be used in other cooling units of the present disclosure, in other implementations, the cooling unit substrate may include flexible materials, such as flexible polymers, flexible silicones, and/or flexible foams. Although the specific thermoelectric/Peltier device of the photograph, model 03511-5L31-03CFL, has rectangular dimensions of approximately 15 mm by 30 mm with a thickness of approximately 5.1 mm, the cooling units may be fabricated in a variety of different dimensions (e.g., 1-10 cm in length/width).

FIG. 2E illustrates an example cooling unit 200-3 including insulation material 208 between the cooling elements 202. The insulation material 208 may electrically and thermally insulate the cooling elements 202 from one another. The insulation material 208 between the cooling elements 202 may reduce thermal losses within the cooling unit 200-3 (e.g., radiative and convective heat transfer from the hot-to-cold sides inside the cooling unit). The insulation material 208 may include, but is not limited to, flexible or rigid foams, soft or hard urethanes and polymers, or silicones of varying durometer. The insulation material 208 can be electrically and thermally insulating.

FIGS. 3A-3E illustrate a variety of different arrangements of cooling device components on a package substrate 300. The package substrate 300 of FIGS. 3A-3D include device electronics 302 and a battery 304 that are centrally located on the package substrate 300. The device electronics 302 and battery 304 are offset to one side of the package substrate 300 of FIG. 3E. The device electronics 302 may be fabricated onto the package substrate 300 or separate from the package substrate 300, such as on a board separate from the package substrate 300 (e.g., a printed circuit board) and/or fabricated onto the cooling unit substrates 204. The device electronics 302 may be secured within the package using a variety of techniques, such as with an adhesive and/or using fasteners (e.g., thread or another mechanical device). The battery 304 and device electronics 302 can be located in other locations on the package substrate 300 or in another location within the device package (e.g., on a separate printed circuit board). The battery 304 and device electronics 302 can be colocated or located apart from one another. In some implementations, the battery 304 can be located externally on the cooling device 100 and/or detachable from the cooling device 100.

The cooling units 200 can be fabricated in a variety of different shapes and sizes. The cooling units 200 may also be arranged on the package substrate 300 in a variety of different arrangements. In FIG. 3A, the cooling units 200 have a rectangular shape and are arranged parallel to one another. Such an arrangement of cooling units 200 may allow the package substrate 300, and the whole cooling device 100, to be flexed between the cooling units 200 to the extent that the package substrate 300 is flexible. FIG. 3B illustrates a perspective view of a cooling device having a similar layout to that of FIG. 3A. In FIG. 3B, the cooling device is flexed (e.g., rolled) in portions of the package substrate 300 between the cooling units 200.

Figure 3C:
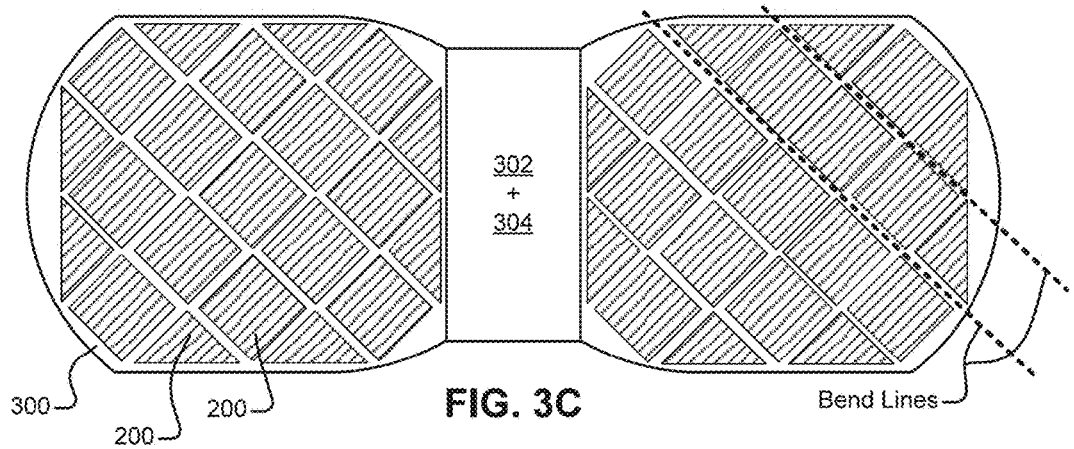
Figure 4:
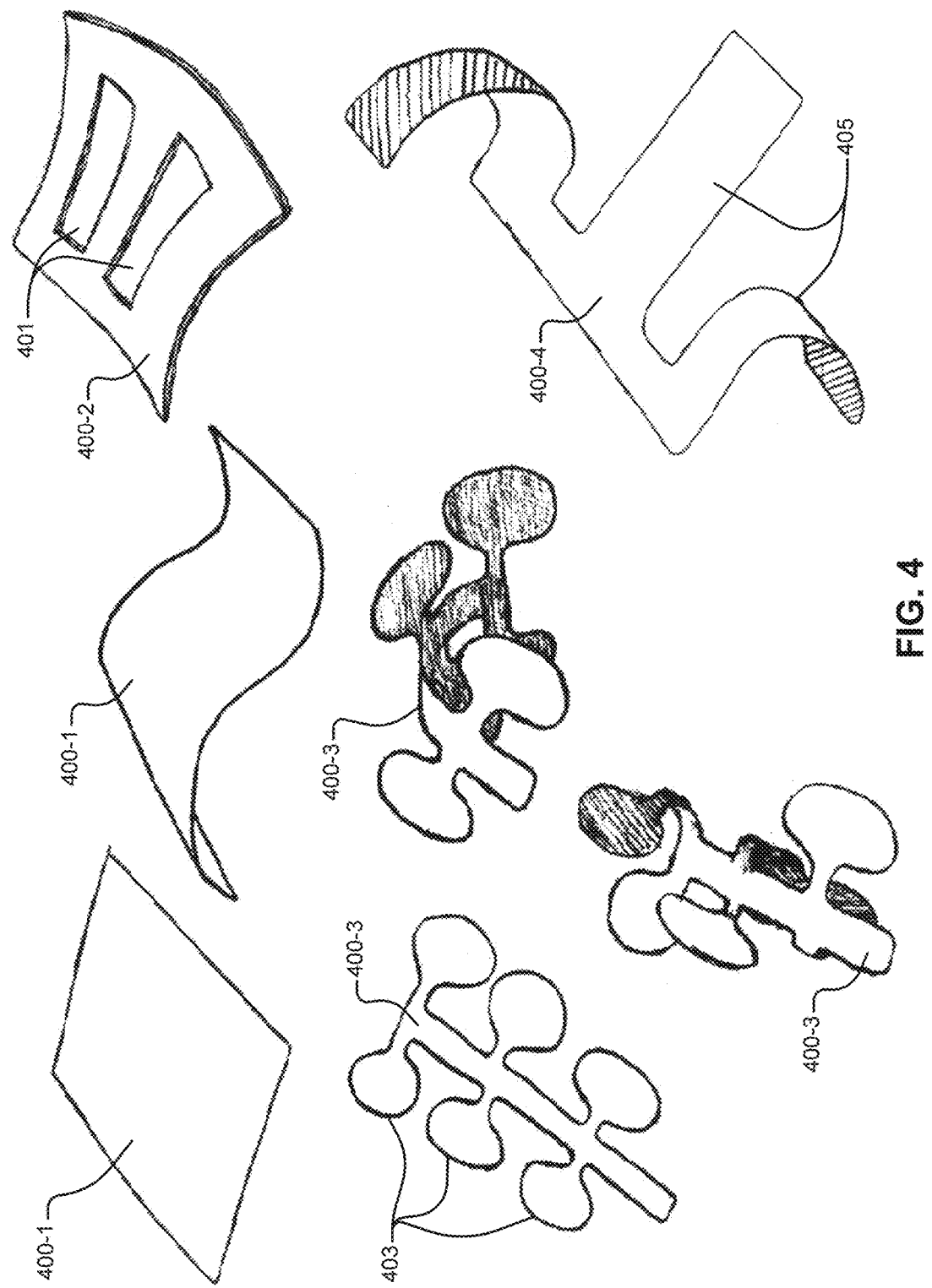
FIG. 4 illustrates example package substrates.

FIG. 3C illustrates a package substrate 300 including different shaped cooling units 200. Specifically, the package substrate 300 includes a plurality of square-shaped cooling units 200 and a plurality of triangle-shaped cooling units 200. The different shaped cooling units 200 may be arranged to better cover the surface of the package substrate 300, thereby providing cooling to a user across more surface area of the portion of the cooling device in contact with the user. The use of smaller cooling units may impart more general flexibility in different directions, even when the cooling units are rigid, because smaller units may be arranged such that more areas of flexible package substrate are available for flexing between the cooling units. In the specific example of FIG. 3C, the cooling device may be flexible along portions of the flexible package substrate 300 between any of the cooling units 200. For example, in FIG. 3C, the cooling device may be bent along any line that extends between the cooling units 200 (e.g., see bend lines of FIG. 3C).

Figure 3D:
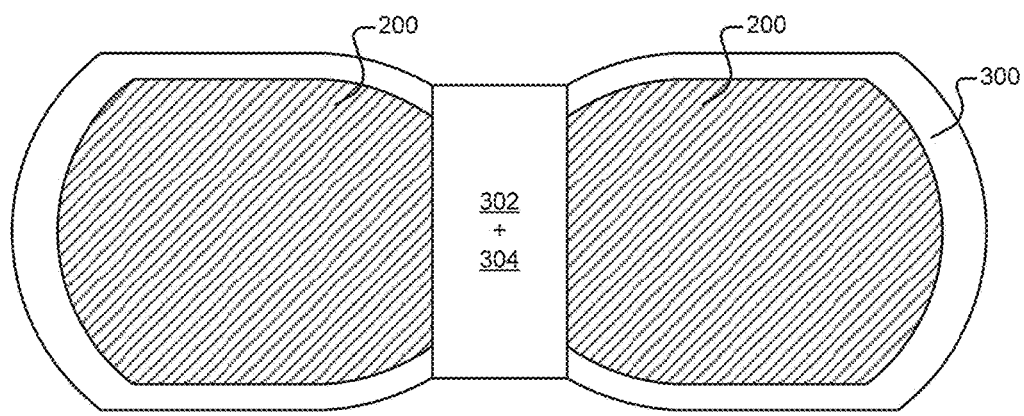
Figure 3E:
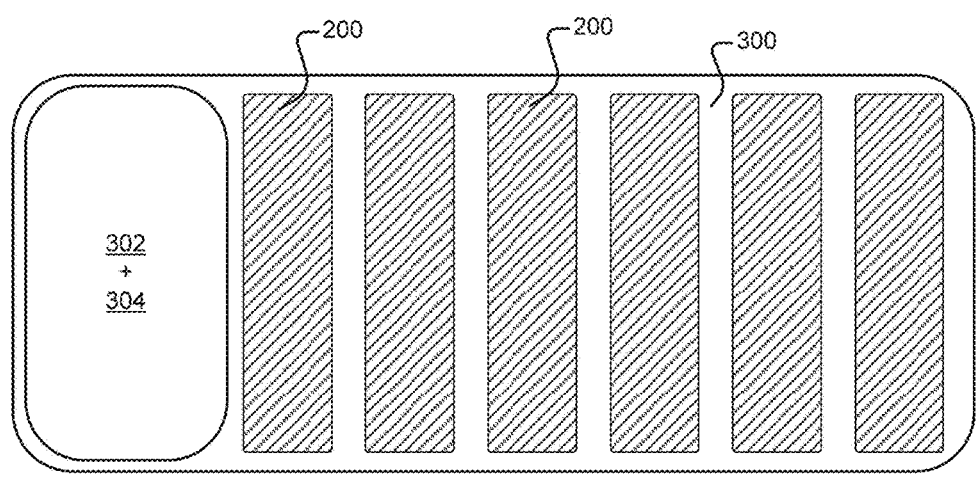

FIG. 3D illustrates a package substrate 300 including two cooling units 200. Each of the cooling units 200 is larger than those illustrated in other figures (e.g., FIG. 3A, FIG. 3C, and FIG. 3E). The larger cooling units 200 of FIG. 3D are shaped to conform to the edges of the package substrate 300. In some cases, a larger cooling unit may provide a more consistent cooling over a larger area than in the case where cooling units are separated from one another. FIG. 3E illustrates a rectangular package substrate 300 that includes device electronics 302 and a battery 304 offset towards one edge of the rectangular package substrate 300. The rectangular cooling units 200 are arranged on the rectangular package substrate 300 such that the package substrate 300 may be rolled. In some implementations, cooling units having different shapes than those illustrated in FIGS. 3A-3E may be fabricated. For example, cooling units may be fabricated in other polygonal shapes (e.g., hexagonal shapes of FIG. 8B), circular shapes, or other irregular shapes.

As described herein, the cooling units may be rigid or flexible. In implementations where the cooling units are rigid, the cooling units may be arranged on a flexible package substrate that allows the overall cooling device to be flexible. Flexibility in the package substrate may allow the package substrate, and overall cooling device, to conform to the user's body during use. The entire package substrate may be formed from the same material in some cases. In other cases, the substrate may include portions that are formed from different materials.

In general, flexibility of the cooling device may be increased through the use of flexible cooling units since the cooling device may flex in areas between the cooling units and also in those areas including the cooling units. In implementations where a large portion of the package substrate is covered with a cooling unit (e.g., FIG. 3D), the cooling device can be made flexible through the use of a flexible cooling unit, whereas the cooling device may be rigid if the cooling unit is rigid.

In some implementations, a rigid package substrate can be used to impart rigidity to the overall cooling device. In other implementations, portions of the package substrate can be made rigid, while other portions may be flexible. For example, the package substrate may be made rigid in portions that include the device electronics and/or battery. A flexible portion of the package substrate may be made rigid by reinforcing a portion of the package substrate with additional material and/or different material (e.g., stiffening material and/or stiffening structures). In one specific example, the package substrate 300 of FIG. 3A may be formed from a single piece of flexible material that is made rigid under the device electronics 302 and battery 304. In this specific example, the portions including cooling units may be flexed while the portion of the package substrate under the device electronics and battery remain rigid.

In some implementations, the cooling device 100 may be configured such that the cooling units 200 are controlled independently from one another. In these implementations, each cooling unit 200 may be electrically coupled to the device electronics 302 using separate electrical connectors. The device electronics 302 may provide power to each of the cooling units 200 independently of other cooling units 200 via the separate electrical connectors. The cooling device 100 may provide more granular cooling in implementations where the cooling units 200 are independently controlled.

In some implementations, the cooling device 100 may be configured such that the device electronics 302 control groups of cooling units 200 together. For example, a group of cooling units 200 may be electrically coupled to one another so that the device electronics 302 controls the group of cooling units 200 together (e.g., via a single pair of wires). In these implementations, the control of cooling may be less granular than independent control of the cooling units 200, however, the wiring layout and control scheme may be simplified in some respects.

As described herein, the overall shape and flexibility of the cooling device 100 may be fabricated based on where the cooling device 100 is to be used on the body. Additionally, the size, shape, and overall coverage of the cooling units 200 may be selectable. Furthermore, the control techniques for the different cooling units 200 (e.g., individual/grouped) may be selected in order to control the granularity of cooling. Accordingly, a variety of different cooling devices 100 can be fabricated for a variety of different uses according to the present disclosure. For example, cooling devices 100 may be fabricated to conform to different parts of a user's body, such as a user's back, wrist, legs, perineum region, etc. Additionally, a cooling device may be fabricated in an eye-mask shape for migraine headache relief, a knee wrap for knee pain, or neck/shoulder wrap.

FIG. 4 illustrates a variety of different example package substrate shapes 400 and features, such as rectangular package substrates 400-1, a package substrate 400-2 including cutouts 401, package substrates 400-3 including protrusions 403 (e.g., lobes), and a package substrate 400-4 including strips 405. Although not illustrated, the package substrates of FIG. 4 may include cooling units. For example, the cooling units may be attached to the substrate or fabricated onto the substrate. The cooling units may be attached to the package substrate using adhesives, mechanical fastening, mechanical constraint within a pocket/region of the substrate, ultrasonic or heat welding, and other techniques.

The substrates (e.g., package substrates and/or cooling unit substrates) can be formed from any material that is tolerant to the levels of heat/cold generated by the cooling units. In some implementations, the substrates may also be tolerant to heat generated during processing steps used to fabricate the cooling device, although some substrates may not be exposed to elevated temperatures during fabrication, depending on how the cooling device is fabricated. Example materials may include, but are not limited to, polyester, polyimide, and silicone. In some implementations, the substrates may include a single layer of material. In other implementations, the substrates may include multiple layers of material that are bonded to one another or otherwise joined together.

FIGS. 5A-5D illustrate example fabrication steps for fabricating cooling units 200-4, 200-5. FIG. 5A illustrates cooling elements 202 being placed onto an example cooling unit substrate 500. The cooling unit substrate 500 may be either a rigid substrate or a flexible substrate. The cooling unit substrate 500 includes portions for receiving the cooling elements 202. The portions that receive the cooling elements 202 may include electrical conductors 501 (e.g., metal) that electrically couples adjacent cooling elements. In FIGS. 5A-5D, the substrates 500, 502 may be fabricated from flexible printed circuit boards with integrated electrical traces that route current through the cooling elements 202.

The cooling unit substrate 500 of FIG. 5B includes a plurality of cooling elements 202. The cooling elements 202 are electrically coupled to one another via connector strips 503, which may be rigid or flexible. The connector strips 503 may include electrical conductors that electrically couple the cooling elements 202. The connector strips 503 can be connected to the cooling elements 202 prior to attachment to the cooling unit substrate 500 or after the cooling elements 202 are attached to the cooling unit substrate 500. The connector strips 503 may be fabricated from flexible circuit board material (e.g., a polyimide material) that includes pads connected by conductive traces. In some implementations, the connector strips 503 may include a metallic material (e.g., copper) or be formed completely from a metallic material. Instead of using individual connector strips, in some implementations, the cooling elements 202 may be connected using a single continuous sheet of flexible circuit board material including traces that electrically connect the cooling elements 202 of the cooling unit. Note that the cooling unit substrate 500 also includes sensors 504 (e.g., temperature sensors) in addition to the cooling elements 202.

The cooling unit can have electrical connectors that electrically couple the cooling unit to the device electronics. In some implementations, the electrical connectors can include metal traces on the cooling unit substrate material. Such connectors can be included on a flexible strip of substrate material (e.g., at 505) that is continuous with the portion of the cooling unit substrate including the cooling elements, as illustrated in FIGS. 5A-5D. In other implementations, the cooling unit substrates can include electrical contacts (e.g., metal pads) that can connect to wires (e.g., be soldered to wires), which are in turn connected to the device electronics.

FIGS. 5C-5D illustrate fabrication of another cooling unit 200-5. In FIG. 5C, the cooling elements 202 are being placed onto the cooling unit substrate 502-1. The cooling unit substrate 502-1 of FIG. 5C includes a top cover 502-2 that includes electrical contacts 506 for electrically coupling the cooling elements 202 to one another (e.g., in a similar manner as the connector strips 503 in FIG. 5B). The top cover 502-2 may be folded over on top of the bottom cooling unit substrate 502-1 at the flexible ribbon portion 507 between the top cover 502-2 and the bottom cooling unit substrate 502-1. The fabricated cooling unit 200-5 is illustrated in FIG. 5D. Note that the top cover 502-2 includes a sensor 508 (e.g., a temperature sensor).

Figure 6A:
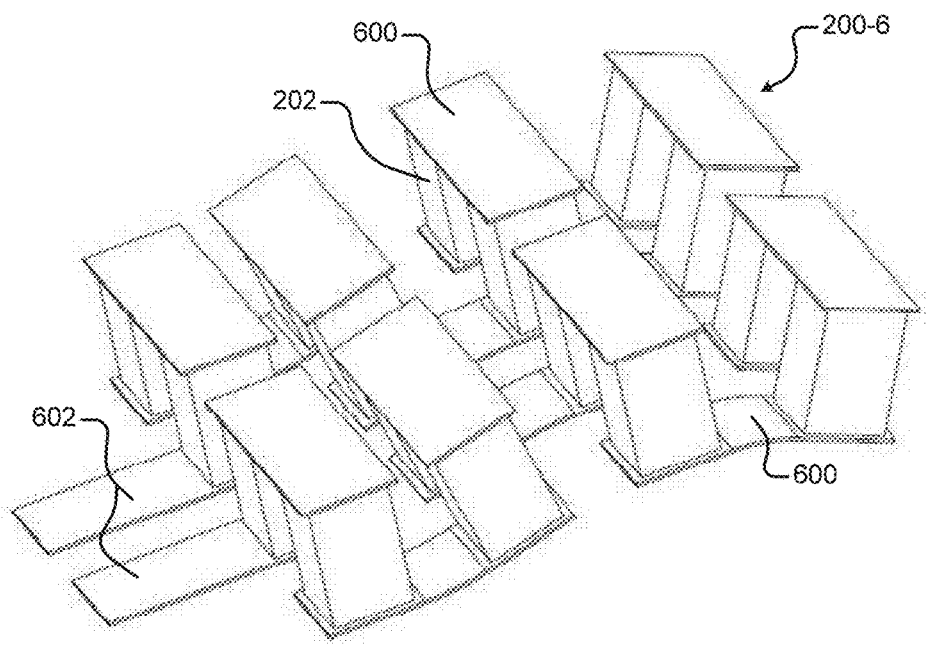
FIGS. 6A-6D illustrate example cooling units.
Figure 6B:
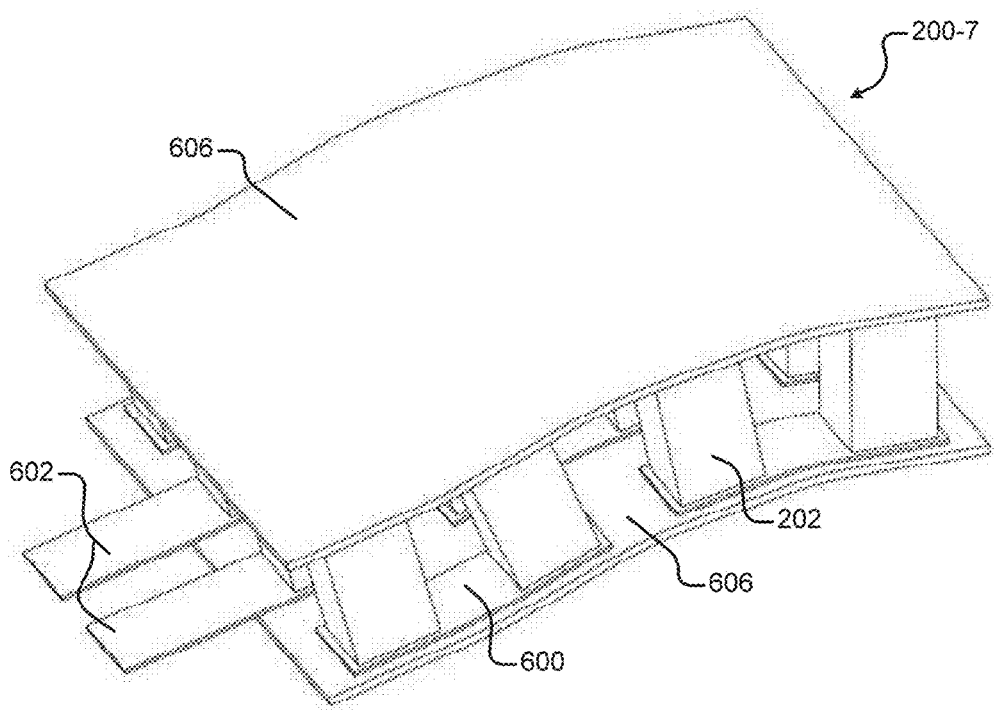
Figure 6C:
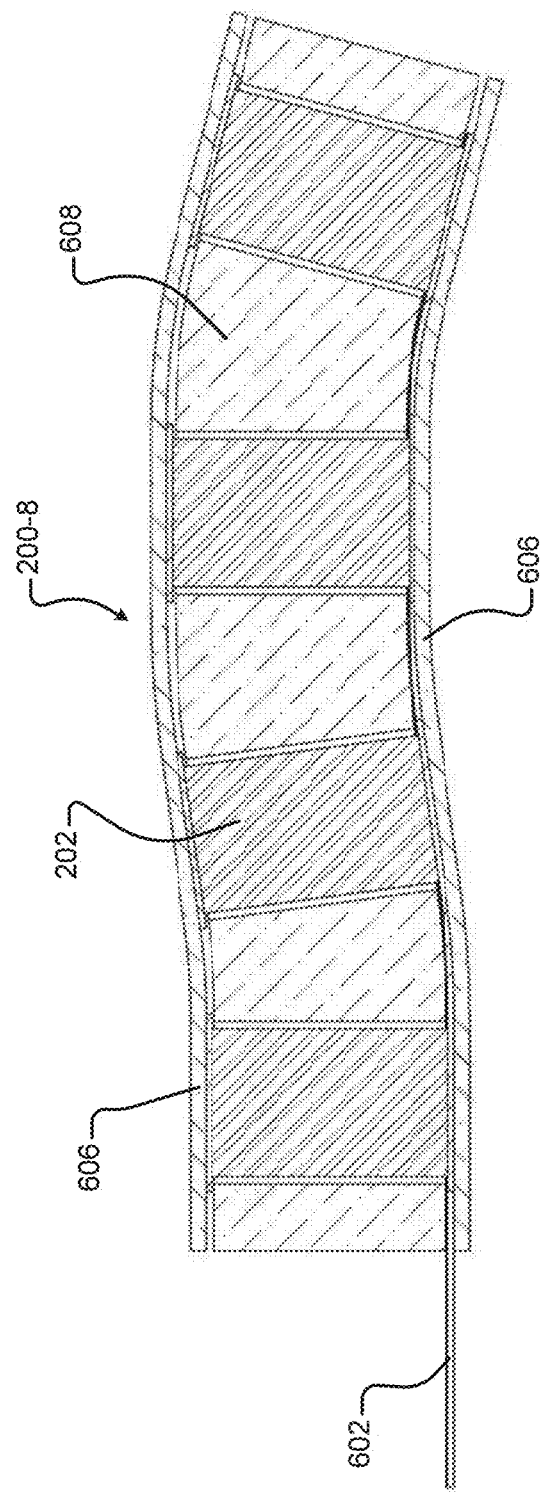
Figure 6D:
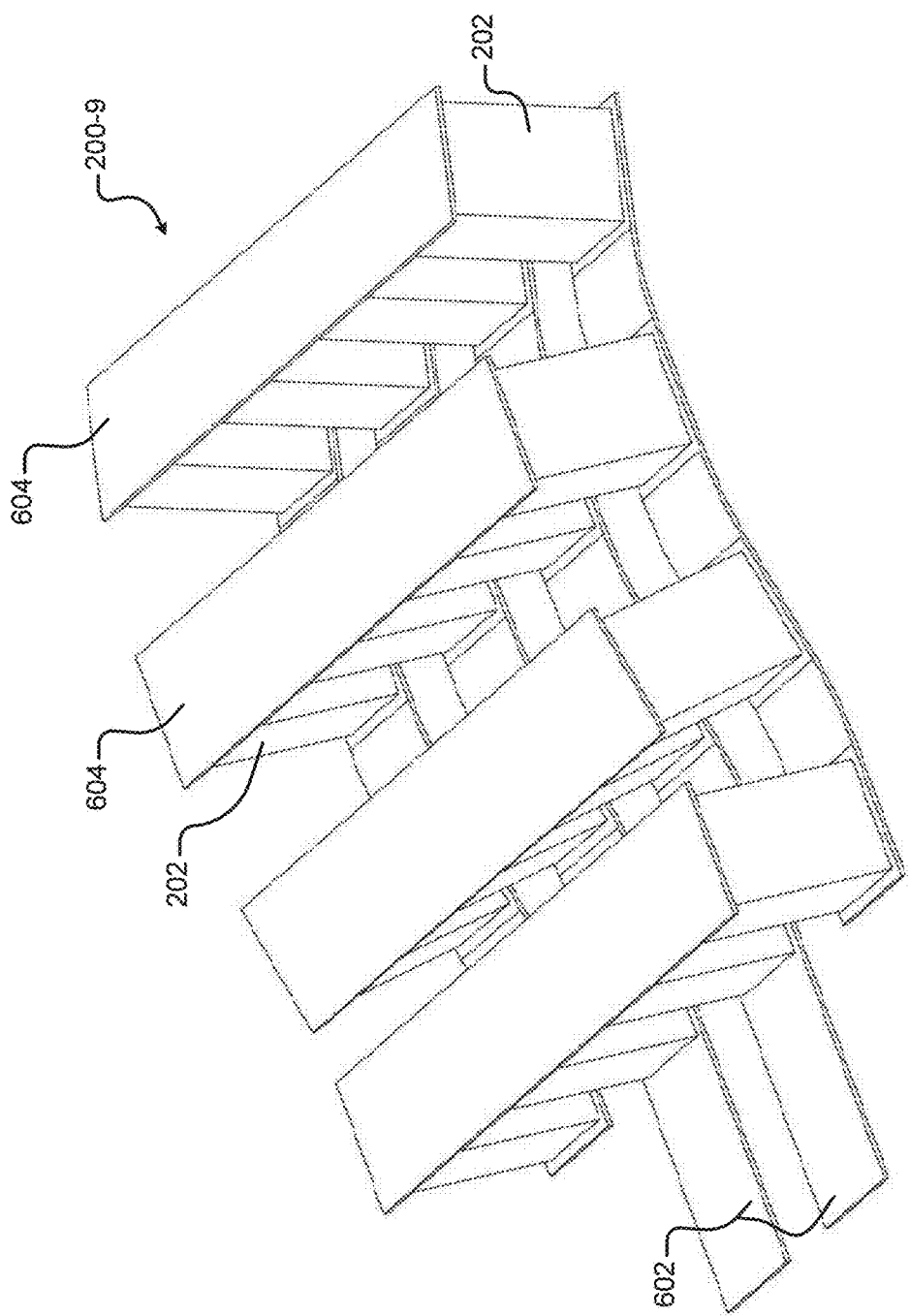

FIGS. 6A-6D illustrate example flexible cooling units 200-6, 200-7, 200-8, 200-9. In FIG. 6A, the cooling unit 200-6 includes cooling elements 202 that are connected to one another by flexible connector strips 600. The flexible connector strips 600 allow the cooling device 200-6 to be flexed in multiple directions, as illustrated in FIG. 6A. The cooling unit 200-6 includes electrical contacts 602 on flexible connector strips that may be connected to the device electronics. FIG. 6D illustrates another example cooling unit 200-9 including connector strips 604. The connector strips 604 of FIG. 6D span more than two cooling elements 202. Although the connector strips 604 of FIG. 6D are attached to additional cooling elements relative to FIG. 6A, the connector strips 604 of FIG. 6D may electrically couple the cooling elements 202 in the same manner as FIG. 6A. The longer strips 604 may simplify fabrication of the cooling unit 200-9 (e.g., using fewer parts) while maintaining mechanical flexibility.

The cooling unit 200-7 of FIG. 6B includes flexible cooling unit substrates 606 on both sides of the cooling elements 202. The flexible cooling unit substrates 606 may provide additional support for the cooling unit 200-7. In some implementations, the cooling unit substrates 606 of FIG. 6B may be attached to a package substrate. In other implementations, the cooling elements 202 may be attached directly to the package substrate, which may include portions for receiving the cooling elements 202. In these implementations, the package substrate may include electrical connections that electrically couple the cooling elements 202 to one another.

FIG. 6C illustrates an example cooling unit 200-8 having material 608 deposited between the individual cooling elements 202. The material may be a flexible insulation material, as illustrated in FIG. 6C. The flexible insulation material 608 may serve to prevent contact between neighboring cooling elements, thermally insulate the cold/hot sides during use, and promote rebound to a pre-defined bend configuration. The flexible insulation material 608 may include flexible silicone foams or solids, flexible urethane foams or solids, polymers of varying durometer, and other elastomeric materials.

In some implementations, the cooling elements and device electronics can be fabricated onto a single package substrate (e.g., 300) that supports the device electronics and the cooling elements. In these implementations, the package substrate may act as a cooling unit substrate. In some cases, during fabrication, the package substrate can include additional portions that are folded back over the cooling elements to act as another cooling unit substrate (e.g., similar to FIGS. 5C-5D), thereby forming one or more cooling units from a single sheet of package substrate material. The cooling elements may be arranged to make cooling zones of any geometry (e.g., arranged on the substrates of FIG. 4).

FIGS. 7A-7K illustrate example cooling units that interface with various different thermal reservoirs 700-1, 700-2, ..., 700-6 (generally referred to herein as a "thermal reservoir 700"). A thermal reservoir 700 may refer to a material that acts as a heat sink for the hot side of the cooling units. Example thermal reservoir materials may include phase-change materials, which may be designed to change from solid to liquid at a pre-determined temperature near the average human body temperature. Example phase-change materials may include paraffin, lipids, salt hydrates, and other organic and inorganic materials. An example phase-change material is PCM-0M37P manufactured under the savENRG brand of Arden, N.C. USA. This material may change from a solid to a liquid at approximately 37 degrees Celsius, allowing it to absorb a substantial amount of heat while remaining very close to 37 degrees Celsius. Non-phase-change materials may also be used as a thermal reservoir. Gels and liquids that have a high heat capacity may allow for rapid heat absorption and distribution while maintaining flexibility of the thermal reservoir material. Solid materials may also be used as a thermal reservoir, such as solid metal materials (e.g., metal strips). Solid materials such as brass, bronze, and copper may also have a combination of high density, moderate heat capacity, and high thermal conductivity. Combinations of liquid and solid materials within a thermal reservoir, as well as liquid and phase-change materials may be used to optimize the density, thermal conductivity, and heat capacity. Balancing of these material properties may allow for maximal heat storage on the hot side of the device, thereby allowing for a longer duration of cooling.

A thermal reservoir 700 may interface with the hot side of one or more cooling units 200. In some implementations, the thermal reservoir 700 may be in direct contact with the hot side of the cooling units 200. In other implementations, other materials may be included between the interface of the thermal reservoir 700 and the cooling unit 200, such as a thermal grease or other thermally conductive materials. In some implementations, the thermal reservoir material may be deposited onto the cooling unit substrate such that the thermal reservoir material is adhered to the cooling unit substrate. In other implementations, the thermal reservoir material may be in contact with the cooling unit substrate, but not bonded to the cooling unit substrate. In some implementations, the thermal reservoir material may be encapsulated inside a containment material, such as a thin plastic film. This may be done when using a thermal reservoir material that is a gel, liquid, or phase-change material in order to avoid leakage and flow away from the hot side of the cooling unit. Furthermore, within the containment material (e.g., a containment cell or baffle), there may be a plurality of reservoir materials. In one implementation, a thermal reservoir may include a phase-change material accompanied by water within a containment material. In one specific implementation of this type, a waxy paraffin-based phase-change material may melt as it absorbs heat but will not dissolve within the water. In this implementation, the water may serve to ensure good thermal contact between the cooling unit and the phase-change material. As the material cools, the waxy substance may return to a solid phase, leaving the water in its liquid phase.

Figure 7A:
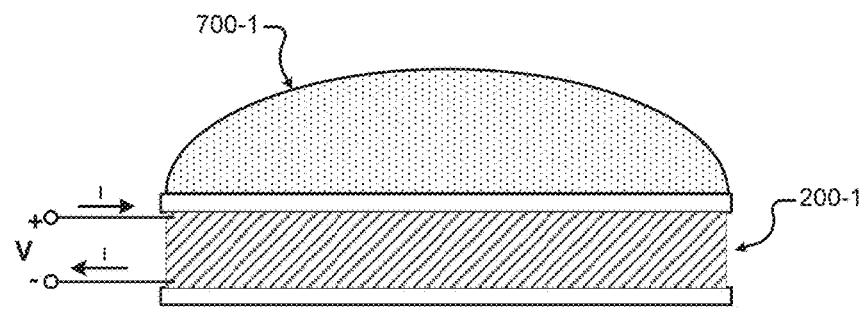
FIGS. 7A-7K illustrate example thermal reservoirs.
Figure 7B:
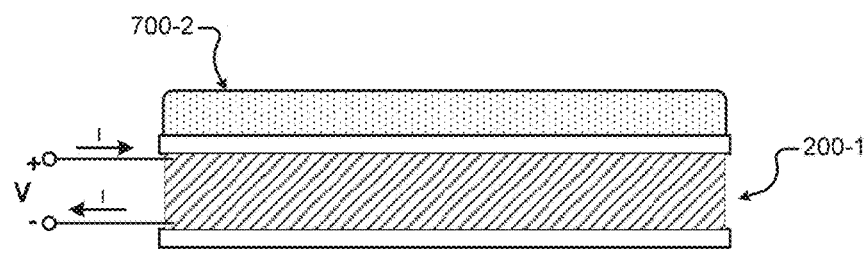

In some implementations, the thermal reservoir material may be deposited over individual cooling units (e.g., FIGS. 7A-7B). In other implementations, a continuous thermal reservoir material may be included over top of a plurality of cooling units (e.g., FIG. 7C). In some implementations, a single thermal reservoir material may be deposited (e.g., in a layer) relatively evenly over the cooling units. In other implementations, multiple layers of thermal reservoir material may be deposited over the cooling units. In some implementations, the thermal reservoir material may be included as distinct depositions over top of individual cooling elements (e.g., FIGS. 7F-7G). Additional thermal reservoir material may be deposited over top of the distinct depositions (e.g., FIGS. 7H-7I).

In some implementations, the thermal reservoir material may be included inside the device package (e.g., not readily removable). In other implementations, the thermal reservoir material may be inserted and removed from the cooling device 100 (e.g., as a removable thermal reservoir package). A removable thermal reservoir material may include a flexible gel pack or assembly of solid materials. In other implementations, the thermal reservoir material may be a liquid, such as water, which may be emptied and refilled by the user. In these implementations, the thermal reservoir material may be removed and replaced.

In some implementations, a cooling device 100 may use an external thermal reservoir to dissipate heat. For example, in implementations where the cooling device 100 is waterproof, a user may dip the cooling device 100 into an external thermal reservoir (e.g., a water bath) or apply an external thermal reservoir (e.g., a water or ice pack) to dissipate heat during use. In one specific example, if the user is wearing a cooling device 100 around their ankle, they may dip their foot and ankle into a water bath to dissipate heat from the cooling device 100. In another example, a user may use their body as a thermal reservoir. For example, a user may place their hand over the hot side of the cooling device 100 to absorb heat and/or sandwich the cooling device 100 between two body parts (e.g., the upper arm and the chest) to cool one body part while heating another.

FIGS. 7A-7B illustrate example thermal reservoirs 700-1, 700-2 deposited on cooling units 200-1. The thermal reservoirs 700-1, 700-2 of FIGS. 7A-7B have different geometries. The thermal reservoir 700-2 of FIG. 7B is smaller than the thermal reservoir 700-1 of FIG. 7A and has a lower profile than that of the thermal reservoir 700-1 of FIG. 7A. The thermal reservoir 700-1 of FIG. 7A is mounded over the hot side of the cooling unit 200-1, whereas the low profile thermal reservoir 700-2 of FIG. 7B is more conformal to the underlying cooling unit substrate.

Figure 7C:
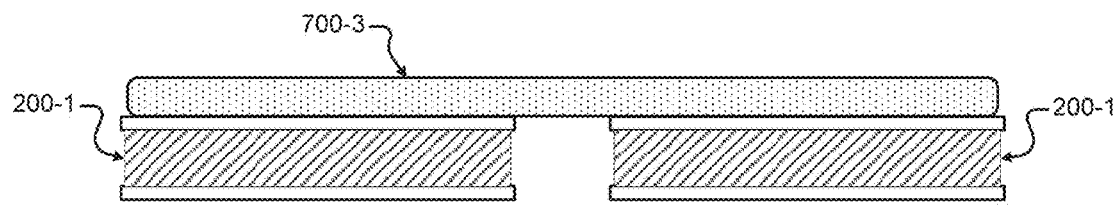

The example thermal reservoir 700-3 of FIG. 7C spans across multiple cooling units 200-1. As such, the single thermal reservoir 700-3 can absorb heat from the multiple cooling units 200-1. Although only two cooling units 700-1 are illustrated in FIG. 7C, a single thermal reservoir may span over more than two cooling units. In some implementations, the same thermal reservoir can span over all the cooling units in the cooling device.

Figure 7D:
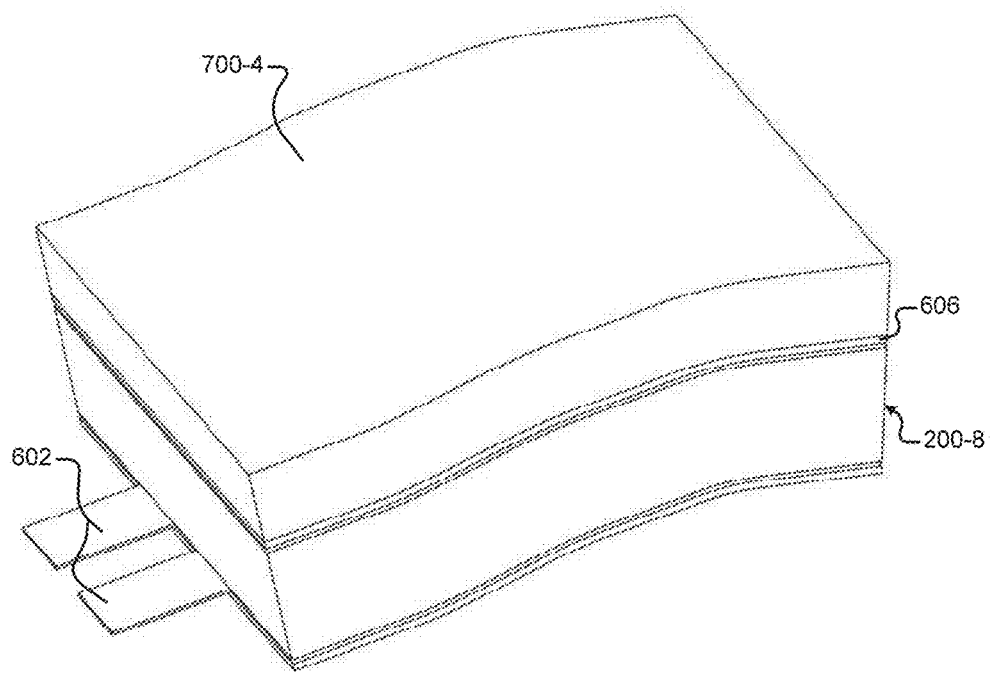
Figure 7E:
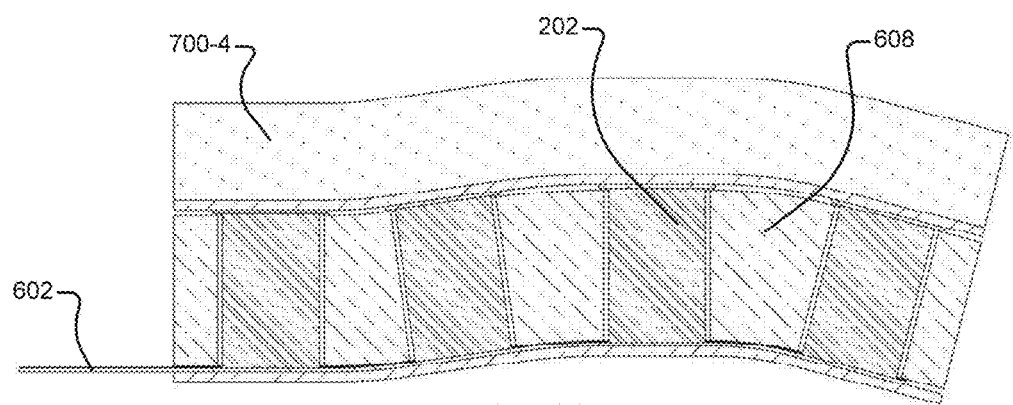

FIG. 7D illustrates a perspective view of a single thermal reservoir 700-4 deposited over top of a single cooling unit 200-8. Note that the thermal reservoir 700-4 may flex along with the underlying cooling unit 200-8. FIG. 7E illustrates a cross-sectional view of the cooling unit 200-8 and thermal reservoir 700-4 in FIG. 7D. The cooling unit 200-8 of FIG. 7E includes an insulation material 608 between the cooling elements 202.

Figure 7F:
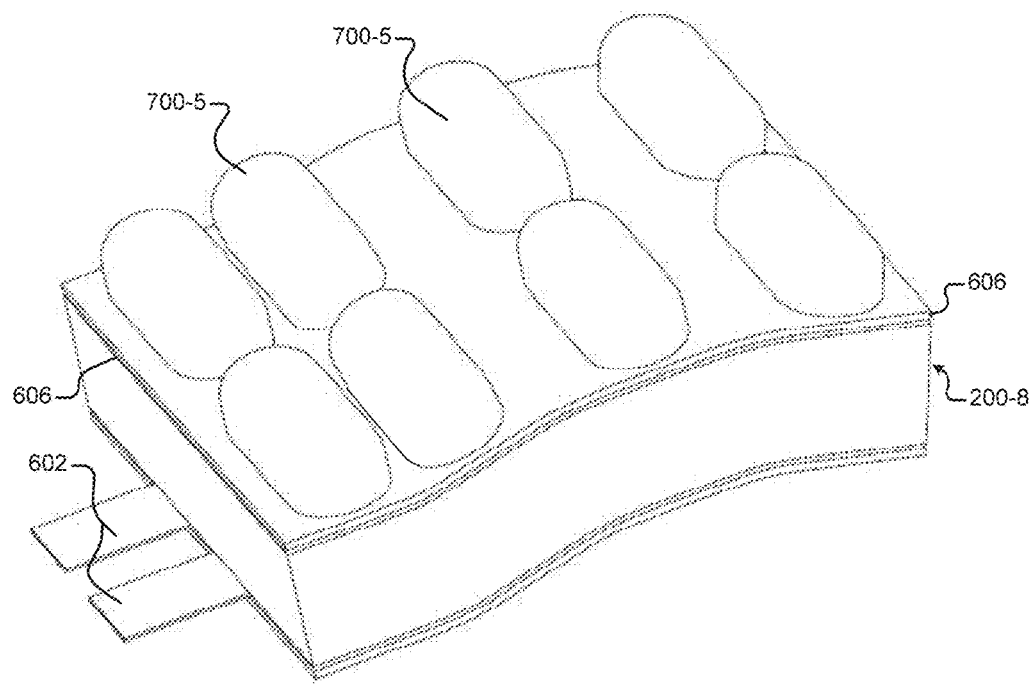
Figure 7G:
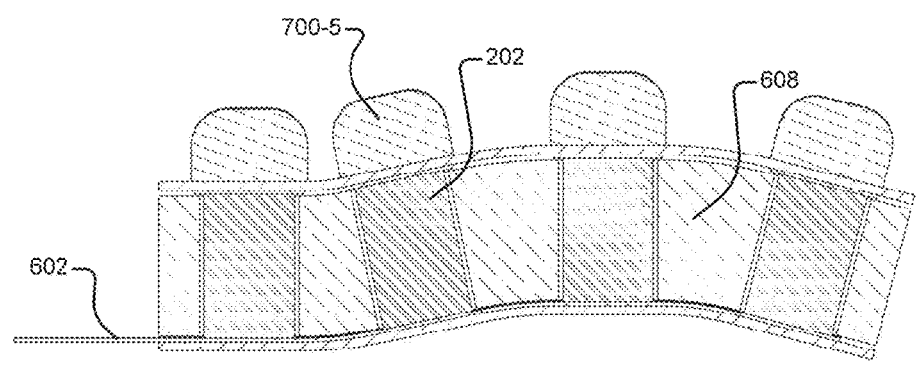

FIGS. 7F-7G illustrate an example cooling unit 200-8 including multiple separate thermal reservoirs 700-5. The distinct thermal reservoirs 700-5 each correspond to a different cooling element 202 or group of cooling elements. For example, the thermal reservoirs 700-5 may be deposited over single cooling elements 202 or groups of cooling elements 202. The thermal reservoirs 700-5 may be bonded to the cooling unit substrate 606. In one implementation, the thermal reservoir 700-5 may comprise a cell made from a thin film of plastic and containing a mixture of phase-change material and a liquid, such as water. In this implementation, the thermal reservoir cell 700-5 may be directly adhered, welded, fused, or otherwise bonded onto the cooling unit substrate 606.

Figure 7H:
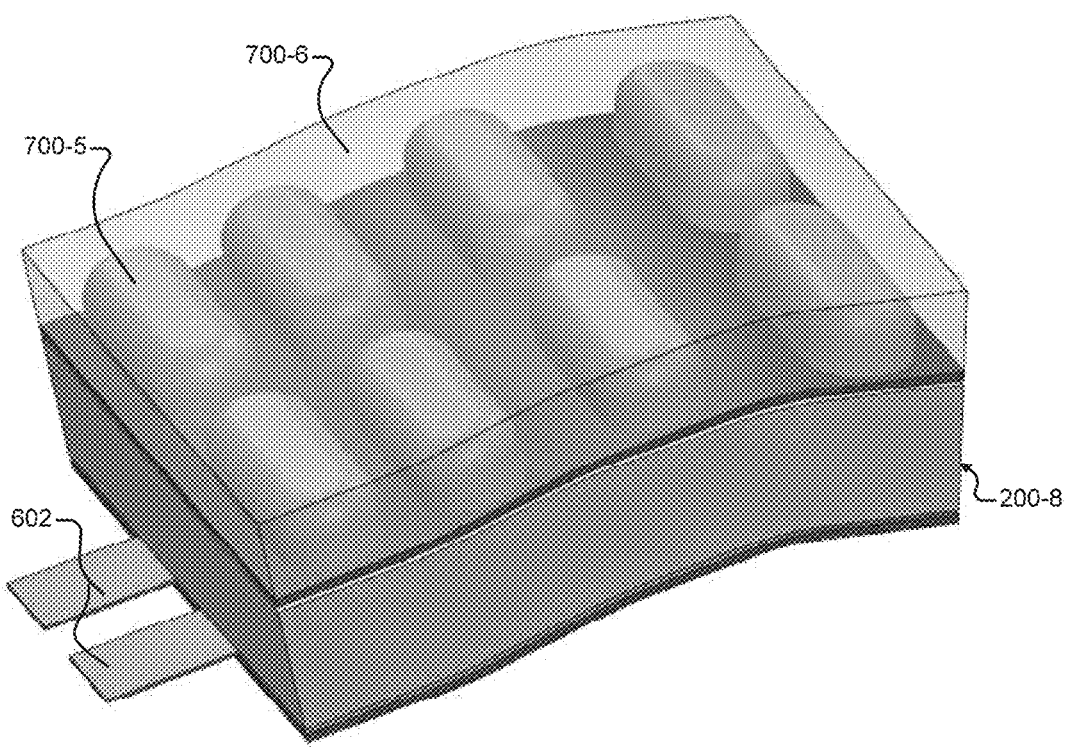
Figure 7I:
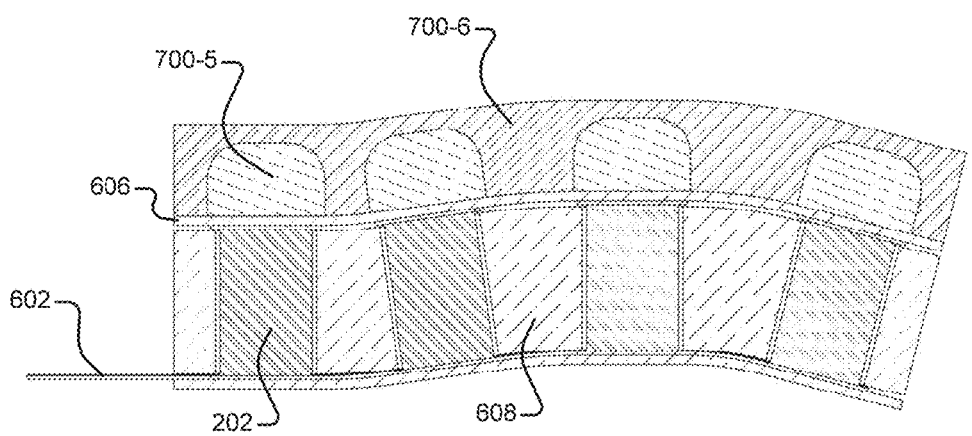

FIGS. 7H-7I illustrate an example cooling unit 200-8 including multiple separate thermal reservoirs 700-5, as described with respect to FIGS. 7F-7G. Additionally, the cooling unit 200-8 of FIGS. 7H-7I include an additional thermal reservoir 700-6 deposited over the separate thermal reservoirs 700-5. The additional thermal reservoir material 700-6 may provide additional heat storage. In some implementations, the additional thermal reservoir material 700-6 may include a gel and/or liquid to provide flexibility. Although two thermal reservoir materials 700-5, 700-6 are illustrated in FIGS. 7H-7I, in other implementations, further thermal reservoir materials may be added. In some implementations, a cooling unit may include multiple flattened layers of different thermal reservoir materials (e.g., multiple layers without the distinct materials deposited in FIGS. 7H-7I).

Figure 7J:
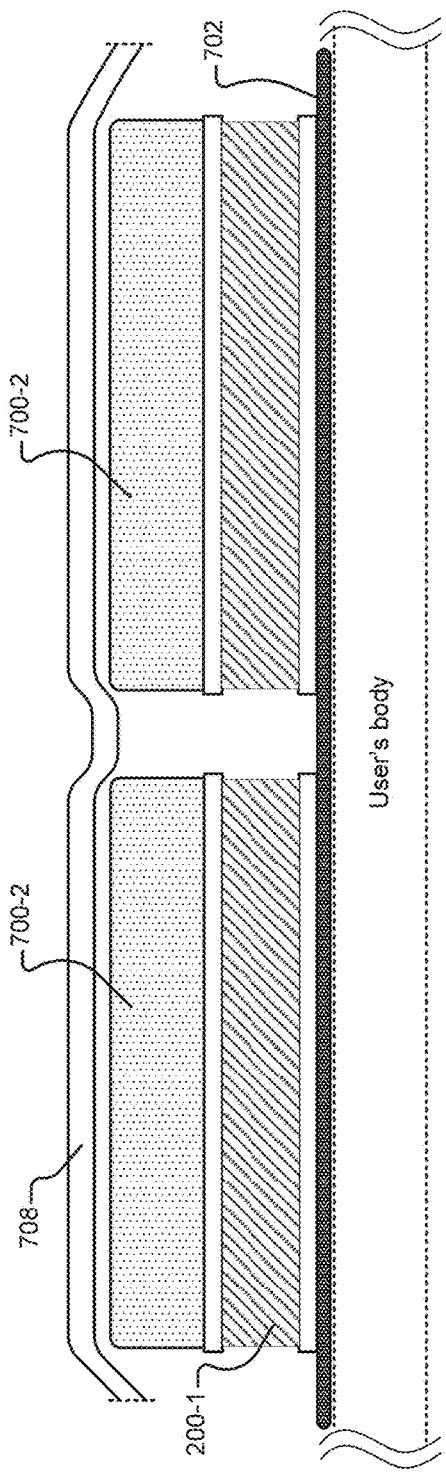
Figure 7K:
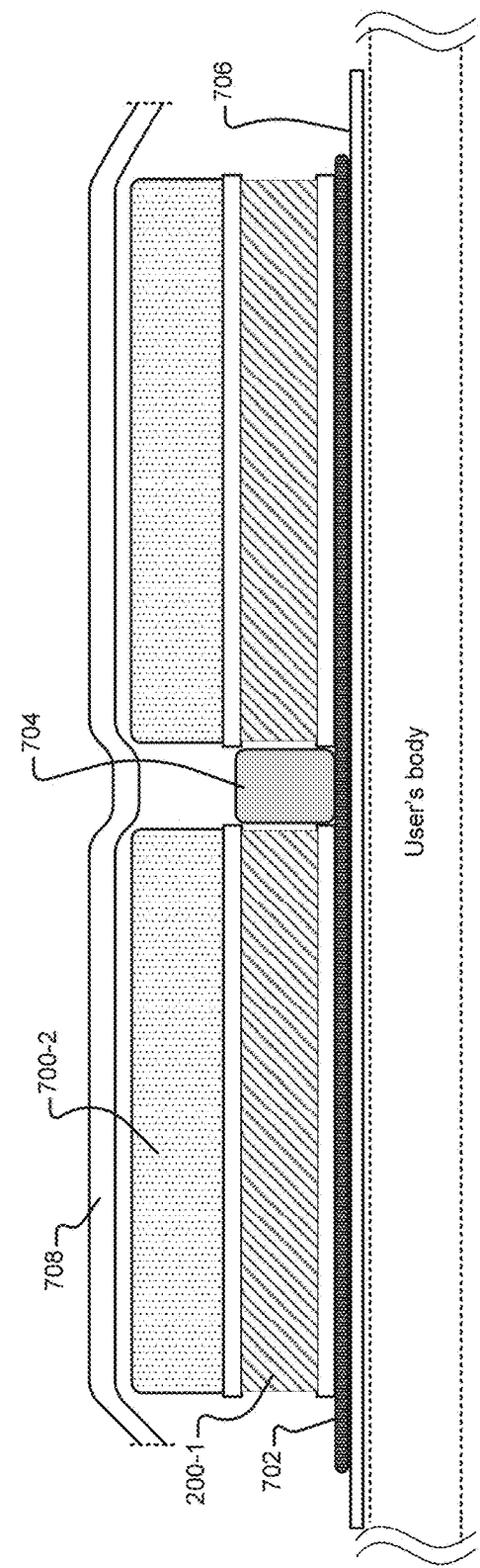

FIGS. 7J-7K illustrate cross sections of two example cooling devices. In FIG. 7J, each cooling unit 200-1 includes a separate thermal reservoir 700-2. The two cooling units 200-1 are attached to a package substrate 702 that interfaces with the user's body. In some implementations, the package substrate 702 may be made from a material with high thermal conductivity, such as copper mesh or an elastomer that has been doped to promote thermal conductivity. The cooling devices also include additional device packaging over top of the thermal reservoirs (e.g., a top encapsulation layer 708). The top encapsulation layer 708 may be formed from material such as fabric (e.g., cloth), polymer, elastomer, or other material. In some implementations, the top encapsulation 708 layer may be omitted. The cooling device of FIG. 7K has a similar structure to that of FIG. 7J, however, the cooling device of FIG. 7K includes an insulating material 704 between the cooling units 200-1. The insulating material 704 may include a flexible foam material. Additionally, the cooling device of FIG. 7K includes an encapsulation bottom layer 706. The encapsulation bottom layer 706 may be made from a flexible material, such as a silicone or a fabric material, in addition to various other materials.

The device electronics 302 control the amount of cooling provided by a cooling unit 200 by controlling the delivery of power to the cooling unit 200. For example, the device electronics 302 may control power delivered to a cooling unit 200 by controlling the voltage applied across the cooling unit 200 (i.e., between two contacts). As another example, the device electronics 302 may control the power delivered to a cooling unit 200 by controlling the current through the cooling unit 200. In some implementations, the cooling device 100 may include maximum power delivery values, such as a threshold power/current/voltage level at which the cooling device 100 may limit the delivery of power to one or more cooling units 200.

The layout of the cooling units defines the cooling zones. In some implementations, the shape of the package substrates can be configured to match the cooling zones. For example, with respect to the package substrate 400-3 of FIG. 4 that includes a plurality of lobes 403, each of the lobes 403 can include one or more cooling units. In this example, each of the lobes may include a cooling zone.

In some implementations, the package substrate (e.g., 300, 400) may include an adhesive layer (not illustrated). The adhesive layer can attach to the package substrate on one surface and adhere to the user's skin on the other surface. The skin adhesive layer may include, but is not limited to, silicone gels, acrylic adhesives, polyurethane gels, and hydrogels. The adhesive layer can include a removable cover layer that may be peeled from the adhesive layer to expose the adhesive layer. The removable cover layer may be a smooth layer that adheres to the underlying adhesive but does not adhere to the user. In some implementations (e.g., FIG. 15D), the adhesive layer 1506 and removable cover layer 1508 may be attached to the outside of the device package instead of the package substrate (e.g., if the package substrate is included under additional layers). In some implementations, the adhesive layer may be removable. For example, the adhesive layer may include an adhesive or other type of attachment for connecting to the package substrate or other portions of the device package. In some implementations, the cooling device may include additional adhesive layers (not shown) used in construction of the cooling device, such as adhesive layers that adhere different package components to one another.

The device electronics 302 can control cooling based on a cooling profile, user input, and/or sensor data (e.g., in the manual/automatic/mixed mode). The device electronics 302 may also perform a variety of other functions described herein. For example, the device electronics 302 can provide communication with the user device 104, control charging of the battery 304, and control interactions with user interface devices (e.g., user input button 102).

The device electronics 302 can be mounted in a variety of different locations. In some implementations, the device electronics 302 can be mounted (e.g., soldered) to the package substrate (e.g., see FIG. 3B). In FIG. 3B, the device electronics 302 are included on a portion of the package substrate 300 that is more rigid than the rest of the package substrate 300. In other implementations, the device electronics 302 may be attached to a flexible portion of the package substrate 300.

Although the device electronics 302 can be mounted to a package substrate including cooling units, in some implementations, at least a portion of the device electronics 302 can be mounted in another location. For example, with respect to FIGS. 8A-8C, the device electronics 302 can be mounted to a printed circuit board 800 (PCB) that is external to the package substrate, but included in the device package. In these implementations, the PCB 800 including the device electronics 302 can be electrically coupled to the cooling units 200 (e.g., via wires that connect the device electronics to the cooling units).

In some implementations, an external PCB 800 can be wired (e.g., permanently) to the cooling units 200. For example, the external PCB 800 can be soldered or otherwise connected to the cooling units (e.g., via wires). In other implementations, as illustrated in FIGS. 8A-8C, the cooling devices can include a cooling unit connector 806 that can electrically couple the external PCB 800 to the cooling units 200. The cooling unit connector 806 can include two connection components 806-1, 806-2 that can be disconnected from one another so that the external PCB 800 and the cooling units 200 can be disconnected from one another. The cooling unit connector 806 can include an electronics side and a cooling unit side. The two sides of the connector 806 can be connected to electrically couple the device electronics 302 and the cooling units 200. The illustrated connector is a low-profile connector, such as a Molex 36877-0004 connector. The connector 806 may have a positive-latching connector design so that the connector 806 does not become detached during use. Additionally, the connector may be water-proof to allow for easy cleaning or moisture exposure during use. In some implementations, the PCB 800 can be connected to the cooling units 200 with other types of detachable connectors than those illustrated. For example, the external PCB may include a socket into which the cooling unit connectors on the package substrate can be inserted, such as a Universal Serial Bus (USB) connection or other low profile power connector. As an additional example, the package substrate may include a socket into which the external PCB wires/connectors can be inserted. The cooling devices may also include a battery connector 805 that can electrically couple the external PCB 800 to the battery 304. The battery connector 805 may be similar in structure to the cooling unit connector 806.

In implementations where the device electronics 302 are detachable from the cooling unit(s) (e.g., via the cooling unit connector 806), different package substrates having different arrangements of cooling units (e.g., layout/number of cooling units) and sensors may be interchangeable with the same device electronics 302. In other cases, a new package substrate with cooling units having the same arrangements as the old package substrate could be swapped out (e.g., in the case the old cooling units are broken or worn out).

FIGS. 8B-8C illustrate how different package substrates 802, 804 having different cooling unit arrangements can be connected to the device electronics 302 via the cooling unit connector 806. In FIG. 8B, the device electronics 302 can connect to a plurality of cooling units 200 and a temperature sensor 808 included on the substrate. In FIG. 8B, the device electronics 302 can deliver power to the cooling units 200 and also determine the temperature indicated by the temperature sensor 808.

In FIG. 8C, the device electronics 302 are connected to a package substrate 804 having a different number and arrangement of cooling units 200. Although the arrangements of cooling units 200 and sensors are different from FIG. 8B, in some implementations, the same device electronics 302 may be configured to operate the cooling units 200 and temperature sensor 808 of FIGS. 8B-8C. For example, the device electronics 302 can be configured to deliver power to the cooling units 200 of FIG. 8B and determine the temperature indicated by the temperature sensor 808 in FIG. 8B. The device electronics 302 can then reconfigure to deliver power to the cooling units 200 of FIG. 8C.

In some implementations, the device electronics 302 can deliver power to the cooling units 200 and measure temperature using the same circuits. For example, if the temperature sensor 808 is a resistive temperature sensor (e.g., a thermistor or resistance temperature detector), the device electronics 302 may include circuits that deliver power to the sensor 808 in a manner similar to the cooling units 202, determine the resistance of the sensor 808, and determine temperature based on the determined resistance. In other implementations, the device electronics 302 may include additional components that interface with the temperature sensor 808, such as circuits that interface with a thermocouple or a digital temperature sensor. The device electronics 302 may include switches (e.g., discrete switches and/or switches included on a microcontroller) that may be used to reconfigure the functionality for each of the electrical contacts provided by the device electronics 302 (e.g., pinouts/wires). The device electronics 302 may be configured to operate while connected to a different number of connections than illustrated.

As described with respect to FIGS. 8B-8C, the device electronics 302 can be configured (e.g., using switches) to couple to sensors and/or cooling units using the same electrical contacts. In some implementations, the device electronics 302 may be configured to operate with a variety of different cooling units having a different number of contacts, different arrangements, and/or different types of sensors. The device electronics 302 may determine how to operate with different cooling units in a variety of different ways. In some implementations, a user may manually configure the device electronics 302 (e.g., using a GUI on the user device 104) to operate with a specific arrangement of cooling units. For example, the user may enter a model number of the package substrate including the cooling units into the GUI that indicates to the user device 104 and/or cooling device 100 how to configure the device electronics 302 for operating the specific cooling units and sensors. In some implementations, the device electronics 302 may automatically detect the specific package substrate and/or cooling units attached to the device electronics 302 and then correctly operate the cooling units. The device electronics 302 may automatically detect the package substrate and/or cooling units in a variety of ways, such as via applying test voltage/current to determine the cooling unit arrangement and whether a sensor is attached. In some cases, a package substrate and/or cooling units may include an identification circuit (e.g., a ROM) that indicates details of the package substrate and/or cooling units to the device electronics 302, such as the number of cooling units, the arrangement of cooling units, and the number/arrangement of sensors. The device electronics 302 may determine the configuration of the package substrate and/or cooling units and how to operate the package substrate and/or cooling units based on communication with the identification circuit (e.g., by reading the ROM). In some implementations, the device electronics 302 may also operate the cooling units based on communication with the battery (e.g., an external battery that may be swapped for another battery). For example, the device electronics 302 may identify battery parameters, such as storage capacity, charge parameters, etc., and control the cooling units based on the identified parameters.

FIG. 9 illustrates a cooling device 100 in communication with a user device 104 (e.g., a cell phone). The device electronics 302 can include wireless/wired communication technology that communicates with the user device 104. As described herein with respect to FIG. 13, the user device 104 can communicate with a remote server 1302 via a network 1304, such as the internet. The user device 104 can also provide a variety of functionality with respect to the cooling device 100. In some implementations, the user device 104 may generate a GUI (e.g., FIGS. 14A-14O) that the user may use to perform a variety of different operations with respect to the cooling device 100. For example, the user may interact with the GUI to control cooling. In some examples, the user may interact with GUI element controls to control cooling. In other examples, the user may select a cooling profile and upload the cooling profile to the cooling device 100 using the GUI. The user may select a profile on the cooling device 100 to run, select a cooling profile from the user device 104 to load onto the cooling device 100, and/or retrieve a cooling profile from a remote server (e.g., see FIG. 10) to run on the cooling device 100. The user may also monitor various cooling device parameters, such as the battery status, the currently running cooling profile (e.g., a cooling map), and the remaining time for which the cooling device 100 may run the cooling profile. Additional features of the user device 104, cooling device 100, and aspects of communication between the devices 100, 104 are described herein.

FIG. 10 is a functional block diagram of an example cooling device 1000. The various modules represent functionality (e.g., circuits and other components) included in the cooling devices 100, 1000 of the present disclosure. Modules of the present disclosure may include any discrete and/or integrated electronic circuit components that implement analog and/or digital circuits capable of producing the functions attributed to the modules herein. For example, the modules may include analog circuits, such as amplification circuits, filtering circuits, analog/digital conversion circuits, and/or other signal conditioning circuits. The modules may also include digital circuits, such as combinational or sequential logic circuits, memory circuits, etc. Memory may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device. Furthermore, memory may include instructions that, when executed by one or more processing circuits, cause the modules to perform various functions attributed to the modules herein. The device electronics of the cooling devices described herein are only example device electronics. As such, the types of electronic components used to implement the device electronics may vary based on design considerations.

The functions attributed to the modules herein may be embodied as one or more processors, hardware, firmware, software, or any combination thereof. Depiction of different features as modules is intended to highlight different functional aspects and does not necessarily imply that such modules must be realized by separate hardware or software components. Rather, functionality associated with one or more modules may be performed by separate hardware or software components, or integrated within common or separate hardware or software components.

The cooling device 1000 includes a processing module 1002 (e.g., a processor and/or microcontroller), a communication module 1004, an interface module 1006, a power module 1008, a cooling control module 1010, and a temperature sensing module 1012. The cooling device 1000 may also include a battery 1014, cooling units 1016-1, 1016-2, . . . , 1016-N, and one or more sensors 1018 (e.g., a temperature sensor). The processing module 1002 communicates with the modules included in the cooling device 1000. For example, the processing module 1002 may transmit/receive data to/from the modules and other components of the cooling device 1000. As described herein, the modules may be implemented by various circuit components. Accordingly, the modules may also be referred to as circuits (e.g., a communication circuit, temperature sensing circuit, cooling control circuit, interface circuit, and power circuit).

The processing module 1002 may communicate with the memory 1020. The memory 1020 may include computer-readable instructions that, when executed by the processing module 1002, cause the processing module 1002 to perform the various functions attributed to the processing module 1002 herein. The memory 1020 may include any volatile, non-volatile, magnetic, or electrical media, such as RAM, ROM, NVRAM, EEPROM, Flash memory, or any other digital media. In some implementations, the processing module 1002 may include a microcontroller which may include additional features associated with other modules, such as an integrated Bluetooth Low Energy transceiver.

The temperature sensing module 1012 is electrically coupled to the temperature sensor 1018. The temperature sensor 1018 indicates the temperature in the area in which the temperature sensor 1018 is located. The temperature sensing module 1012 may determine the temperature in the location of the temperature sensor 1018. In some implementations, the temperature sensor 1018 may generate a temperature signal that indicates the temperature in the area. For example, the temperature sensor 1018 may generate a digital signal that the temperature sensing module 1012 uses to determine the temperature. As another example, if the temperature sensor 1018 is a passive thermistor, the temperature sensing module 1012 may measure a current/voltage generated by the temperature sensor 1018 and determine the temperature based on the measured current/voltage.

The interface devices 1022 may include user-feedback devices and/or user input devices. For example, user-feedback devices may include, but are not limited to, a display (e.g., a touchscreen display), vibration devices, lighting devices (e.g., LEDs), and a speaker. The interface module 1006 can control the user-feedback devices. For example, the interface module 1006 may include display control/driver circuits, vibration control circuits, LED control circuits, speaker control circuits, and/or other control circuits. In some implementations, the processing module 1002 may control the interface devices 1022 via the interface module 1006. For example, the processing module 1002 may generate control signals that the interface module 1006 uses to control the interface devices 1022. For example, the interface module 1006 may include circuits that deliver power/data to the display/vibration/lighting devices, while the processing module 1002 controls the delivery of power/data to the display/vibration/lighting devices.

Example user input devices include, but are not limited to, buttons (e.g., manual buttons and/or capacitive touch sensors), switches, and a touchscreen. The interface module 1006 may include circuits for receiving user input signals from the user input devices. The processing module 1002 may receive the user input signals from the interface module 1006 and take a variety of actions based on the user input signals. For example, the processing module 1002 may detect a user pushing an on/off button and then power up the cooling device 1000 in response to detection of the press. As another example, the processing module 1002 may detect a user pressing a cooling control button (e.g., +/− buttons) and then increment/decrement the amount of cooling provided by the cooling units 1016 based on detection of the press.

The communication module 1004 can include circuits that provide wired and/or wireless communication with the user device 104. In some implementations, the communication module 1004 can include wired communication circuits, such as USB communication circuits. In some implementations, the communication module 1004 can include wireless communication circuits, such as Bluetooth circuits and/or WiFi circuits.

Using the communication module 1004, the cooling device 1000 and the user device 104 can communicate with each other. The processing module 1002 can transmit/receive data to/from the user device 104 via the communication module 1004. Example data may include cooling profiles and other information requests, such as status updates (e.g., charging status, battery charge level, and/or cooling device configuration settings). The processing module 1002 can also receive instructions/commands from the user device 104, such as instructions to increase/decrease cooling. In some implementations, the processing module 1002 (e.g., a microcontroller) may include circuits that provide wired/wireless communication (e.g., USB/Bluetooth). In some implementations, the user device 104 can transfer update data to the cooling device 1000 to update the software/firmware of the cooling device 1000.

The cooling device 1000 may include a battery 1014 (e.g., a rechargeable or non-rechargeable battery). An example battery may include a Lithium-Ion or Lithium-Polymer type battery, although a variety of battery options are possible. A power source (e.g., a wall adapter power cord or USB power plug) can be plugged into the power input port 108 of the cooling device 1000 to charge the battery 1014. In some implementations, the cooling device 1000 may not include a battery. Instead, the cooling device 1000 may be powered via the power input port 108. The cooling device 1000 includes a power module 1008 that may control charging of the battery 1014, regulate voltage(s) of the device electronics 302, regulate power output to the device electronics 302, and monitor the state of charge of the battery 1014. In some implementations, the battery itself may contain a protection circuit module (PCM) that protects the battery from high current discharge, over voltage during charging, and under voltage during discharge. In some implementations, the power module 1008 may include circuits configured to modulate the voltage and current into the battery 1014 during charging. For example, the power module 1008 may include a Microchip MCP73832 charge control IC and supporting passive components. The power module may also include electro-static discharge (ESD) protection.

In some implementations, the power module 1008 may control charging of the cooling device 1000 from the user device 104. For example, the cooling device 1000 may draw power from the user device 104 (e.g., a laptop or tablet), which may allow the cooling device 1000 to run longer. In some implementations, the power module 1008 may control charging of the user device 104 or other equipment from the cooling device 1000. For example, the cooling device 1000 can deliver power to the user device 104 (e.g., a phone or tablet) to extend the battery life of the user device 104, which the user may be using to control the cooling device

1000. In some cases, if the user device 104 is in communication with the cooling device 1000 and the battery 1014 is running low on the user device 104, the user device 104 may prompt the user to plug into the cooling device 1000 in order to charge the battery 1014 of the user device. In other cases, if the user device 104 is in communication with the cooling device 1000 and the battery 1014 is running low on the cooling device 1000, the cooling device 1000 may prompt the user to plug the cooling device 1000 into the user device 104 in order to charge the battery 1014 of the cooling device 1000 (e.g., prompt via a GUI on the user device 104).

The processing module 1002 along with the cooling control module 1010 can control the amount of cooling provided by the cooling units 1016. For example, the cooling control module 1010 can include electronics that control the amount of power delivered to the cooling units 1016. In one example, the cooling control module 1010 can include electronics that switch on/off the delivery of power to the individual cooling units 1016. As another example, the cooling control module 1010 can include electronics that can incrementally adjust the power delivery to the cooling units 1016 (e.g., adjust current and/or voltage).

The processing module 1002 may control the cooling control module 1010 to deliver power to the cooling units 1016 according to user input and/or a cooling profile. In some implementations, the cooling control module 1010 may include metal-oxide semiconductor field-effect transistor devices (MOSFETs) (e.g., power MOSFETs) that are controlled by a gate voltage generated by the processing module 1002 (e.g., a microcontroller). In implementations where MOSFET devices are used to control current through the cooling units 1016, the MOSFETs may be controlled via pulse-width modulation (PWM) signals or on/off commands generated by the processing module 1002 (e.g., microcontroller). In another implementation, the cooling units 1016 may receive power from a variable voltage power supply within the cooling device 1000 (instead of binary on/off control).

The processing module 1002 may control the cooling control module 1010 in a variety of different modes (e.g., a manual mode, automatic mode, and mixed mode). In the manual mode, the processing module 1002 may control the cooling control module 1010 to deliver power based on user input received via the user input devices on the cooling device 1000 and/or based on user input received from the user device 104 (e.g., via wireless communication). In the automatic mode, the processing module 1002 may control the cooling control module 1010 to deliver power according to a cooling profile. In the mixed mode, the processing module 1002 may control the cooling control module 1010 to deliver power according to a cooling profile and/or user input.

The cooling device 1000 (e.g., memory 1020) may store cooling profiles that include data indicating how to deliver power to one or more cooling units 1016. For example, the cooling profiles may include data indicating the voltage (e.g., analog voltage level and/or digital average with PWM) to apply to one or more cooling units 1016 over time. As another example, the cooling profiles may include data indicating the current to deliver to one or more cooling units 1016 over time. A cooling profile may include one or more cooling unit profiles. A cooling unit profile may include data indicating how to deliver power to a single cooling unit 1016 (e.g., between two electrical contacts connected to the cooling unit). In one example, if the cooling device 1000 includes two cooling units 1016, the cooling profile may include two cooling unit profiles.

The cooling profile (e.g., including multiple cooling unit profiles) can be stored in a variety of ways. In general, the data stored in the cooling profile indicates to the processing module 1002 and cooling control module 1010 how to deliver power to the cooling unit(s) 1016. In some implementations, the cooling profile may include a plurality of digital values indicating current/voltage to be delivered to the cooling unit(s) 1016 over time. In other examples, the cooling profile may be stored as a function that yields current/voltage over time. Note that in some cases, the values stored in the cooling profiles may not be voltage/current values over time, but instead may be digital values (e.g., PWM control values) used by the processing module 1002 and/or cooling control module 1010 to cause power to be delivered to the cooling unit(s) 1016 over time.

Figure 11A:
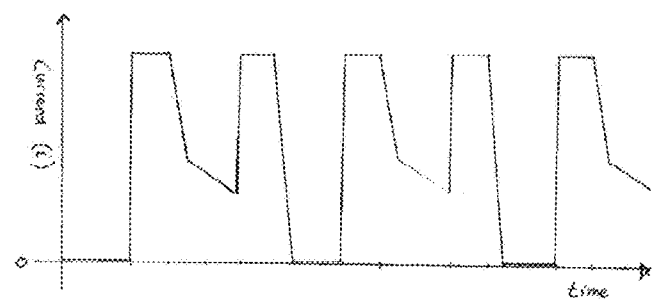
FIGS. 11A-11E are example current versus time graphs for a cooling device.
Figure 11B:
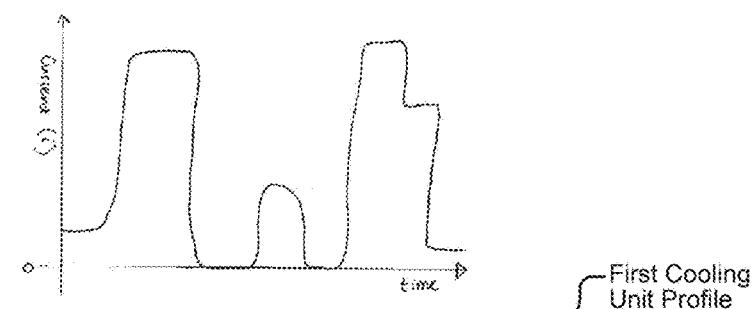

FIGS. 11A-11E illustrate example current versus time curves that the cooling device 100 may generate according to cooling profiles stored on the cooling device 100. FIGS. 11A-11B illustrate current versus time for a single cooling unit 200. FIG. 11A illustrates delivering power to a cooling unit 200 in a repetitive pattern. FIG. 11B illustrates delivering power to the cooling unit 200 in a more irregular pattern. The pattern in FIG. 11B may be repeated (e.g., periodic) or non-repetitive.

Figure 11C:
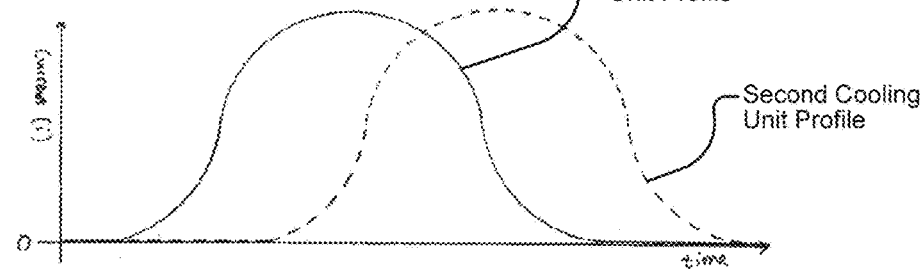
Figure 11D:
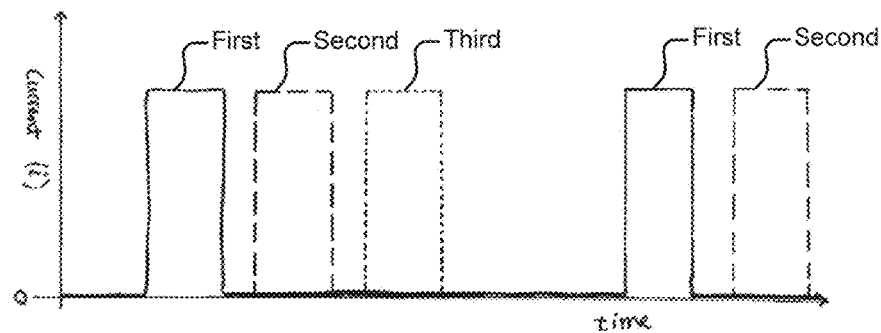

FIGS. 11C-11D illustrate current versus time for multiple cooling units 200. FIG. 11C illustrates a first and second current delivered to first and second cooling units. The first curve (solid line) may be stored as a first cooling unit profile for the first cooling unit. The second curve (broken line) may be stored as a second cooling unit profile for a second cooling unit. The cooling profile for FIG. 11C may include both the first and second cooling unit profiles. Note that the two cooling unit profiles of FIG. 11C store the same current curve, but the current curves are offset in time from one another. FIG. 11D illustrates three current curves for three separate cooling units. The three current curves are similar in shape, but offset in time from one another.

In some implementations, the user may perceive the offsetting of similar curves as a wave of cooling that passes across the cooling device. For example, if a cooling device has first and second cooling units next to one another and operates according to FIG. 11C, the user may first feel cooling provided by the first cooling unit and then feel a similar cooling in the adjacent second cooling unit as though a cool wave is flowing across the cooling device from one cooling unit to the next. In some implementations, the cooling device and/or user device may include controls (e.g., buttons and/or GUI elements) that the user can use to cause the time offset between two or more cooling units.

Figure 11E:
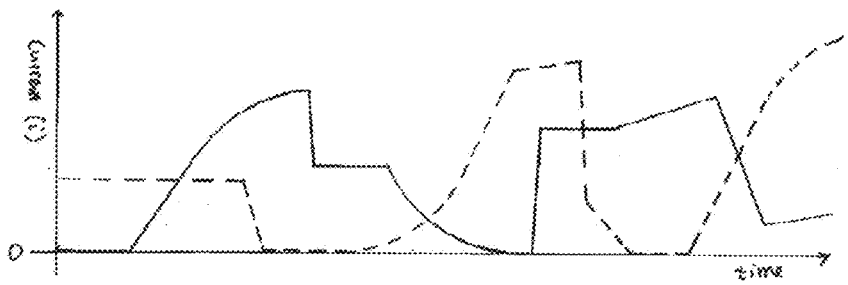

FIG. 11E illustrates two different current curves for two separate cooling units. Each of the current curves in FIG. 11E may be repeated or non-repetitive. The current curves of FIG. 11E may provide an irregular pattern of cooling that the user may perceive as unpredictable.

FIGS. 11A-11E illustrate a variety of different cooling patterns. Cooling profiles may include patterns similar to, or different from, the illustrated cooling patterns (e.g., regular/irregular/repetitive/non-repetitive). Additionally, a cooling profile may include cooling patterns that transition from repetitive to non-repetitive and/or from regular to irregular (or vice versa) over time. As described herein, a user may create new cooling patterns or modify existing cooling patterns while using the cooling device or working offline.

The duration of cooling pulses (e.g., as illustrated in FIG. 11D) deliverable by the cooling device 100 may vary depending on a variety of parameters. In some implementations, the duration of cooling pulses may be selected based on response times of the cooling device 100 and/or the user's ability to perceive the cooling. For example, response times of the cooling device 100 (e.g., cooling units 200) affecting the time required to provide cooling to a user may determine the minimum duration of cooling pulses. As another example, a user's ability to perceive the changes in cooling being delivered may determine the minimum duration of cooling pulses. For example, if a user is unable to differentiate cooling pulses having a duration of less than one second from cooling pulses having a duration of one second, then the minimum pulse duration may be set to one second. The ability of a user to perceive changes in cooling may depend on the region of the body to which the cooling device 100 is applied. Accordingly, the minimum duration of cooling pulses may also depend on where the cooling device 100 is to be applied. In some implementations, the pulses illustrated in FIG. 11D may have a duration on the order of a second or more, although the pulses may be set to a duration of less than a second if perceptible by the user.

In some implementations, the cooling device 100 can control power delivered to the cooling units 200 based on a sensed and/or estimated temperature. For example, the cooling device 100 may control the delivery of power to meet a target temperature that is adjustable by the user. As another example, the cooling device 100 may control the delivery of power such that the temperature remains greater than a threshold temperature, such as a temperature threshold set by a user or a minimum allowable temperature (e.g., in factory settings).

The cooling device 100 can control cooling based on the temperature of the cooling device 100 in proximity to the user (e.g., the temperature of a cooling zone). In some implementations, the cooling device 100 can include one or more temperature sensors that sense temperatures in one or more cooling zones. In implementations where the cooling device 100 includes one or more temperature sensors, the cooling device 100 can control cooling based on temperature indicated by the temperature sensor.

In implementations where the cooling device 1000 does not include a temperature sensor, the processing module 1002 may estimate the temperature and control cooling based on the estimated temperature. The processing module 1002 may estimate the temperature based on one or more factors, such as the amount of power delivered to the cooling units 1016 (e.g., voltage/current) and the amount of time over which the power has been delivered. In some implementations, the memory 1020 may include temperature estimation models and/or tables that the processing module 1002 may use to estimate temperature. For example, the models/tables may indicate an estimated temperature for power values and/or a cooling profile over time. The processing module 1002 may also determine the temperature based on a combination of temperature indicated by the temperature sensors 1018 and the estimated temperature. In some implementations, the memory 1020 may include models/tables that use sensed temperatures to estimate additional temperatures.

Although the cooling device 100 can control cooling based on temperature (e.g., a target temperature), in some implementations, the cooling device 100 can control cooling based on alternative and/or additional parameters, such as an amount of energy/heat withdrawn from a user. For example, the cooling device 100 may control cooling to reach a target amount or rate of energy withdrawn. The cooling device 100 may determine the amount of energy withdrawn based on a variety of parameters, such as the delivered current/voltage to the cooling units 200 and the amount of time over which the current/voltage was delivered.

In some implementations, the cooling device 100 may include components that indicate an amount of pressure placed on the cooling device 100 (e.g., a pressure sensor). Such components may be embedded in and/or attached to the package substrate or device packaging. In these implementations, the cooling device 100 may control cooling based on the indicated pressure (e.g., as indicated by the pressure sensor). In one example, the cooling device 100 may reduce an amount of cooling if the pressure sensing components indicate that the cooling device 100 is pressed more firmly against the user, as the pressure may be indicative of a close contact and better heat transfer between the cooling device and the user. In another example, the cooling device 100 may be configured to increase cooling in response to increased pressure placed on the cooling device 100. In this example, if a user presses their hand on top of the cooling device 100 to increase pressure on the cooling device 100, the cooling device may respond by delivering more cooling to the area.

FIGS. 12A-12C illustrate example methods describing operation of the cooling device 100 in different modes of operation. FIG. 12A illustrates an example method describing operation of the cooling device 100 in the manual mode. In FIG. 12A, the cooling device 100 is initially started (e.g., using an on/off button) in block 1200. In block 1202, the cooling device 100 (e.g., the device electronics) sets an initial power delivery to the one or more cooling units 200. The cooling device 100 then waits for user input in block 1204, which may include user interaction with manual controls (e.g., user input buttons 102) on the cooling device 100 and/or user interaction with a GUI on the user device 104. Example user input may include incrementing/decrementing cooling (e.g., power delivery). If the cooling device 100 receives user input in block 1204, the cooling device 100 may modify power delivery to the one or more cooling units 200 according to the user input in block 1206.

FIG. 12B illustrates an example method describing operation of the cooling device 100 in the automatic mode. In FIG. 12B, the cooling device 100 is initially started in block 1210. Upon starting, the cooling device 100 may load a cooling profile in block 1212. For example, the cooling device 100 may load a stored cooling profile or may receive a cooling profile from the user device 104. In block 1214, the cooling device 100 controls cooling (e.g., power delivery) according to the loaded cooling profile.

FIG. 12C illustrates an example method describing operation of the cooling device 100 in the mixed mode. In blocks 1220-1224, the cooling device is initially started, loads a cooling profile, and controls cooling according to the cooling profile, as described with respect to FIG. 12B. In the mixed mode, the user may modify the cooling profile and/or load another cooling profile onto the cooling device 100 in block 1226. For example, the user may provide user input that modifies the currently running cooling profile via manual controls on the cooling device 100 and/or GUI controls on the user device 104. The user may also load new cooling profiles to run on the cooling device 100. For example, the user may select a new cooling profile stored on the cooling device 100 or download a cooling profile from the user device 104 to the cooling device 100. In block 1228, the cooling device 100 may run the new profile until the user modifies the new profile and/or loads another cooling profile.

FIG. 13 illustrates a plurality of user devices 1300-1, 1300-2, . . . , 1300-N in communication with a remote server 1302 via a network 1304. Each of the user devices 1300 is in communication with a different cooling device 1306-1, 1306-2, . . . , 1306-N. In FIG. 13, different users may each own/operate one of the user devices 1300 and one of the cooling devices 1306. The remote server 1302 may be owned/operated by a party other than the users. For example, the remote server 1302 may be operated by the developer/manufacturer of the cooling devices 1306. In these examples, the developer/manufacturer of the cooling devices 1306 can provide data and programs to the remote server 1302 for download by the user devices 1300.

In some implementations, the remote server 1302 can provide one or more programs (e.g., applications) to the user devices 1300. The one or more programs may be executed by the user devices 1300 to interact with the cooling devices 1306. For example, the one or more programs may generate GUIs on the user devices 1300 which the users may use to interact with the cooling devices 1306 (e.g., see FIGS. 14A-14O). The user devices 1300 may download and execute the one or more programs in order to interact with the cooling devices 1306 (e.g., after the users purchase the cooling devices).

In some implementations, the remote server 1302 may store data that can be accessed by the user devices 1300. For example, the remote server 1302 can store cooling profiles. In some implementations, the cooling profiles may be created by the owner/operator of the remote server 1302 and uploaded to the remote server 1302. In another example, the cooling profiles may be created by one or more of the users and uploaded to the remote server 1302. Users may download the cooling profiles and load the cooling profiles on their cooling devices 1306. Providing the cooling profiles for download may help new and existing users conveniently acquire and try new cooling profiles.

A cooling profile may also include associated data. The associated data may include cooling device information that indicates the type of cooling device with which the cooling profile may be used. In one example, the associated data may include cooling device identification numbers (e.g., model numbers) indicating the type of cooling device with which the cooling profile is compatible. As another example, the associated data may indicate that the cooling profile should be used with a certain device having a certain configuration of cooling units and/or sensors.

In some implementations, the users can store user data on the remote server 1302. Example user data may include the types of conditions for which the user uses the cooling device 1306 along with data indicating how effective various cooling profiles are in alleviating the condition. For example, the user may upload a cooling profile and additional data along with the cooling profile indicating the condition for which the cooling profile is used and how effective the cooling profile is in alleviating the condition (e.g., a score from 1-10). The remote server 1302 can make recommendations to users based on uploaded user data. For example, the remote server 1302 can recommend cooling profiles to users with a condition if the cooling profiles are indicated as effective by other users for the same/similar conditions. The remote server 1302 can also recommend additional activities or behaviors that can help the user while using the cooling device 1306, or independent of cooling device usage. These recommendations can include exercise guidance or stretching suggestions to reduce pain in a given part of the body. In some implementations, the user device 1300 may also make recommendations without communication with the remote server 1302. For example, the user device 1300 may make recommendations based on detected motion over time. The GUI can provide notifications/recommendations to the user (e.g., that the user stretch, increase activity, etc.). In a specific example, with respect to low back pain, the user device 1300 can alert the user that they should move around and do some stretching/exercises to help reduce the pain that they are feeling. In this way, the remote server 1302, user devices 1300, and cooling devices 1306 are together able to provide a well-rounded therapeutic solution for the users.

FIGS. 14A-14O illustrate example GUIs that can be displayed on the user devices. Users may use the example GUIs to: 1) control the cooling device, 2) transfer data to the cooling device, 3) retrieve data from the cooling device, 4) transfer data to the remote server, 5) retrieve data from the remote server, and perform other operations, such as creating and modifying cooling profiles. In FIGS. 14A-14O, the user devices 1400-1, 1400-2, . . . , 1400-15 include a touchscreen that overlays the GUIs. A user can interact with the GUI by interacting with the touchscreen display (e.g., touching/swiping the touchscreen display). In other implementations, a user device may include additional user inputs, such as buttons, that the user may use to control the cooling device 100. The GUIs of FIGS. 14A-14O are only example GUIs used to illustrate various example features of the user devices, and as such, do not represent an exhaustive set of features that may be provided by the user devices.

FIG. 14A illustrates a GUI that the user may use to control the cooling device 100 (e.g., in the manual mode). In FIG. 14A, the GUI controls a cooling device 100 having two cooling zones, where each cooling zone includes one or more cooling units 200. The user can interact with two different GUI elements 1402-1, 1402-2 (e.g., sliders), each of which controls cooling within different cooling zones. For example, the user may slide (e.g., swipe) the slider icons 1402 in the high/low direction to increase/decrease the amount of cooling in the cooling zones. Although sliding GUI elements are illustrated, in other implementations, other GUI elements may be used to control cooling, such as graphical buttons (e.g., +/− buttons) or dials. Although GUI elements for incrementing/decrementing cooling are illustrated in FIG. 14A, other GUIs may include other controls, such as controls that control both cooling zones at the same time or controls that can be used to offset the timing of different cooling zones (e.g., to create a wave of cooling).

Figure 14C:
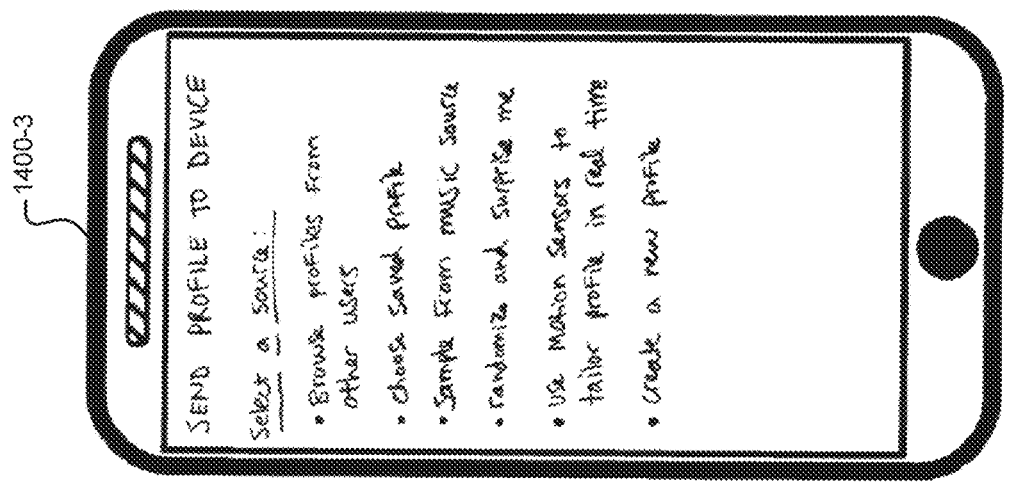
Figure 14B:
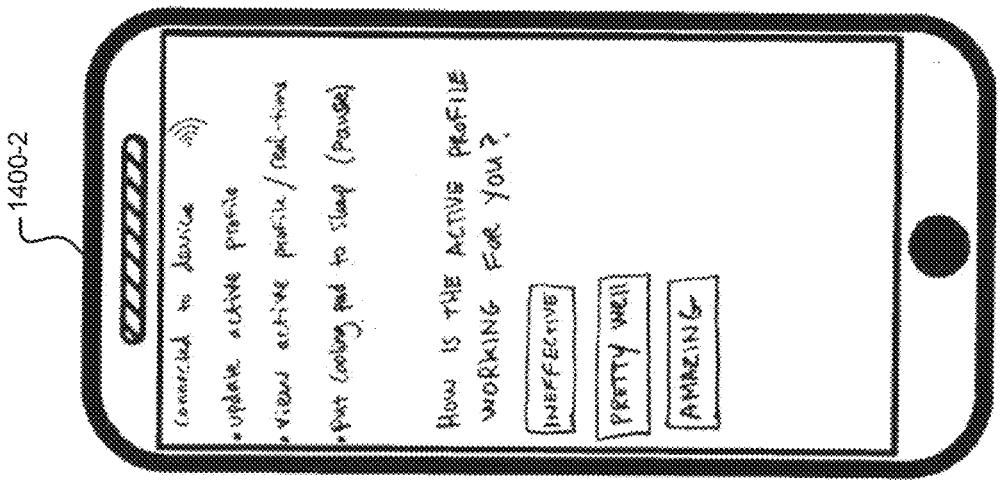

FIGS. 14B-14C illustrate GUIs that provide information to the user, provide controls for the user, and acquire feedback from the user. The GUI in FIG. 14B indicates that the user device 1400-2 is connected to the cooling device 100. The GUI also gives the user various controls for the cooling device 100. For example, the user can: 1) update the active cooling profile running on the cooling device, 2) view the active cooling profile in real-time in another GUI, and 3) put the cooling device to sleep. Additionally, the GUI prompts the user for feedback indicating how effective the cooling profile is for the user.

FIG. 14C illustrates a GUI that allows the user to select a new cooling profile to run on the cooling device 100 and/or modify a current cooling profile. The user can select a new cooling profile from other users (e.g., from the remote server 1302), select a profile saved on the user device 1400-3 or remote server 1302, or select a random profile. The user can also create a new profile. In some implementations, the cooling profiles can be assigned names (e.g., by the user/creator) so that the user can identify the cooling profile.

Additionally, the user may use motion sensors or music to generate a profile. In the case of generating profiles based on motion, the cooling device 100 may detect motion patterns from the motion sensor (such as a walking motion) and/or may respond to real-time changes in the user's motion. For example, the cooling device 100 may detect a regular periodic frequency within the user's motion. In response to this detected frequency, the cooling device 100 can deliver pulses of cooling to coincide with the user's motion. Further, in order to have the pulse of cooling arrive at the user's body in-phase with his/her periodic motion, the cooling device 100 may delay/offset the pulse of cooling by a given amount (based on the thermodynamic properties of the device package). In the case of generating profiles based on music, the user may choose an audio stream on the user device 104 (either downloaded onto the user device 104 or streaming on the internet). The audio stream's contents can be processed (e.g., by an external computing device and/or the cooling device 100) to find underlying rhythms and frequency patterns, which can then be converted to cooling delivery profiles. For example, if an audio stream has a melody that rises and falls at a given rate, then a profile can be created to match it. Introducing a time offset in the music stream can allow for the timing of the music to match the cooling felt by the user. This time offset can account for the time needed for the thermal gradients to be created by the cooling device 100. A benefit of using music as a seed for generating new profiles is that it allows for varied and diverse profiles without the need for a high degree of user input. Another example benefit of using music to generate profiles is that the user may listen to the music while experiencing the music-generated profile, so that the effect of the cooling device 100 is combined with the effect of hearing the music stream.

Figure 14D:
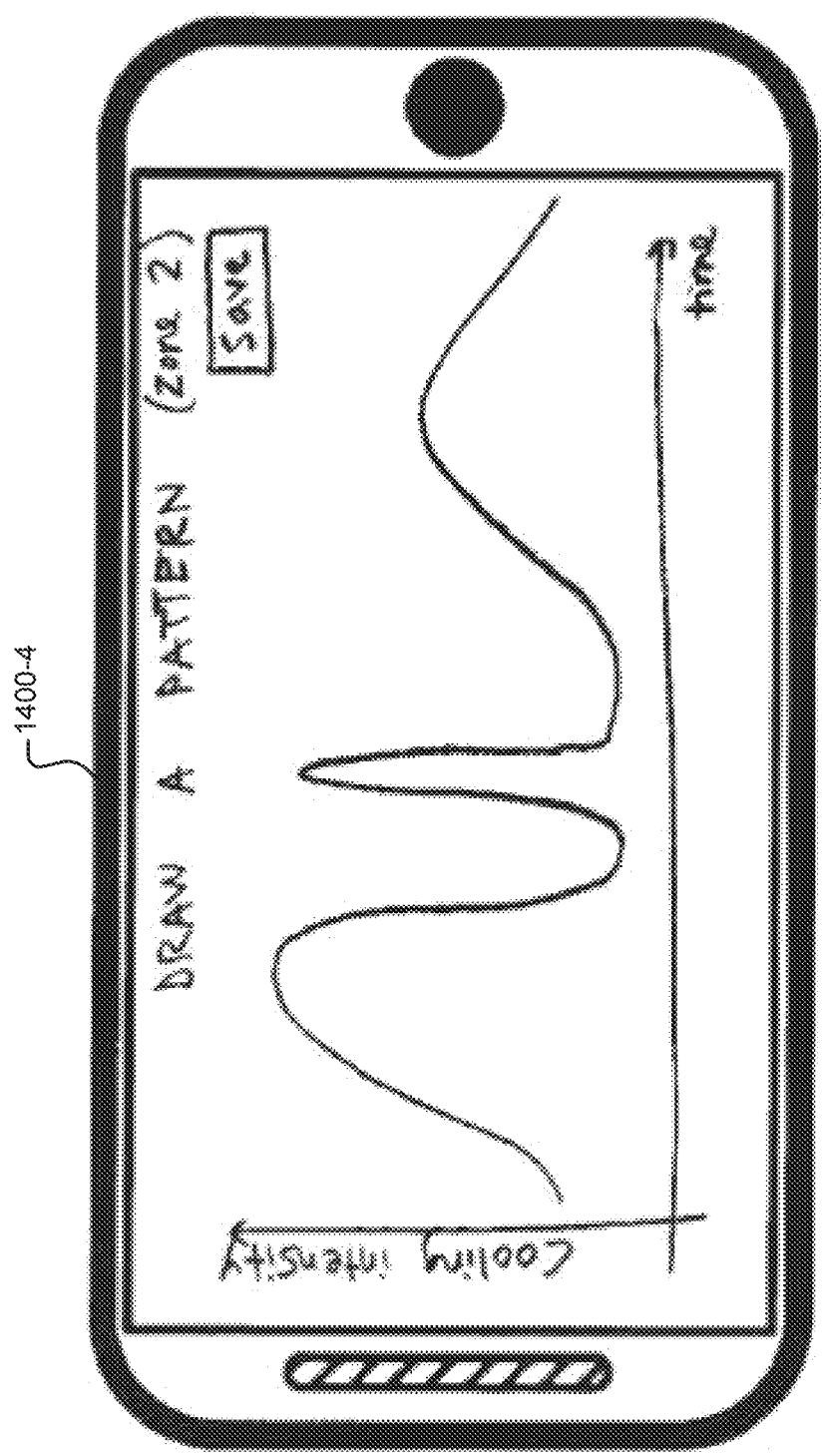
Figure 14G:
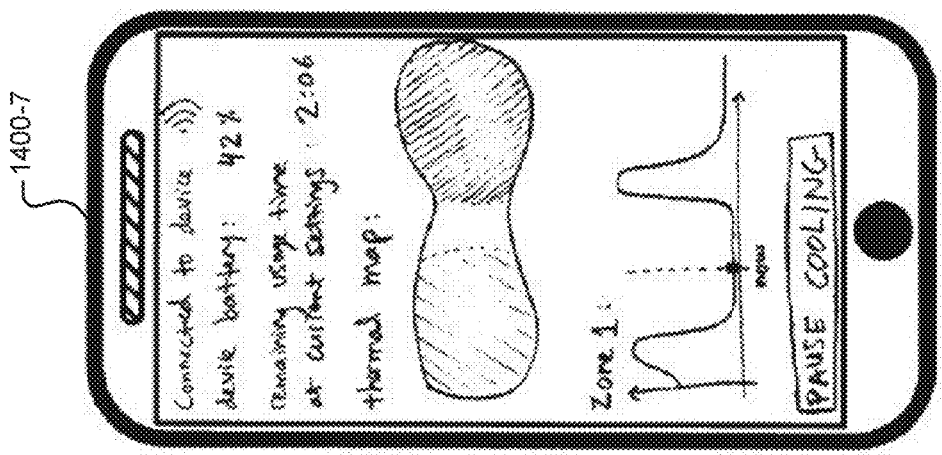

FIG. 14D illustrates a GUI that allows a user to create a custom cooling profile. In the GUI, the user may draw a cooling pattern (e.g., with their finger or stylus). The user may then save the cooling pattern (i.e., cooling profile) and upload the cooling pattern to the cooling device 100. The user can retrieve and modify the saved cooling pattern at a later time.

Figure 14F:
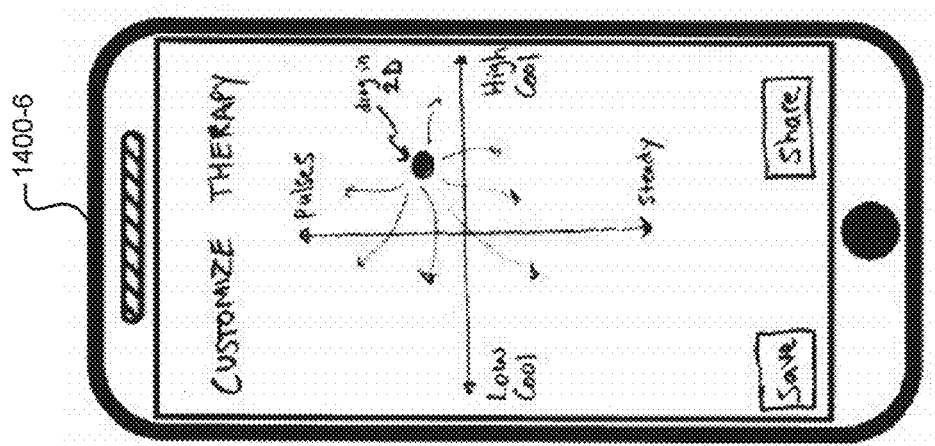
Figure 14E:
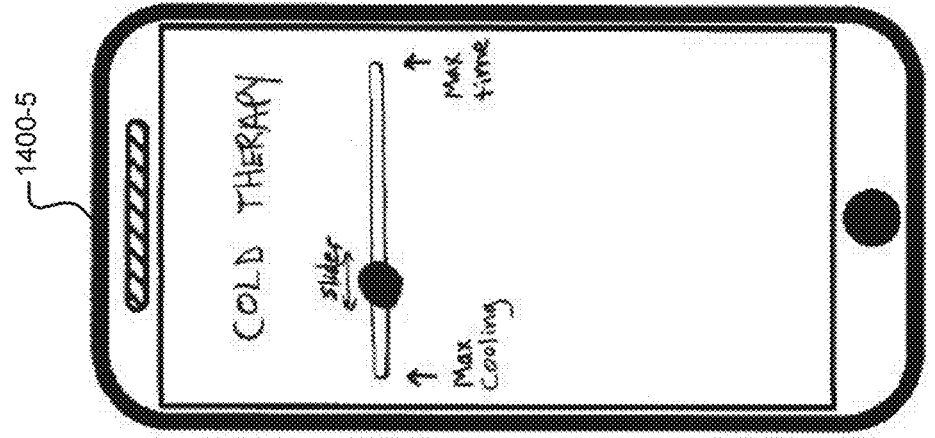
Figure 14J:
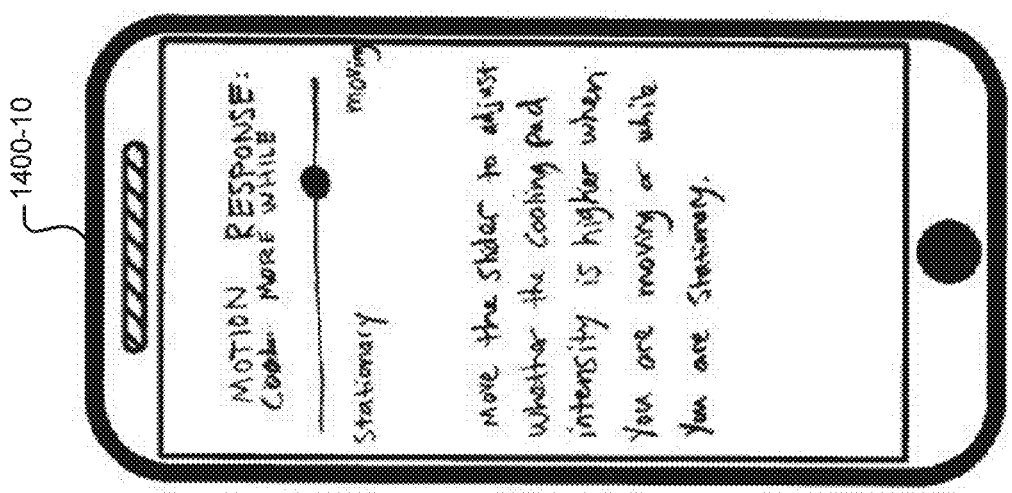
Figure 14I:
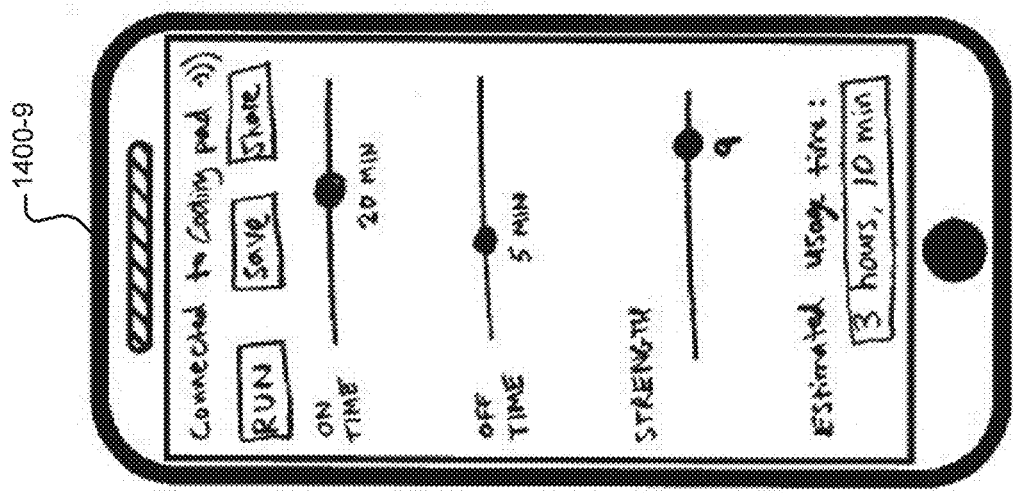

FIGS. 14E-14F illustrate GUIs that allow a user to specify their desires for a cooling profile, which may then be generated automatically by the user devices 1400-5, 1400-6. In FIG. 14E, the user can adjust a slider left or right to indicate that they would like maximum cooling or maximum cooling device operating time. In general, a greater amount of cooling may yield a shorter operating time when the cooling device 100 is running on a battery. The GUI provides the user with the choice of whether to increase cooling or increase operating time. The cooling device 100 may adjust the amplitude of the current cooling pattern according to the user's selection and/or select another cooling pattern based on the selected operating time and/or cooling.

The GUI of FIG. 14F illustrates a graph with four quadrants and a point that the user may position within the quadrants to control the intensity of cooling and whether the cooling is steady or in pulses. The user may drag the dot in the X direction to increase/decrease the amount of cooling. The user may drag the dot in the Y direction to modify the rate of cooling pulses delivered to the user. For example, dragging the dot toward the pulses portion of the Y axis may cause an increase in pulse frequency, whereas dragging the dot toward the steady portion of the Y axis may cause the pulse frequency to decrease (e.g., steady=no pulses).

FIG. 14G illustrates a GUI that conveys cooling device information to the user, including: 1) the connection status between the user device 1400-7 and the cooling device 100, 2) the battery status of the cooling device 100, and 3) the remaining operating time for the cooling device 100 at the current settings (e.g., the current cooling profile). The GUI also illustrates a thermal map of the cooling device that indicates cooling in different cooling zones. Additionally, the GUI illustrates the cooling profile running in zone 1 of the cooling device 100. Over time, the illustrated cooling profile may scroll from left to right as the cooling device 100 executes the cooling profile. This allows the user to visualize the past/present/future behavior of the cooling profile. The user may pause the cooling device 100 by pressing the "PAUSE COOLING" button in the GUI.

Figure 14H:
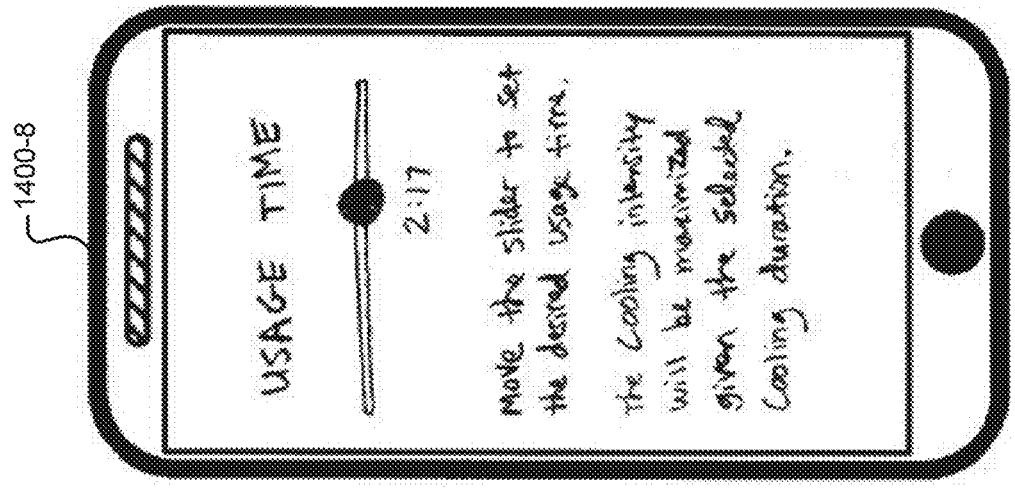

FIG. 14H illustrates a GUI that allows the user to select a desired usage (operation) time for the cooling device 100. For example, the user may slide the slider to the right/left to increase/decrease the usage time. The user device 1400-8 and/or the cooling device 100 may then update the current cooling profile or generate a new cooling profile based on the selected usage time.

FIG. 14I illustrates a GUI that allows the user to control how long a cooling profile is run, how long a cooling profile is turned off, and the strength of the cooling profile. For example, the user may use a slider GUI element to set an on time that sets how long the cooling profile should run. The user may also use a slider GUI element to set an off time that sets how long the cooling device 100 should cease cooling (e.g., pause) after running for the on time. The cooling device 100 may then repeat the on/off behavior for the selected on/off times. The user can use a slider GUI element to set the strength (e.g., the power) associated with the cooling profile, where a greater strength may increase the power delivery for a given cooling profile. The user device 1400-9 may then calculate the estimated usage time for the cooling device 100 according to the present battery level, the on/off times, and the strength. The GUI displays the estimated usage time to the user (e.g., 3 hours, 10 min). Modifying the on time and off time can extend/reduce the battery life (i.e., the estimated usage time) of the cooling device 100.

FIG. 14J illustrates a GUI that allows a user to tailor the motion response of the cooling device 100. As described herein, the cooling device 100 can determine the motion of the user based on a motion sensor included in the cooling device 100 and/or a motion sensor included on the user device 1400-10. The user may move the slider GUI element to the left or right to adjust whether the cooling device 100 provides more cooling while the user is stationary or moving.

Figures 14K, 14L, 14M:
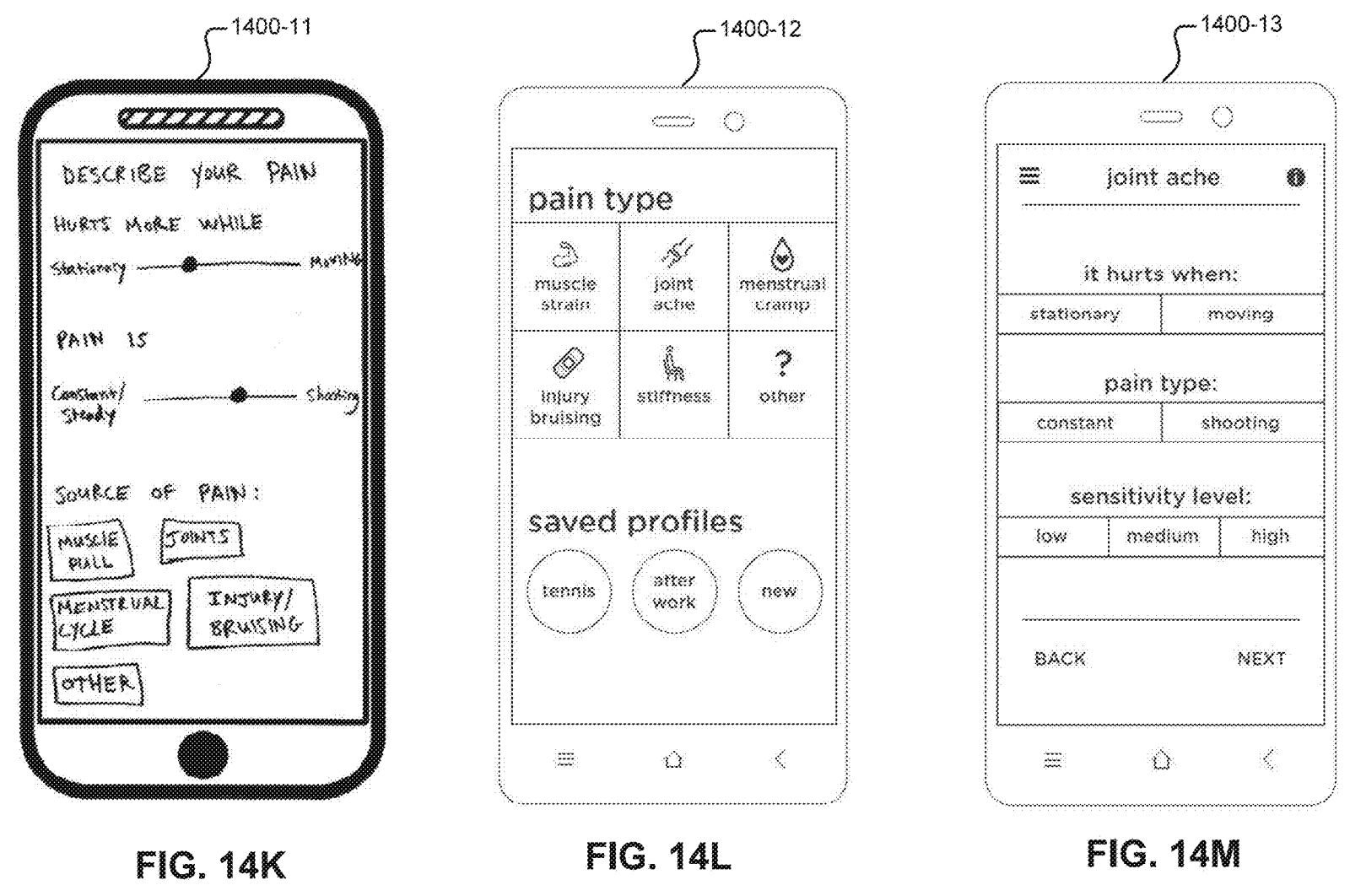

FIG. 14K illustrates a GUI that acquires user information. The GUI prompts the user to describe their pain based on whether the user is stationary/moving. The GUI also prompts the user to describe their pain in terms of whether it is consistent/steady or shooting. Additionally, the GUI prompts the user to indicate their source of pain. The user information acquired via the GUI may be stored on the user device 1400-11 and/or the remote server 1302. At a later time, the user may indicate which cooling profile(s) are most effective in comforting the pain described in the GUI. The effectiveness of one or more cooling profiles with respect to the reduction/elimination of pain described in the GUI may be stored at the remote server 1302 and/or user device 1400-11 and be used to make recommendations to the user or other users, as described herein. FIGS. 14L-14M illustrate additional GUIs that allow the user to specify their pain type and classify their pain. Additionally, the GUI of FIG. 14L allows the user to load various saved profiles, which are named (e.g., by the user) according to their uses.

Figure 14N:
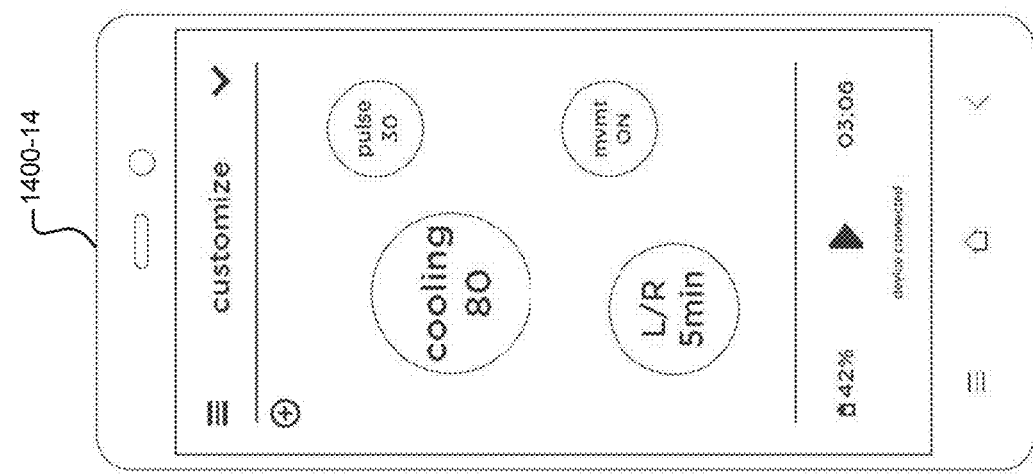
Figure 14O:
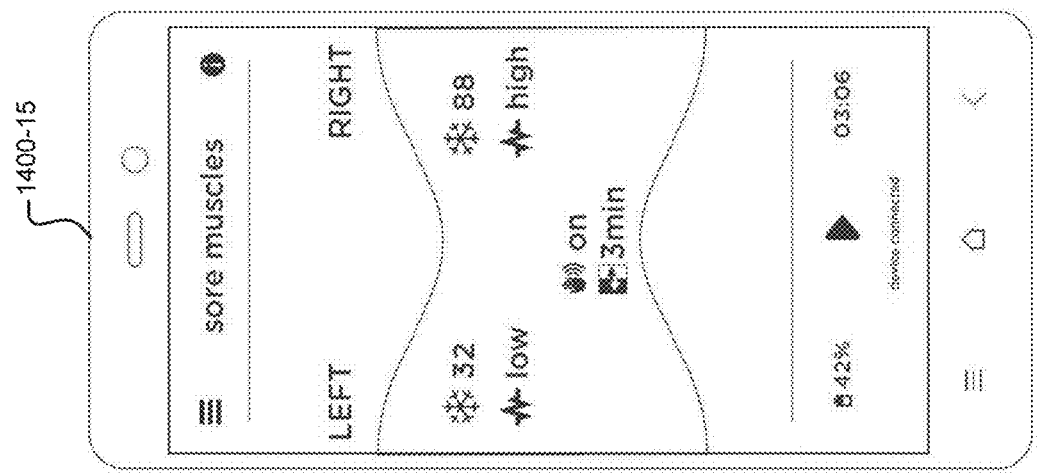

FIG. 14N illustrates a GUI that allows the user to control and monitor the cooling device 100 in a variety of different ways. For example, the user may interact with various GUI elements in order to control/monitor the amount of cooling. Specifically, a "cooling 80" button indicates that cooling is set to a level of 80 (e.g., out of a possible strength from 0-100, where 100 is a maximum cooling level). The user may depress the button to modify cooling (e.g., via an additional GUI element presented to the user after depressing the button). The user may also control/monitor the rate of pulses delivered to the user using the pulse button (e.g., in a similar manner as the cooling button). The user may also control whether the cooling device responds to movement using the mvmt button. Additionally, the user may control how long the cooling device cools in different zones. Specifically, using the L/R button, the user has selected 5 minute cooling intervals that switch between the left and right sides of the cooling device 100. Using the play button, the user can cause the cooling device 100 to cool according to the selected parameters.

FIG. 14O illustrates a GUI that allows the user to control and monitor the cooling device 100 in a similar manner described above. Specifically, the user may control/monitor the operation of the left and right sides of the cooling device 100. The snowflake icons may indicate the current cooling level.

The cooling device 100 can include a device package that can house one or more cooling units 200, device electronics 302, and other components (e.g., a battery 304). The device package may include flexible portions that conform to a user's body. FIGS. 1A-1C and 15A-21B illustrate different example cooling devices 100 having different packages.

FIGS. 1A-1C illustrate a first cooling device 100-1, as described above. FIGS. 15A-15D illustrate a second cooling device 100-2. The second cooling device package can include one or more cooling units 200 arranged in any manner throughout the package. The second cooling device 200-2 can be applied to different parts of the user's body. The second cooling device package, or any other cooling device package, can include one or more belt loops 1500 that receive a belt 1502 used to hold the cooling device 100-2 to a user's body. The belt 1502 can include a belt clasp 1503 for fastening ends of the belt 1502 together. With respect to FIG. 15A, the second cooling device 100-2 can include a user input button (e.g., an on/off button) and a power input port 108.

Figure 15A:
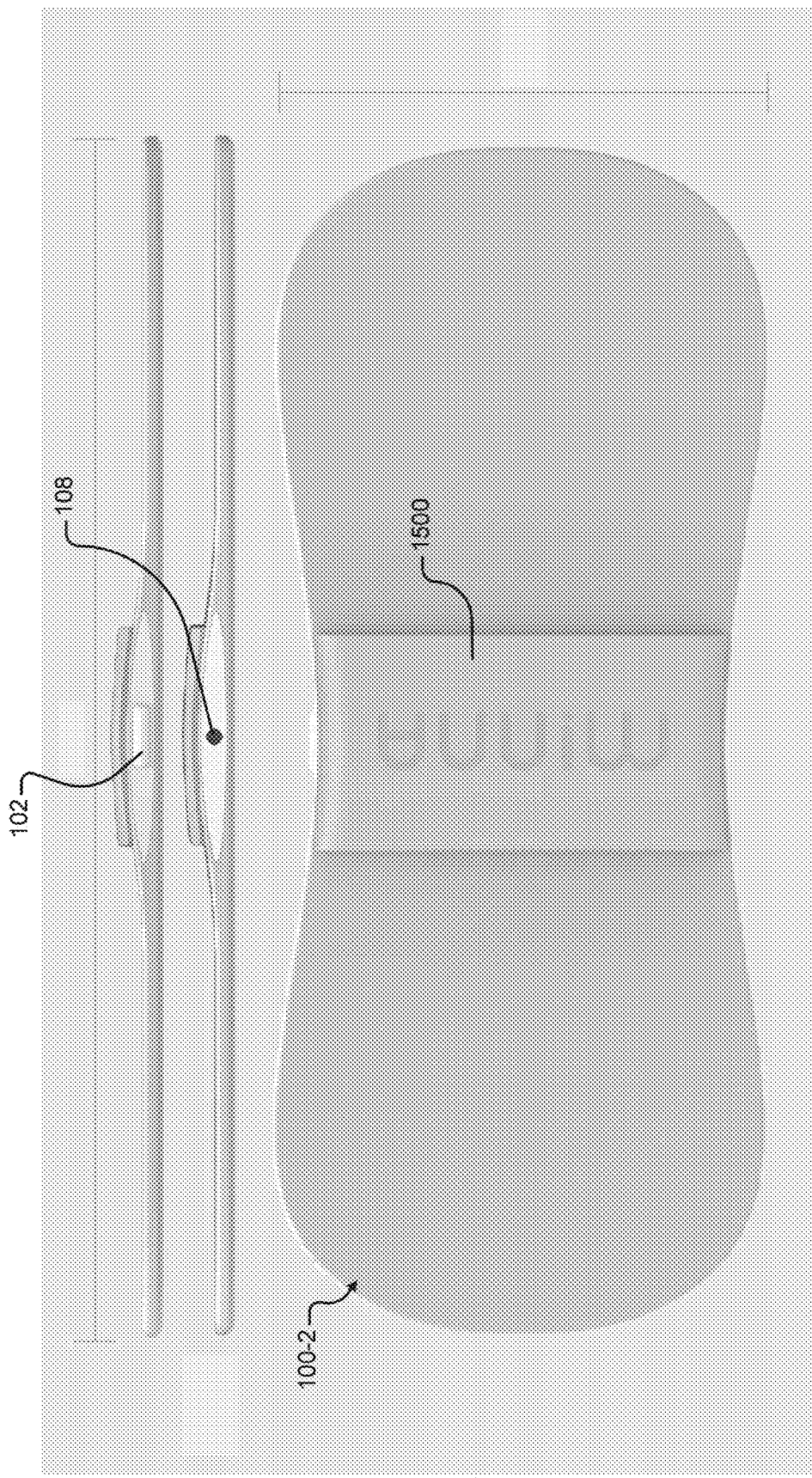
FIGS. 15A-21B illustrate additional example cooling devices.
Figure 15C:
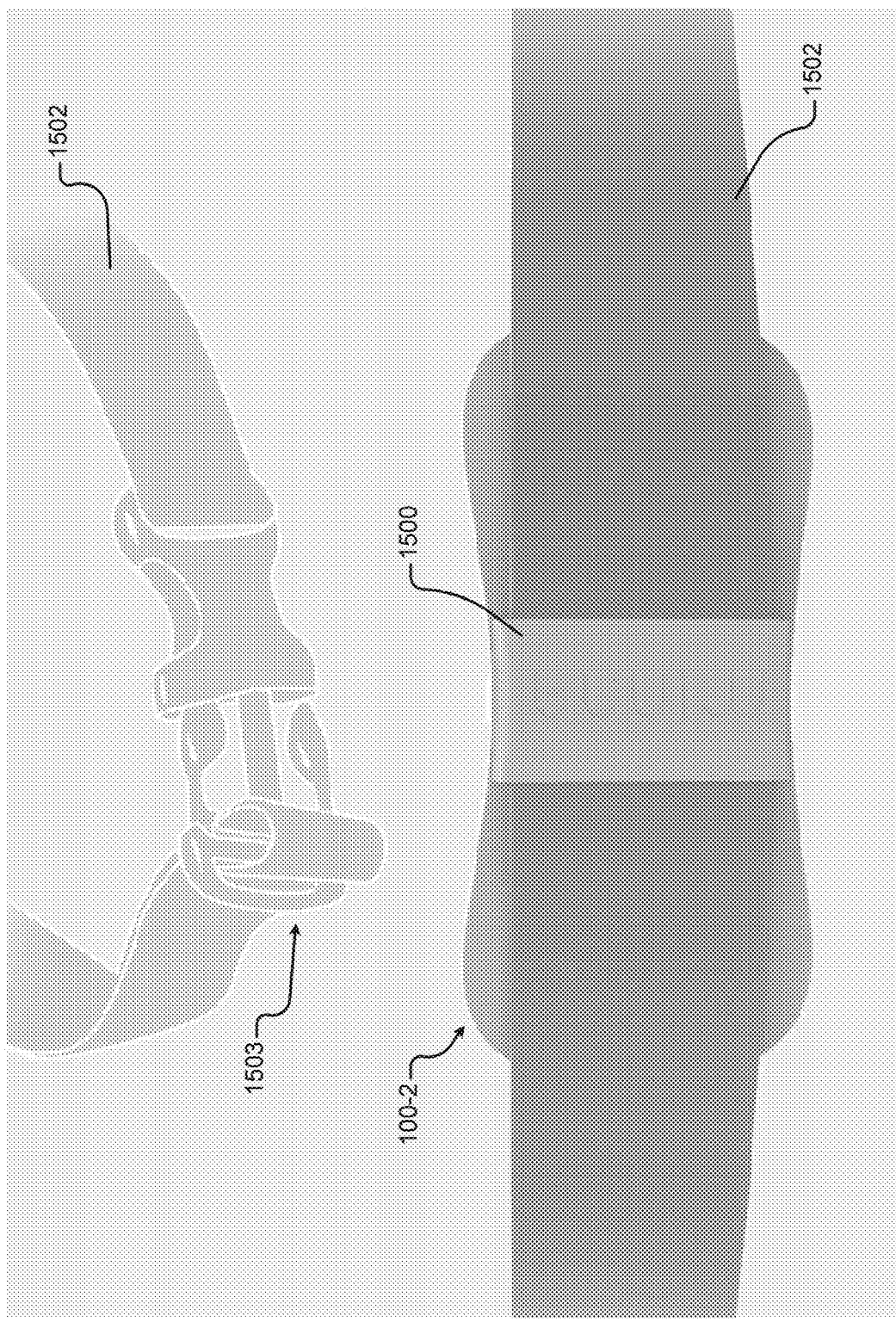
Figure 15D:
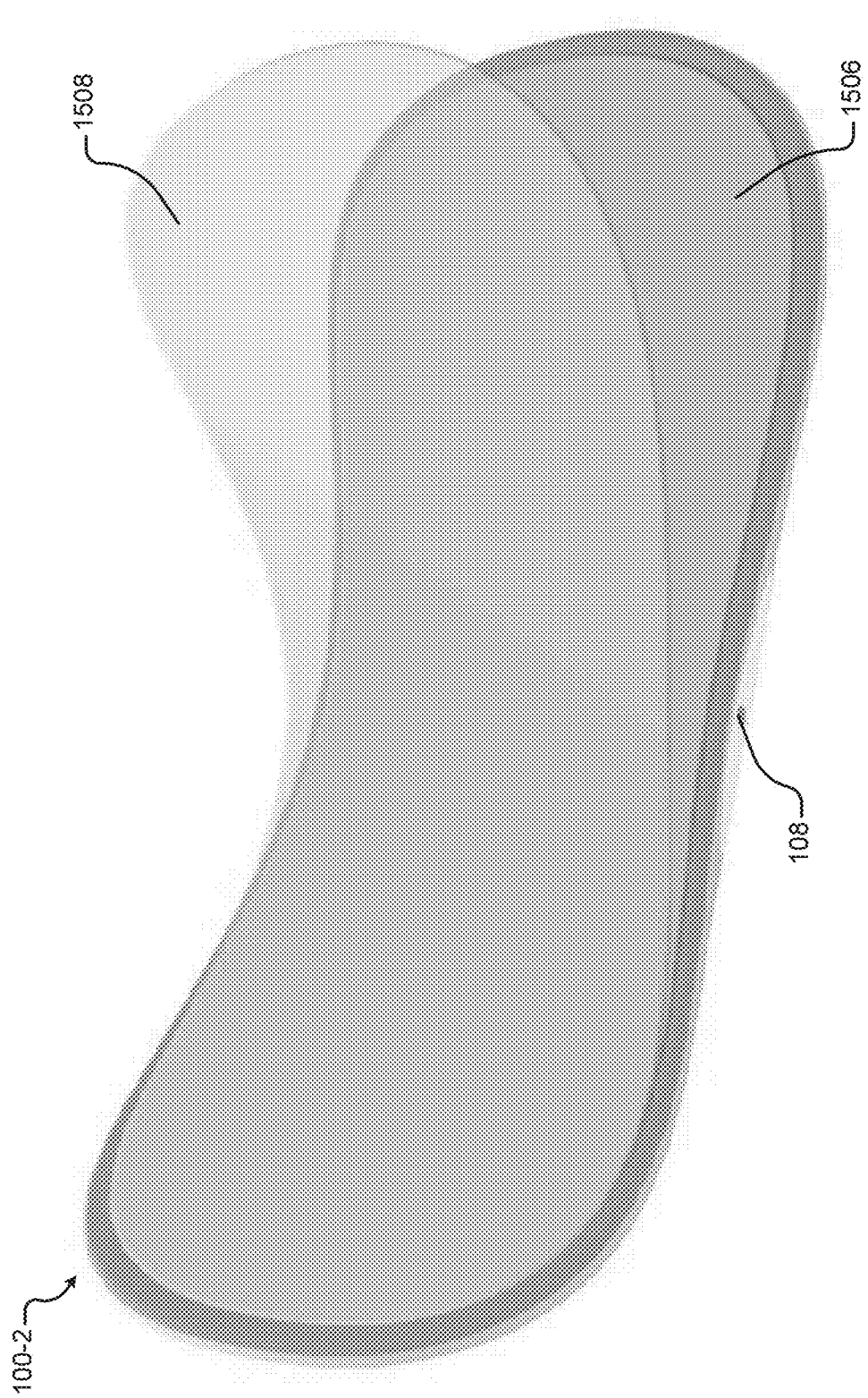

FIG. 15B illustrates an exploded view of the second cooling device 100-2. The second cooling device 100-2 includes an encapsulation. The encapsulation is formed from an encapsulation top cover 1504-1 and an encapsulation bottom cover 1504-2. The encapsulation 1504-1, 1504-2 encapsulates components of the cooling device 100-2, such as the cooling units 200, package substrate 300, battery 304, and device electronics 302. The top/bottom covers 1504-1, 1504-2 in FIG. 15B can be flexible material that can be adhered together or connected in another manner, such as fused, vulcanized, ultrasonically welded, or thermally welded. In some implementations, the encapsulation 1504-1, 1504-2 may not entirely cover the package substrate 300 including the cooling units 200. In these implementations, the package substrate 300, or other body contact layer (e.g., a thermally conductive layer) may contact the user (e.g., body or clothing). The encapsulation 1504-1, 1504-2 may be formed from materials including, but not limited to, cloth-based or fabric materials, molded flexible plastics/rubbers, foams, and synthetic fleece material. In some implementations, the cooling device 100-2 may include material/structure that imparts some rigidity to the cooling device 100-2. FIG. 15D illustrates an additional adhesive layer 1506 that may be attached to the encapsulation bottom cover 1504-2. The adhesive layer 1506 can include a removable cover layer 1508 that may be peeled from the adhesive layer 1506 to expose the adhesive layer 1506. The removable cover layer 1508 may be a smooth layer that adheres to the underlying adhesive but does not adhere to the user.

The second cooling device 100-2 of FIG. 15B includes a package substrate that may include cooling units (not illustrated). Additionally, the second cooling device 100-2 may include a thermal reservoir layer 1510. In some implementations, the thermal reservoir layer 1510 may be made thicker than that illustrated in FIG. 15B in order to provide more thermal mass.

The cooling devices 100 of FIGS. 15A-15D and FIGS. 17A-20 are illustrated as thinner than the cooling device 100-1 of FIGS. 1A-1C. This is because the cooling device 100-1 of FIGS. 1A-1C may include one or more thicker thermal reservoirs, whereas the cooling devices 100 of FIGS. 15A-15D and FIGS. 17A-20 may include thinner thermal reservoir layers, or no thermal reservoir layer at all. Each of the cooling devices 100 of FIGS. 15A-15D and FIGS. 17A-20 may be modified to include additional thermal reservoir material. In implementations of the cooling devices of FIGS. 15A-15D and FIGS. 17A-20 including additional thermal reservoir material, the devices of FIGS. 15A-15D and FIGS. 17A-20 may be made thicker. The increase in thickness of the cooling devices 100 may correspond to the thickness of added thermal reservoir material.

Figure 16A:
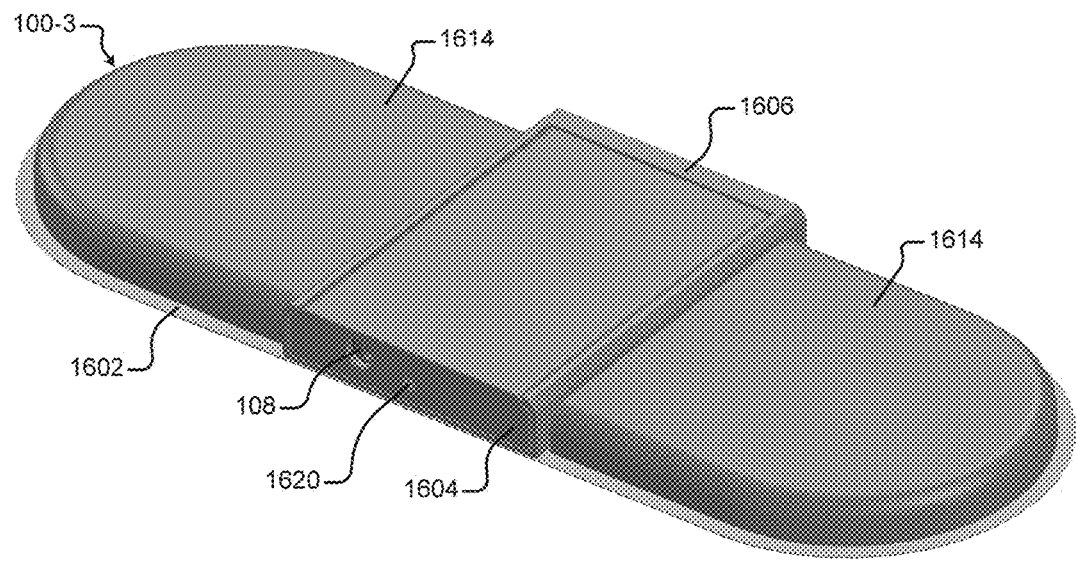
Figure 16B:
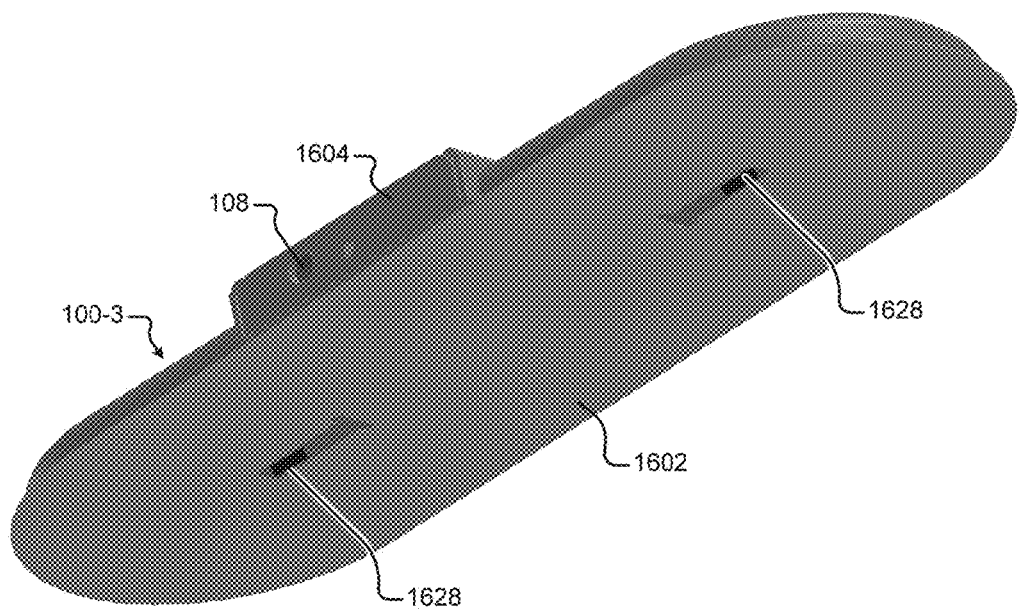
Figure 16C:
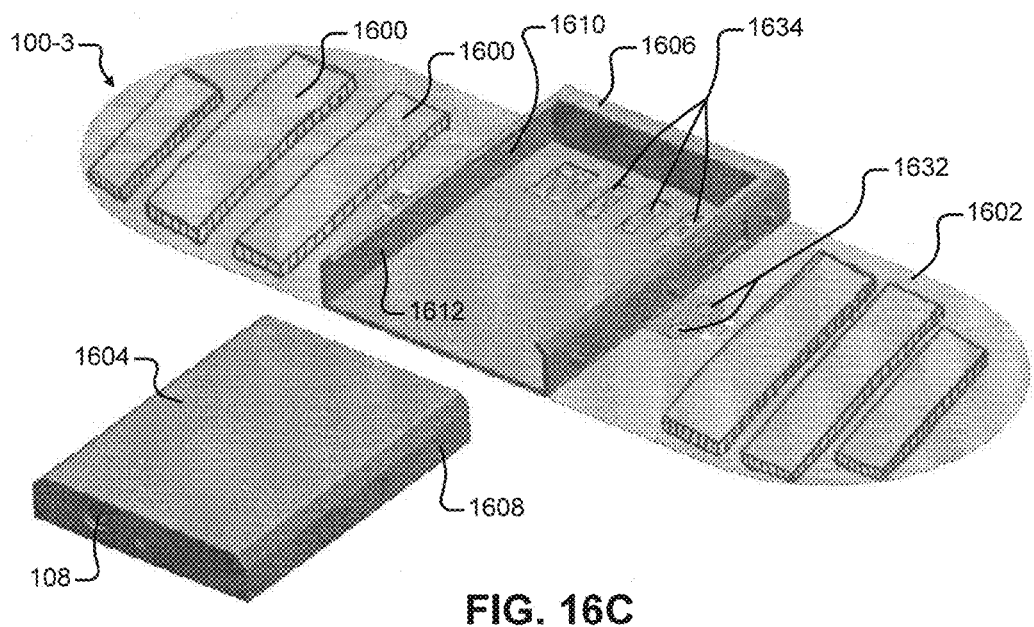
Figure 16D:
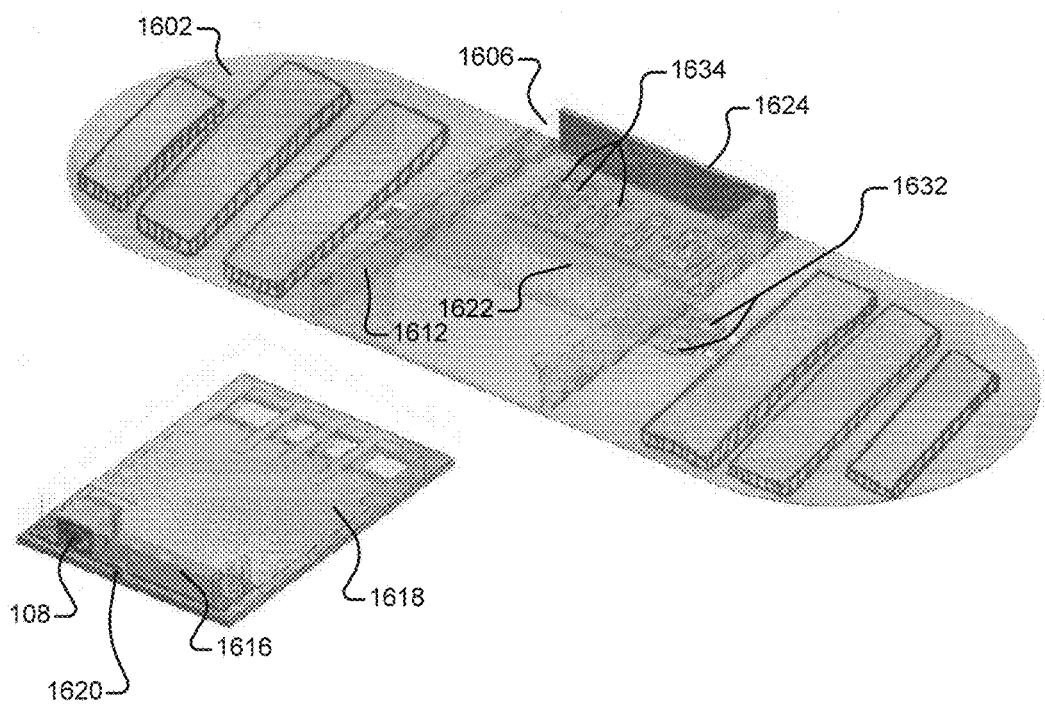
Figure 16E:
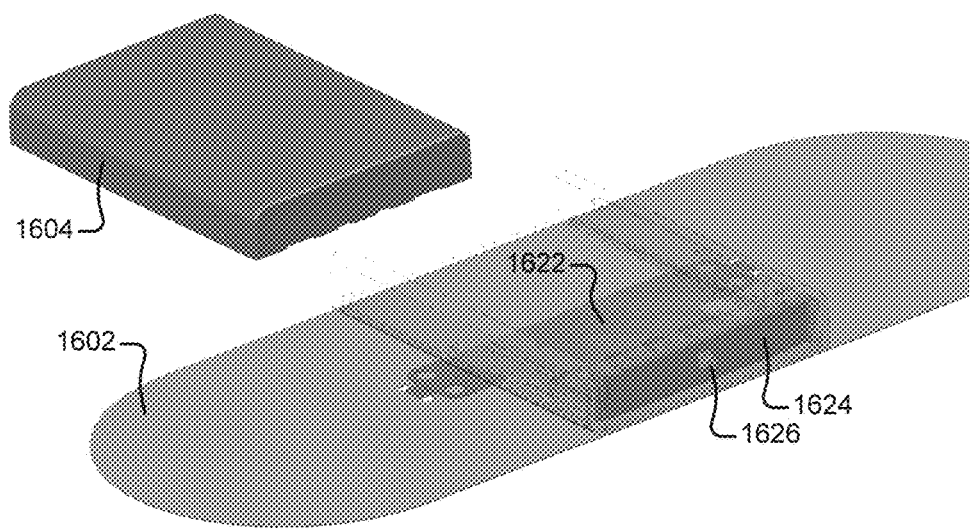
Figure 16F:
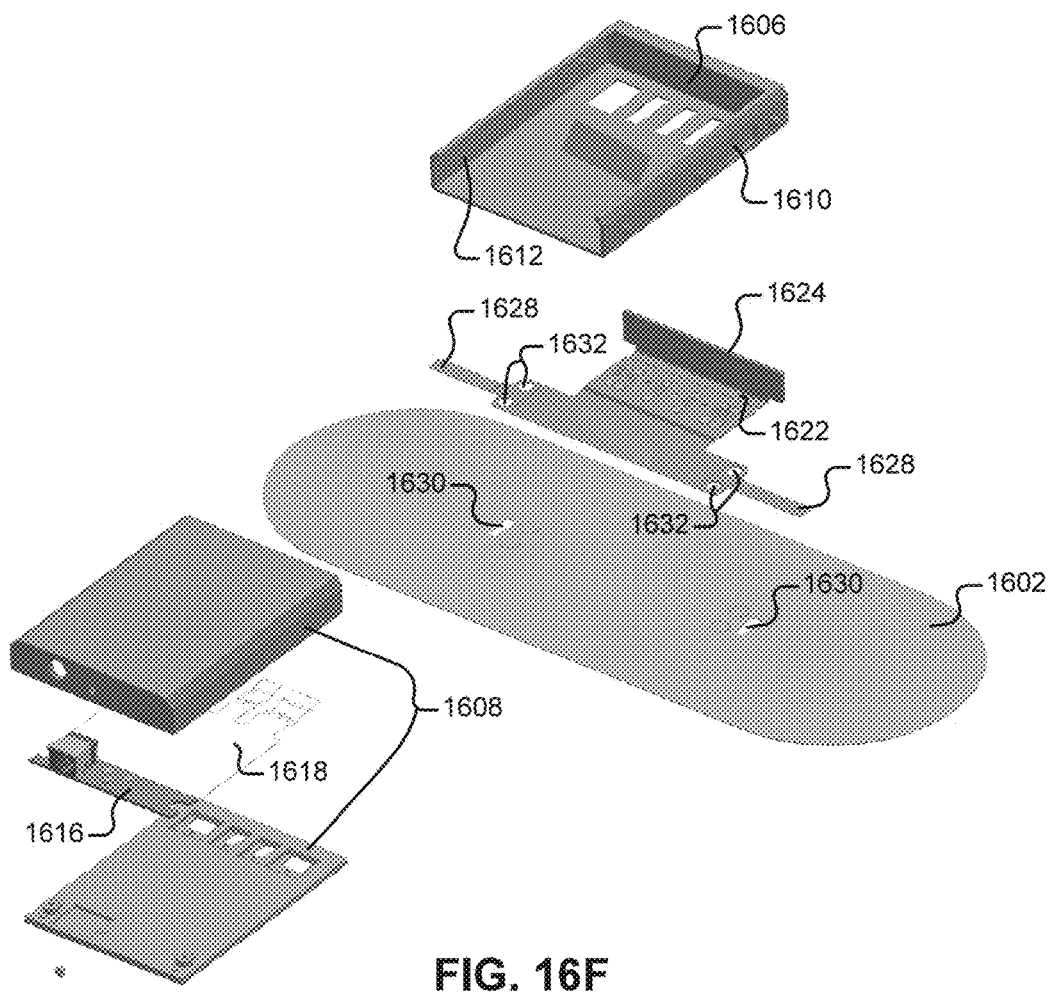

FIGS. 16A-16F illustrate a third example cooling device 100-3. The cooling device 100-3 includes cooling units 1600 attached to a package substrate 1602. The cooling units 1600 are illustrated in FIGS. 16C-16D. The cooling units are omitted from FIGS. 16E-16F in order to highlight other components of the cooling device 100-3.

The cooling device 100-3 includes a removable battery housing 1604. The battery housing 1604 includes a battery (not shown). In some implementations, the battery housing 1604 may also include device electronics. Accordingly, the battery housing 1604 may also be referred to as a "battery and electronics housing 1604." The user may remove/replace the battery housing 1604. For example, the user may replace the battery housing 1604 with other battery housings including fully charged batteries and/or batteries with different capacities. In some implementations, the battery housing 1604 may have a different geometry than that illustrated in FIGS. 16A-16F. For example, a battery housing including a battery with a larger capacity may have a larger volume and/or different shape than that illustrated in FIGS. 16A-16F.

The battery housing 1604 mates with a receptacle 1606. In the example of FIG. 16C, the battery housing 1604 defines indentations 1608 that mate with retention clips 1610 included on the receptacle 1606. The user can slide the battery housing 1604 into the receptacle 1606 along rails 1612 defined by the receptacle 1606. The battery housing 1604 is seated and retained in position by the mating between the retention clips 1610 and indentations 1608. When the battery housing 1604 is seated in the receptacle 1606, the user can apply a force to the battery housing 1604 to unseat the battery housing 1604 from the receptacle 1606. For example, the user can apply a force to the battery housing 1604 that causes the indentations 1608 to spread the retention clips 1610 and then causes the battery housing 1604 to slide out of the receptacle 1606 along the rails 1612. The illustrated battery housing 1604 and receptacle 1606 are only one example retention mechanism for a removable battery housing. The battery housing may be attached and retained by other retention mechanisms, such as an electrical connector (e.g., friction between electrical contacts), a magnetic latch, a push/push mechanism (e.g., such as on a ballpoint pen), and/or a mechanical hook/latch (e.g., a user actuated connector).

The cooling device 100-3 includes thermal reservoir material 1614 that is attached to the package substrate 1602 and the cooling units 1600 on the side of the cooling device 100-3 facing away from the user's body during use. The thermal reservoir material 1614 may also provide comfort to the user during use. For example, the thermal reservoir material 1614 may even out the pressure against the user if the cooling device 100-3 is sandwiched between the user and an object (e.g., a chair back). Specifically, in FIG. 16A, the thermal reservoir material 1614 can help distribute pressure along the entire cooling device 100-3, which may otherwise be focused under the battery housing 1604 and receptacle 1606.

The cooling device 100-3 includes multiple flexible and rigid PCBs. With respect to FIG. 16D and FIG. 16F, the battery housing 1604 includes a first rigid PCB 1616 and a first flexible PCB 1618 that are connected to one another. The first rigid PCB 1616 includes a power input port 108 and a battery indicator 1620. The battery indicator 1620 may indicate a variety of statuses associated with the battery, such as the charge level of the battery and whether the battery is being charged. The first flexible PCB 1618 includes electrical traces that connect the battery to the electronics included on the first rigid PCB 1616. The first flexible PCB 1618 also includes electrical traces that connect to the electrical contacts on the second flexible PCB 1622 (e.g., FIG. 16D). The first rigid PCB 1616, the first flexible PCB 1618, and/or the battery may also include circuits similar to those included in the power module 1008 of FIG. 10.

The cooling device 100-3 includes a second rigid PCB 1624 and a second flexible PCB 1622 that are connected to one another. The second rigid PCB 1624 includes device electronics described herein, such as electronics included in the communication module 1004, processing module 1002, memory 1020, temperature sensing module 1012, cooling control module 1010, and interface module 1006. The LED 1626 on the cooling device 100-3 may indicate if the cooling device 100-3 is turned on, if it is connected to a user device 104 (e.g., via Bluetooth), if it is cooling, and/or the state of the battery.

The second flexible PCB 1622 can be attached to the package substrate 1602 in a variety of ways. For example, the second flexible PCB 1622 can be bonded to the package substrate 1602 using adhesive bonding, heat welding, ultrasonic welding, mechanical attachments, or other technique. The second flexible PCB 1622 includes temperature sensors 1628 that extend through openings 1630 defined in the package substrate 1602. The temperature sensors 1628 are positioned between the package substrate 1602 and the user during use. The second flexible PCB 1622 also includes electrical contacts 1632 that solder to electrical contacts of cooling elements 1600.

The second flexible PCB 1622 includes electrical contacts 1634 (e.g., 6 illustrated contacts) that electrically couple the battery and electronics included in the battery housing 1604 to the device electronics included on the second flexible PCB 1622 and the second rigid PCB 1624. For example, the contacts 1634 may deliver power from the battery to the second flexible PCB 1622 and the second rigid PCB 1624. The electrical contacts 1634 may also provide for communication between components included in the battery housing 1604 and components on the receptacle side of the cooling device 100-3. For example, the contacts 1634 may allow electronics on the second rigid PCB 1624 to determine the battery serial number/ID, the battery size, the state of charge, the battery temperature, the battery usage time, and other data.

The arrangement of PCBs and device electronics described with respect to FIGS. 16A-16F is only one example arrangement of PCBs and device electronics. In other examples, the cooling device 100-3 may include other arrangements of PCBs and device electronics. For example, the cooling device 100-3 may include other arrangements of flexible and/or rigid PCBs. As another example, the battery housing 1604 may include additional device electronics, such as device electronics included in the communication module 1004, processing module 1002, memory 1020, temperature sensing module 1012, cooling control module 1010, and interface module 1006.

Note that the cooling device 100-3 does not include a manual user input button. For example, the cooling device 100-3 does not include an on/off button for turning cooling device 100-3 on/off. Instead of controlling the cooling device 100-3 using manual buttons included on the cooling device 100-3, the user may control the cooling device 100-3 via the user device 104. For example, the user may interact with a GUI on the user device 104 to turn the cooling device 100-3 on/off or place the cooling device 100-3 in a standby/sleep mode.

Figure 17A:
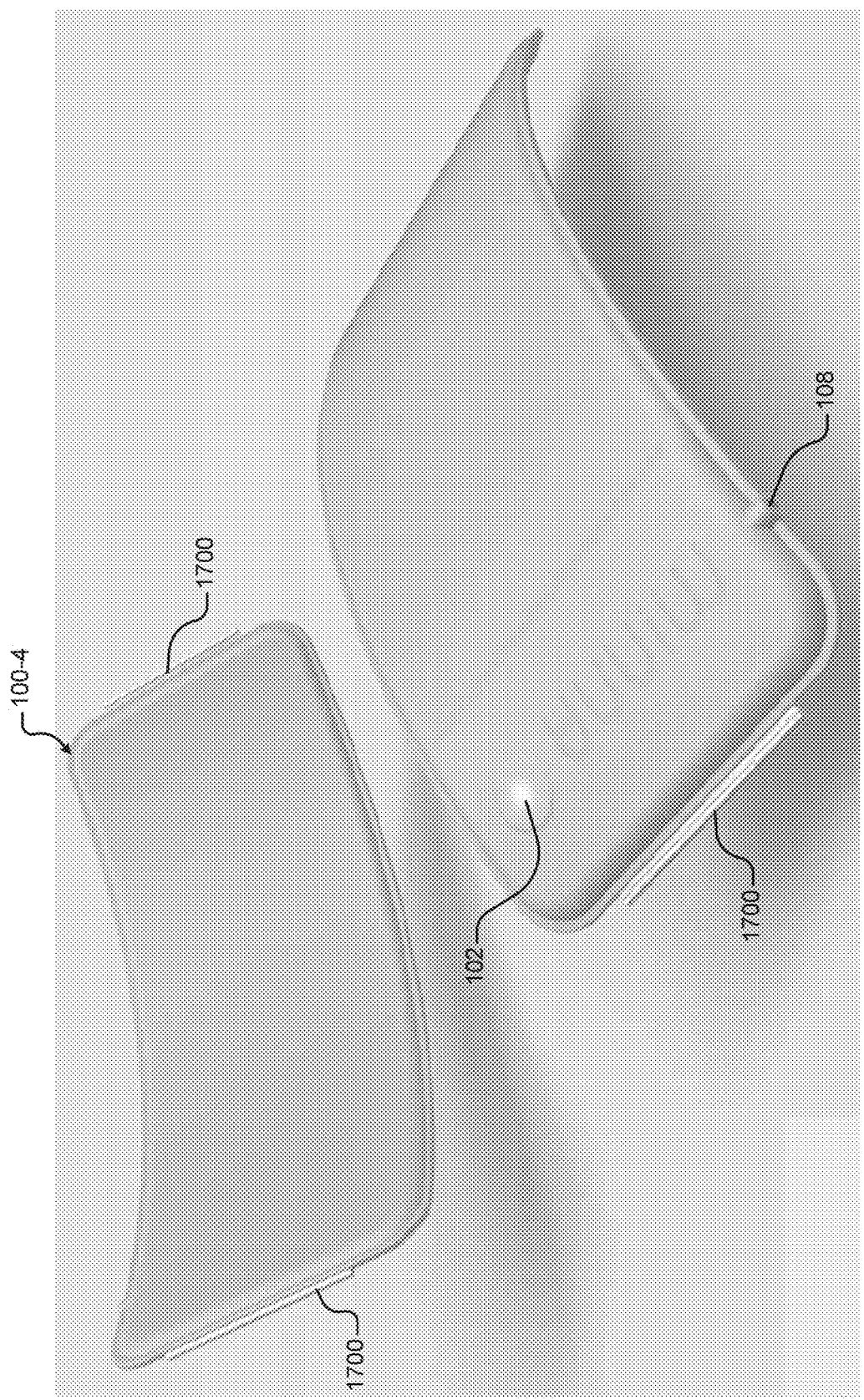
Figure 17B:
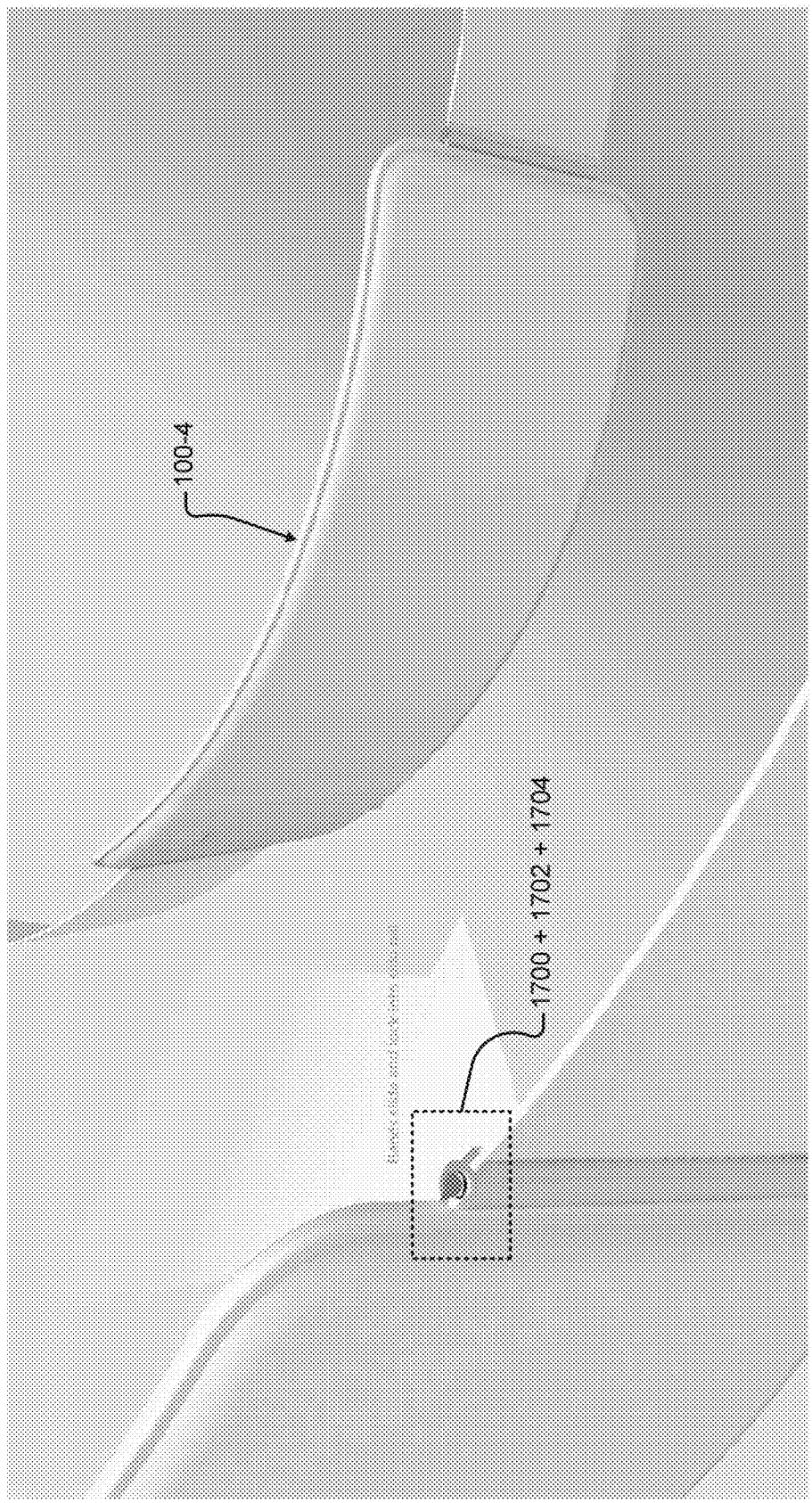
Figure 17C:
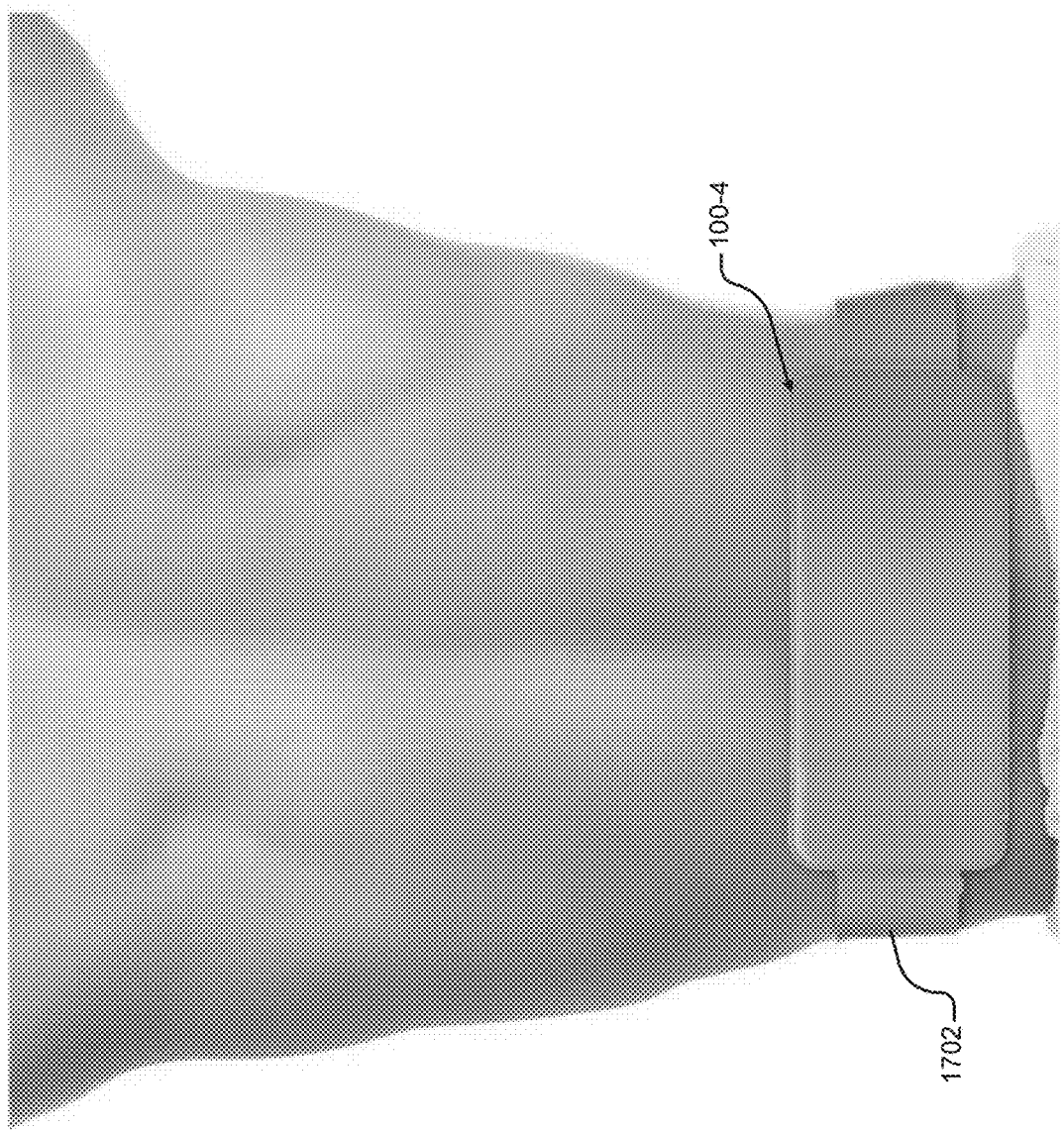

FIGS. 17A-17C illustrate a fourth cooling device 100-4. The fourth cooling device package can include one or more cooling units 200 arranged in any manner throughout the package. The fourth cooling device 100-4 can be applied to different parts of the user's body (e.g., the back or stomach). The fourth device package can include one or more connectors 1700 (device connectors) that are configured to connect to a belt 1702 having connectors 1704 (belt connectors) that mate with the device connectors 1700 of the fourth device package (see FIG. 17B). With respect to FIG. 17A, the fourth cooling device 100-4 can include a user input button (e.g., an on/off button) and a power input port.

The fourth cooling device 100-4 of FIGS. 17A-17C may include similar layers as the second and third cooling devices 100-2, 100-3, such as the encapsulation layers, package substrate, cooling units, and a thermal reservoir layer. The arrangement of the components within the fourth cooling device 100-4 may be different than the arrangement of components within the second and third cooling devices 100-2, 100-3. For example, the battery, user input button, and power input port of the fourth cooling device 100-4 may be offset to one side, whereas these components are centrally located in the second cooling device 100-2. In some implementations, the fourth cooling device 100-4 may also include an adhesive layer that may be attached to the encapsulation bottom cover.

FIGS. 18A-18E illustrate a fifth cooling device 100-5. The fifth cooling device package can include one or more cooling units 200 arranged in any manner throughout the package. The fifth cooling device 100-5 can be applied to different parts of the user's body (e.g., see FIG. 18D). The fifth device package can include one or more belt loops 1800. The belt loops 1800 of the fifth device package, which are located at the edges of the fifth device package, may be integrated with the encapsulation top cover 1802. The fifth cooling device 100-5 can include a user input button 102 (e.g., an on/off button) and a power input port (not illustrated).

Figure 18A:
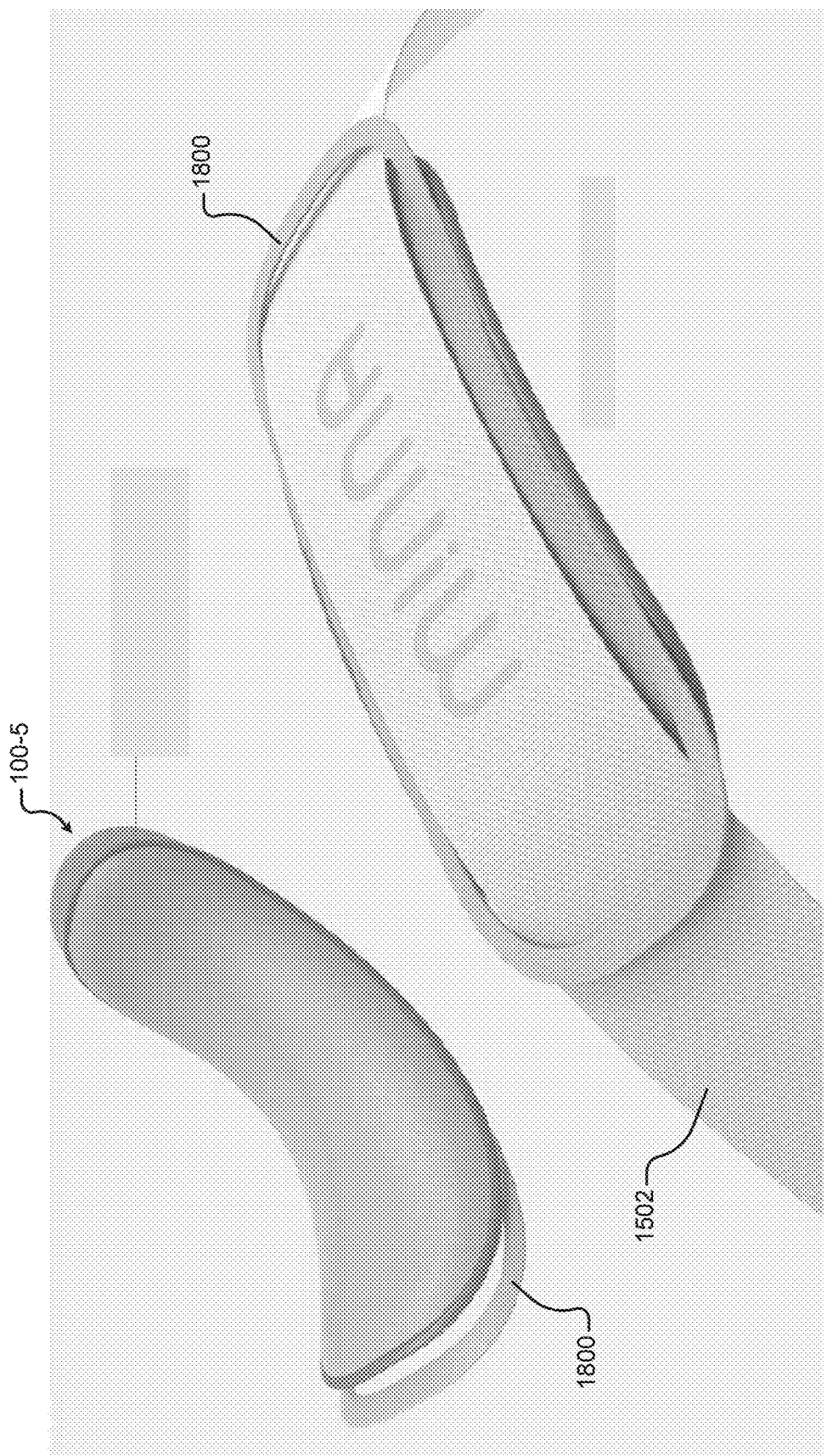
Figure 18B:
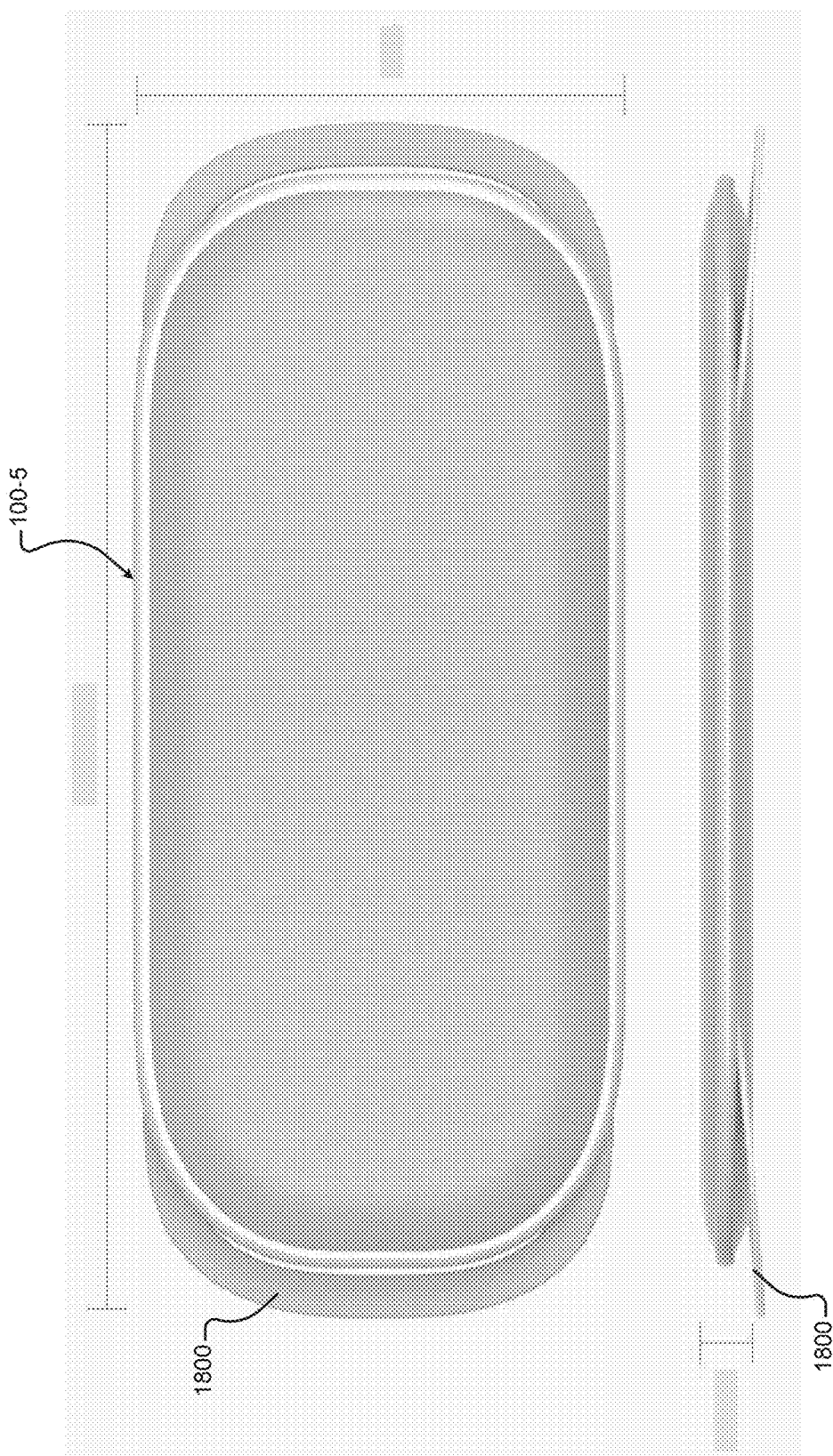
Figure 18C:
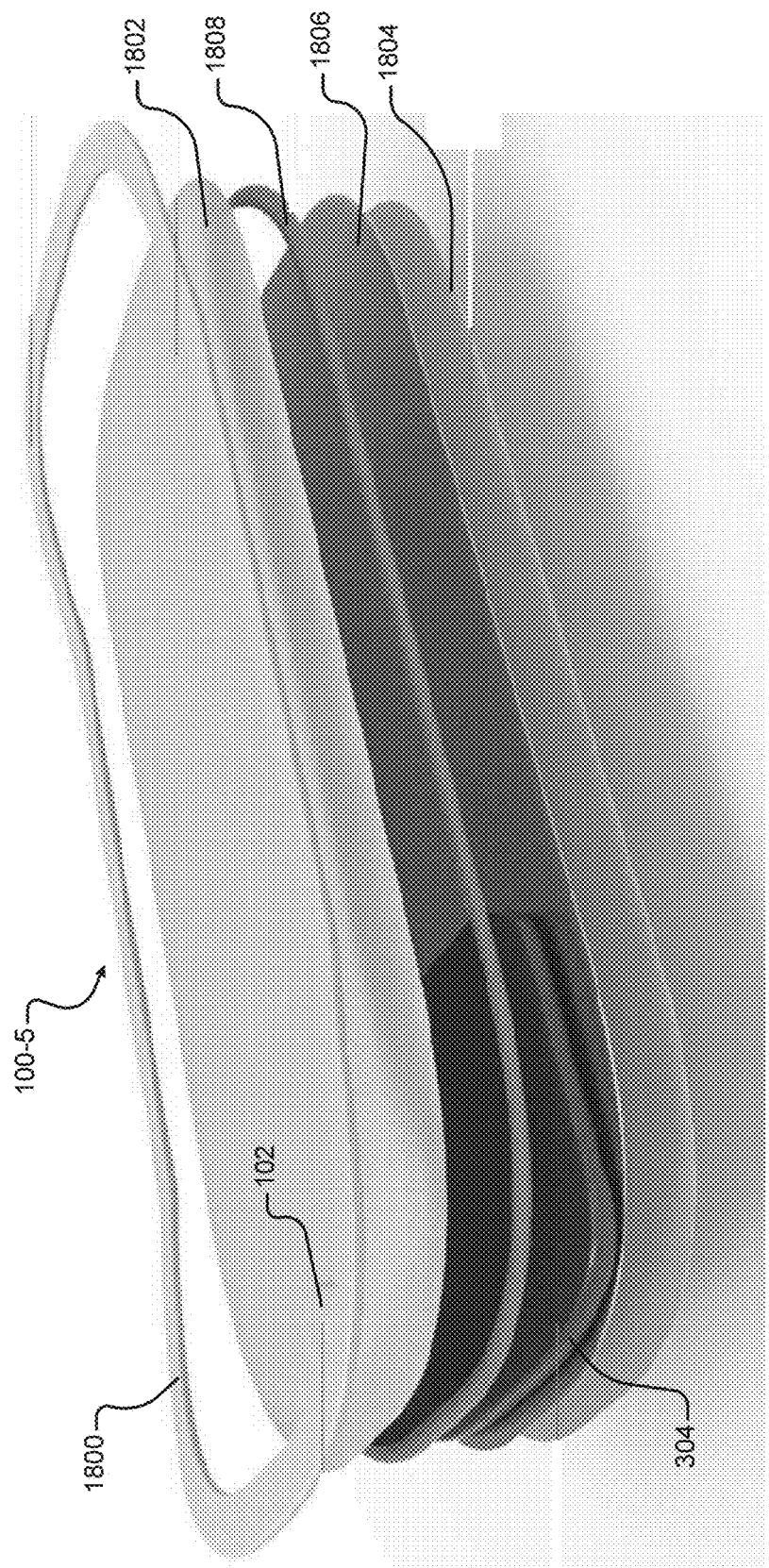
Figure 18D:

Referring to FIG. 18C, the fifth cooling device 100-5 may include similar layers as the second cooling device 100-2, such as the encapsulation layers 1802, 1804, package substrate 1806, and cooling units (not illustrated). The fifth cooling device 100-5 also includes a shape retention element 1808 (e.g., a moldable wire or plastically deformable material) that the user can use to form the fifth cooling device 100-5 into a shape that is maintained by the shape retention element 1808. The shape retention element 1808 may be used to shape and fix the fifth cooling device 100-5 to the user's body (e.g., around the shoulder in FIG. 18D, waist, arm, hand, leg, foot, neck, or head). For example, the shape retention element 1808 (e.g., the wire) may be pressed to conform to the user's body and maintain its shape so that the fifth cooling device 100-5 conforms to the user's body when the user removes their hand from the fifth cooling device 100-5. Since the belt loops 1800 are integrated into the perimeter of the fifth cooling device 100-5, the belt loops 1800 may also conform to whatever shape the fifth cooling device 100-5 takes. Although the shape retention element 1808 is included around the perimeter of the fifth cooling device 100-5, a cooling device may include one or more shape retention elements along one or more axes of the cooling device.

Figure 19A:
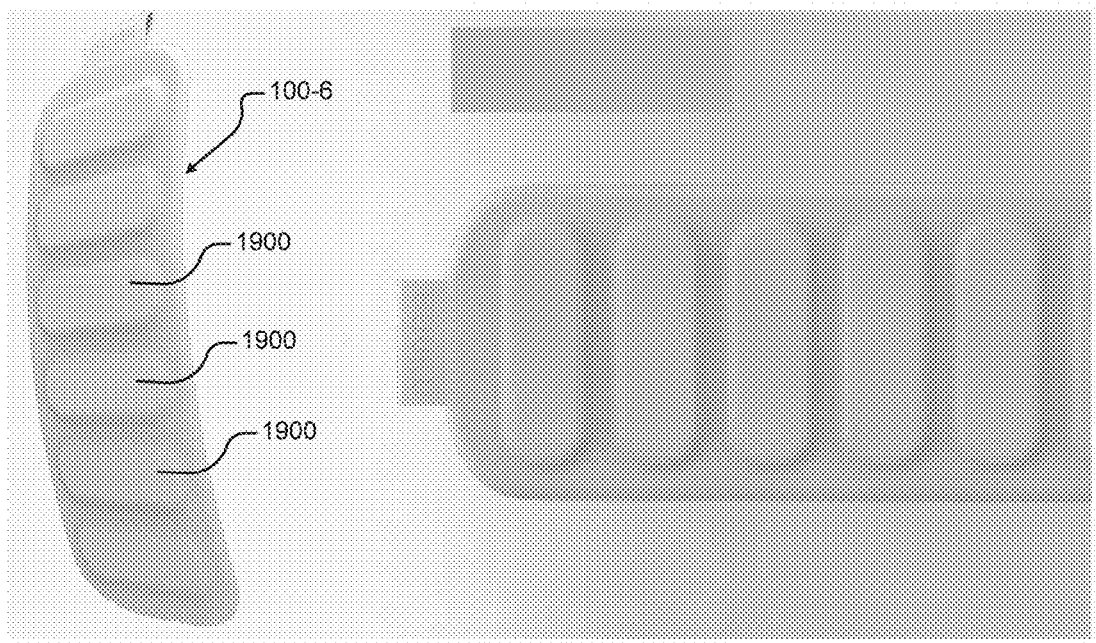
Figure 19B:
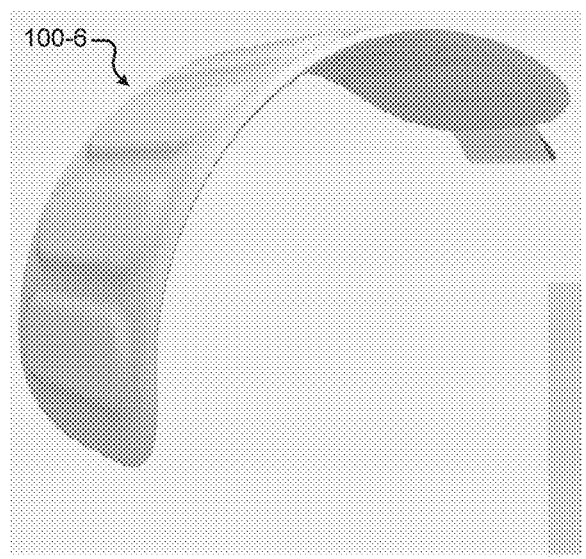
Figure 19C:

FIGS. 19A-19C illustrate a sixth cooling device 100-6 having a sixth device package. The sixth device package separates different components into different pods 1900. The pods 1900 may include different components. In some examples, one or more pods 1900 may include the battery and device electronics. In these examples, the remaining pods may include cooling units. In some implementations, the cooling units may be distributed throughout the full surface of the cooling device 100-6 or beneath some, or all, of the pods 1900. The sixth cooling device 100-6 may include similar layers as the other cooling devices, such as encapsulation layers, cooling units, and an adhesive layer. Separation of the components into different pods may allow the sixth cooling device 100-6 to easily fold/roll in one direction. The flexibility of the sixth cooling device 100-6 may help it conform to the user's body (e.g., a user's shoulder) as illustrated in FIG. 19C.

Figure 20:
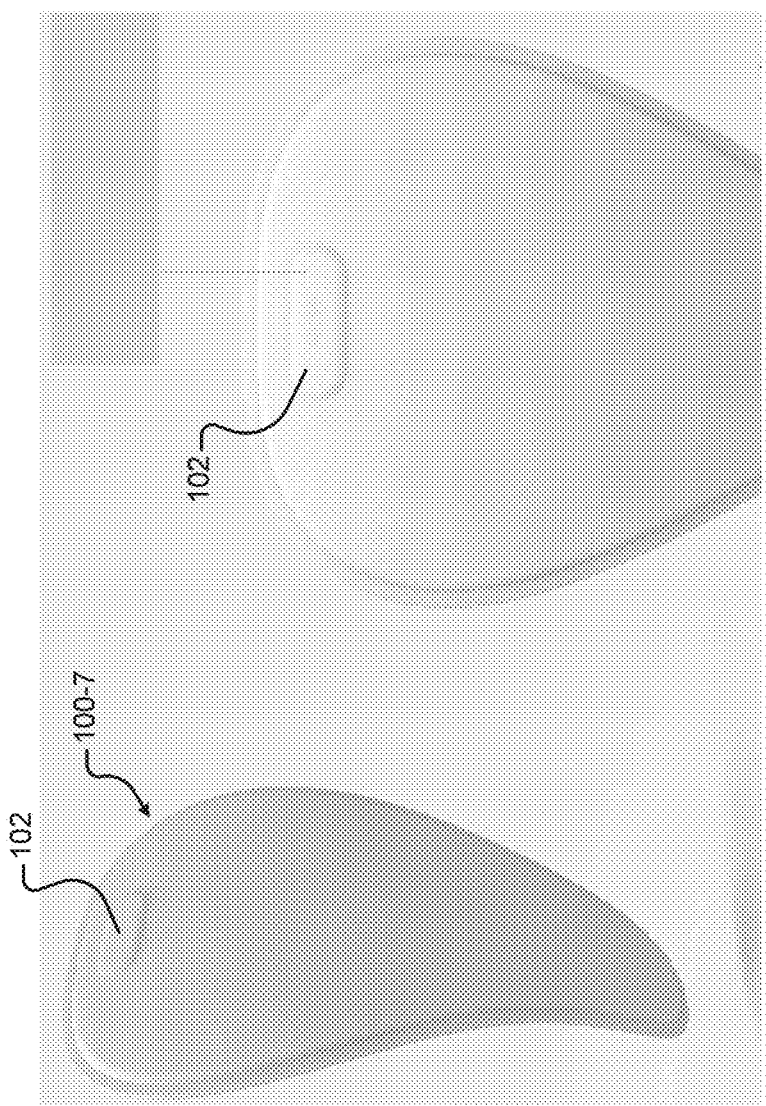

FIG. 20 illustrates a seventh cooling device 100-7 having a seventh device package. The seventh cooling device 100-7 is shaped to conform to a female's pelvic region. The seventh cooling device 100-7 may include similar layers and components as the other cooling devices, such as user input buttons 102, device electronics, a battery, encapsulation layers, a package substrate, cooling units, and an adhesive layer. The seventh cooling device 100-7 may be flexible so that it conforms to the user's body. In some implementations, the seventh cooling device 100-7 (or any other cooling device) may be made from water repellant materials.

Figure 21A:
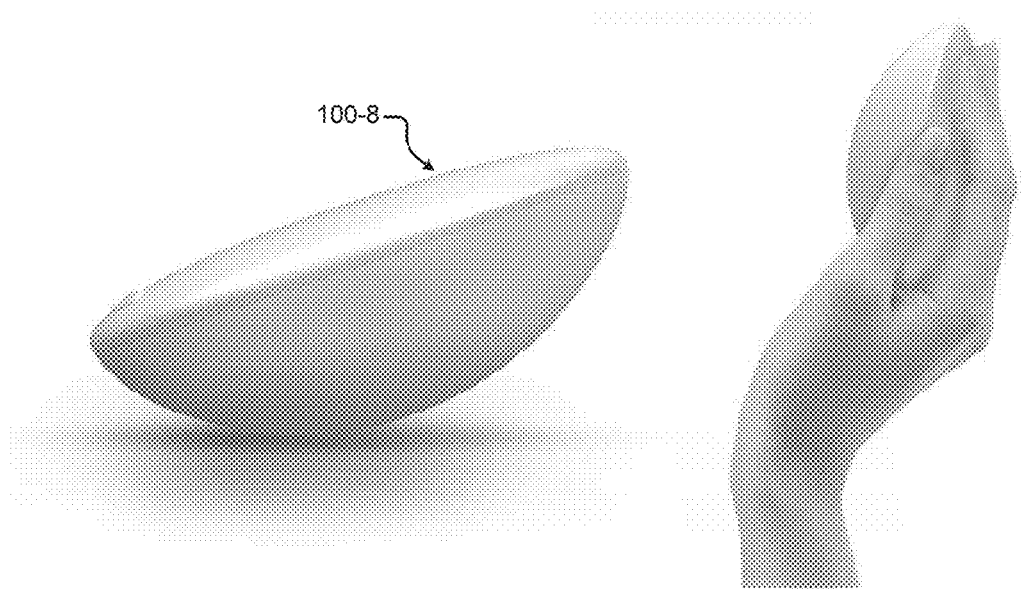
Figure 21B:
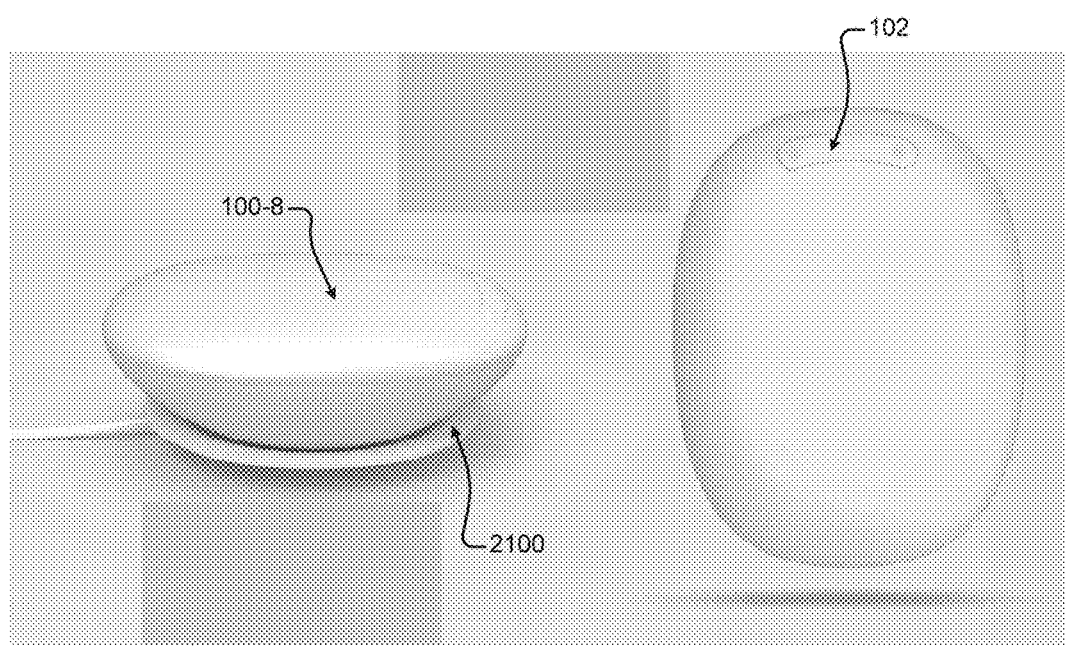

FIGS. 21A-21B illustrate an eighth cooling device 100-8. The eighth cooling device 100-8 is configured to fit into a user's hand. The flattened portion of the eighth cooling device 100-8 includes user input buttons 102 that the user may actuate in order to increase/decrease the amount of cooling generated by the eighth cooling device 100-8. The convex portion of the eighth cooling device 100-8 may act as the cold side and may be soft and compliant to promote comfortable contact with the user's body. The convex portion of the eighth cooling device 100-8 may also include a thermal reservoir material in order to extend the operating time of the eighth cooling device 100-8. The eighth cooling device 100-8 may also include circuits for wireless charging. For example, the eighth cooling device 100-8 may be wirelessly charged from the wireless charging station 2100 illustrated in FIG. 21B.

Figure 22A:
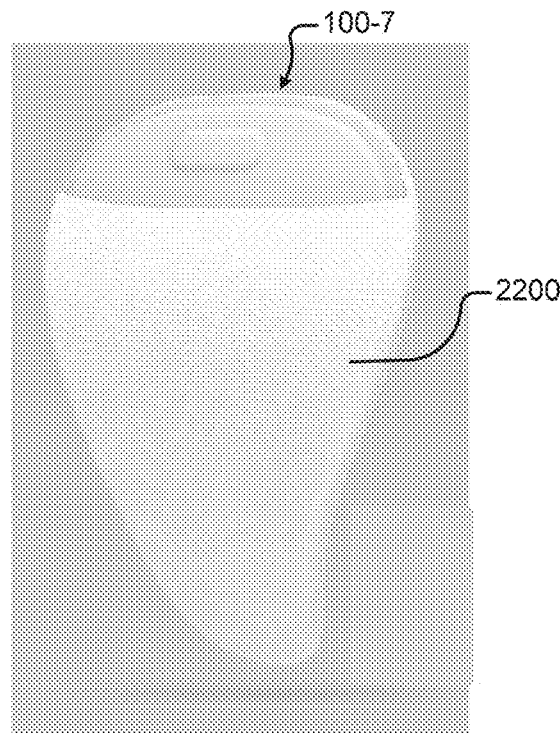
FIGS. 22A-22E illustrate example sleeves and garments that hold cooling devices.
Figure 22B:

FIGS. 22A-22E illustrate various sleeves and garments that may be configured to hold the cooling devices 100 described herein. FIG. 22A illustrates an example sleeve 2200 that holds the seventh cooling device 100-7. The sleeve 2200 of FIG. 22A may be fabricated from a cloth material (e.g., cotton or other fabric). In some implementations, the sleeve 2200 may be fabricated from a material that is thermally conductive. In some implementations, the sleeve 2200 may be fabricated from a breathable material. FIG. 22B illustrates another sleeve 2202. The sleeve 2202 of FIG. 22B is a weighted sleeve configured to hold the second cooling device 100-2. The weighted sleeve 2202 may apply pressure to the cooling device during use (e.g., while resting on the user).

Figure 22D:
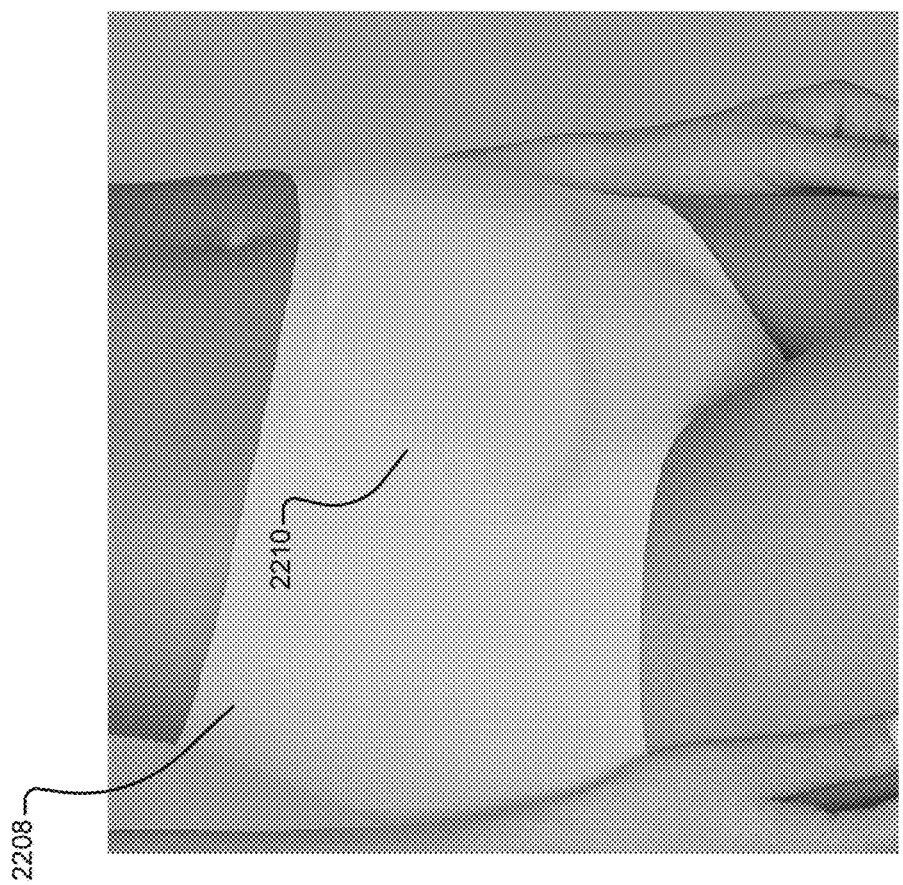
Figure 22C:
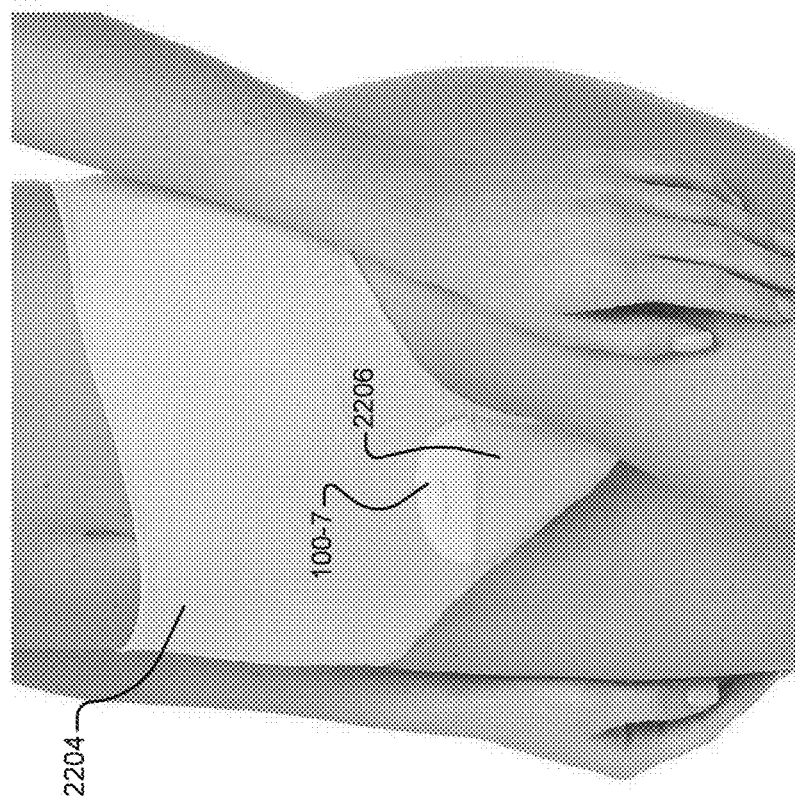
Figure 22E:
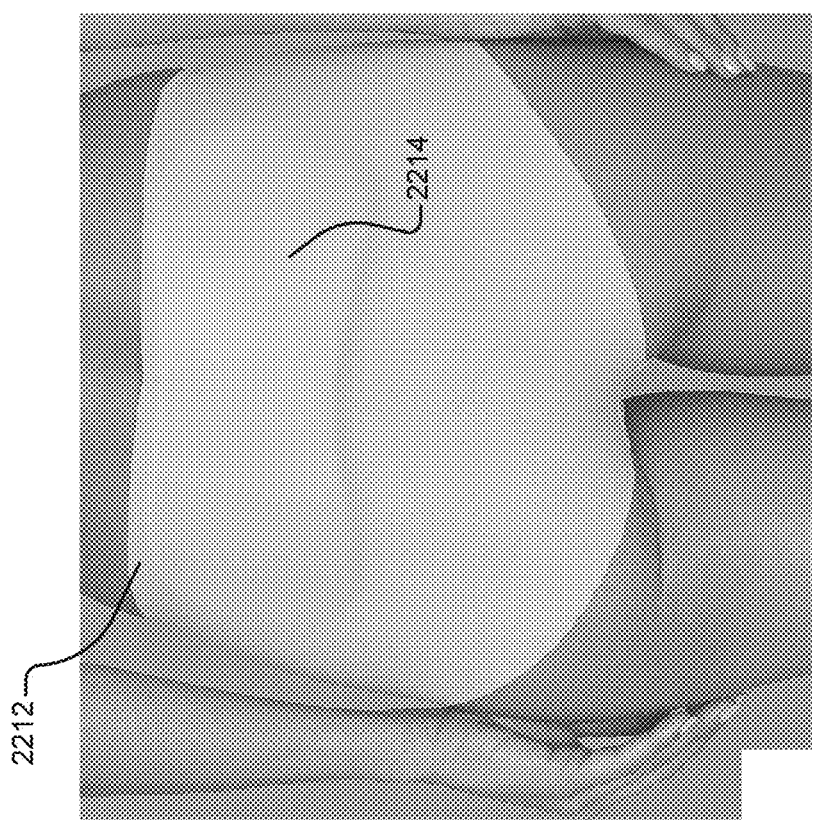

FIGS. 22C-22E illustrate garments that are configured to hold the cooling devices 100. FIG. 22C is a female underwear garment 2204 including a device pouch 2206 that is shaped to hold the seventh cooling device 100-7 in the pelvic region. FIG. 22D is another underwear garment 2208 including a device pouch 2210 for holding a cooling device. Specifically, the garment 2208 of FIG. 22D includes a device pouch 2210 that holds the second cooling device 100-2 above the pubic region. FIG. 22E illustrates an additional example underwear garment 2212 for women that includes a device pouch 2214 for holding the second cooling device 100-2 in the user's lower back.

Although a single cooling device 100 in communication with a user device 104 is illustrated and described herein, in some implementations, a single user device 104 may communicate with multiple cooling devices 100. For example, a user may place two cooling devices on their body and control/monitor the two cooling devices using a single user device.

Although the package substrate is illustrated herein as holding the cooling units 200, in some implementations, the cooling units 200 may be held within the device package in other manners. For example, the top and bottom of the cooling units 200 may be sandwiched between two different substrates (e.g., each similar to the package substrate 300). As another example, the cooling units 200 may be attached to the top and/or bottom encapsulation layers which may serve to hold the cooling 200 units in place.

Various examples have been described. These and other examples are within the scope of the following claims.

What is claimed is:

1. A cooling device comprising:
   a package substrate;
   a plurality of cooling units configured to cool a user's body, each cooling unit comprising a plurality of semiconductor cooling elements sandwiched between a first cooling unit substrate and a second cooling unit substrate, wherein each of the cooling units is connected to the package substrate; and
   device electronics coupled to the cooling units, the device electronics configured to:
   store a first cooling device profile that includes data indicating an amount of power to deliver to each of the cooling units over a period of time;
   deliver power to the cooling units according to the first cooling device profile;
   wirelessly receive a second cooling device profile from an external computing device; and
   deliver power to the cooling units according to the second cooling device profile.

2. The cooling device of claim 1, wherein the package substrate is flexible.

3. The cooling device of claim 1, wherein each first cooling unit substrate and each second cooling unit substrate of the plurality of cooling units is flexible.

4. The cooling device of claim 1, further comprising a user input device configured to receive user input, wherein the user input device communicates with the device electronics, and wherein the device electronics are configured to modify the delivery of power to the cooling units in response to user input received by the user input device.

5. The cooling device of claim 1, wherein the device electronics are configured to:
wirelessly receive user-input instructions from the external computing device indicating how to modify the delivery of power to the cooling units; and
modify the delivery of power to the cooling units in response to the received user-input instructions.

6. The cooling device of claim 1, further comprising a temperature sensor that generates a temperature signal indicating the temperature in proximity to the temperature sensor, wherein the device electronics are configured to deliver power to the cooling units based on the temperature signal.

7. The cooling device of claim 1, further comprising a thermal reservoir material in contact with one or more of the cooling units.

8. The cooling device of claim 7, wherein the thermal reservoir material includes a phase change material.

9. The cooling device of claim 7, wherein the thermal reservoir material includes one or more metal strips.

10. The cooling device of claim 7, wherein the thermal reservoir material includes a liquid.

11. A cooling device comprising:
a plurality of cooling units configured to cool a user's body, each cooling unit comprising a plurality of semiconductor cooling elements sandwiched between a first cooling unit substrate and a second cooling unit substrate;
device electronics coupled to the cooling units, the device electronics configured to deliver power to each of the cooling units to cool the user's body, wherein the delivery of power to the cooling units causes the transfer of heat from the first cooling unit substrates to the second cooling unit substrates; and
a thermal reservoir material in contact with the second cooling unit substrates.

12. The cooling device of claim 11, wherein the thermal reservoir material includes a phase change material.

13. The cooling device of claim 11, wherein the thermal reservoir material includes one or more metal strips.

14. The cooling device of claim 11, wherein the thermal reservoir material includes a liquid.

15. The cooling device of claim 11, further comprising a flexible package substrate, wherein each of the cooling units is connected to the flexible package substrate.

16. The cooling device of claim 11, wherein the first cooling unit substrates and the second cooling unit substrates are flexible.

17. The cooling device of claim 11, further comprising a user input device configured to receive user input, wherein the user input device communicates with the device electronics, and wherein the device electronics are configured to modify the delivery of power to the cooling units in response to user input received by the user input device.

18. The cooling device of claim 11, wherein the device electronics are configured to:
wirelessly receive user-input instructions from an external computing device indicating how to modify the delivery of power to the cooling units; and
modify the delivery of power to the cooling units in response to the received user-input instructions.

19. The cooling device of claim 11, further comprising a temperature sensor that generates a temperature signal indicating the temperature in proximity to the temperature sensor, wherein the device electronics are configured to deliver power to the cooling units based on the temperature signal.

20. The cooling device of claim 11, wherein the device electronics are configured to:
store a first cooling device profile that includes data indicating an amount of power to deliver to each of the cooling units over a period of time;
deliver power to the cooling units according to the first cooling device profile;
wirelessly receive a second cooling device profile from an external computing device; and
deliver power to the cooling units according to the second cooling device profile.

* * * * *